(12) United States Patent
Campopiano et al.

(10) Patent No.: US 12,421,503 B2
(45) Date of Patent: *Sep. 23, 2025

(54) KETOREDUCTASE POLYPEPTIDES FOR THE PRODUCTION OF AZETIDINONE

(71) Applicant: Codexis, Inc., Redwood City, CA (US)

(72) Inventors: Onorato Campopiano, Hayward, CA (US); Emily Mundorff, Garden City, NY (US); Birthe Borup, Wesel (DE); Rama Voladri, Pleasanton, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/472,540

(22) Filed: Sep. 22, 2023

(65) Prior Publication Data

US 2024/0141304 A1 May 2, 2024

Related U.S. Application Data

(60) Continuation of application No. 17/357,673, filed on Jun. 24, 2021, now Pat. No. 12,049,649, which is a continuation of application No. 16/790,474, filed on Feb. 13, 2020, now Pat. No. 11,078,466, which is a division of application No. 16/404,988, filed on May 7, 2019, now Pat. No. 10,597,641, which is a division of application No. 15/631,359, filed on Jun. 23, 2017, now Pat. No. 10,329,540, which is a continuation of application No. 15/408,673, filed on Jan. 18, 2017, now Pat. No. 9,719,071, which is a continuation of application No. 15/272,664, filed on Sep. 22, 2016, now Pat. No. 9,580,694, which is a division of application No. 15/175,317, filed on Jun. 7, 2016, now Pat. No. 9,476,034, which is a continuation of application No. 14/822,624, filed on Aug. 10, 2015, now Pat. No. 9,382,519, which is a continuation of application No. 14/658,407, filed on Mar. 16, 2015, now Pat. No. 9,133,442, which is a continuation of application No. 13/925,096, filed on Jun. 24, 2013, now Pat. No. 8,980,606, which is a continuation of application No. 13/569,900, filed on Aug. 8, 2012, now Pat. No. 8,470,572, which is a division of application No. 12/977,825, filed on Dec. 23, 2010, now Pat. No. 8,257,952, which is a continuation of application No. 12/243,968, filed on Oct. 1, 2008, now Pat. No. 7,883,879.

(60) Provisional application No. 60/976,555, filed on Oct. 1, 2007.

(51) Int. Cl.
  *C12N 9/04* (2006.01)
  *C12P 17/10* (2006.01)

(52) U.S. Cl.
  CPC ............ *C12N 9/0006* (2013.01); *C12P 17/10* (2013.01); *C12Y 101/01184* (2013.01); *Y02P 20/52* (2015.11)

(58) Field of Classification Search
  None
  See application file for complete search history.

(56) References Cited

U.S. PATENT DOCUMENTS

| | | |
|---|---|---|
| 4,619,924 A | 10/1986 | Hamanaka |
| 4,981,992 A | 1/1991 | Sayo et al. |
| 5,064,761 A | 11/1991 | Schneider et al. |
| 5,200,335 A | 4/1993 | Hummel et al. |
| 5,225,339 A | 7/1993 | Wong et al. |
| 5,342,767 A | 8/1994 | Wong et al. |
| 5,427,933 A | 6/1995 | Chen et al. |
| 5,491,077 A | 2/1996 | Chartrain et al. |
| 5,559,030 A | 9/1996 | Matsuyama et al. |
| 5,700,670 A | 12/1997 | Yamagishi et al. |
| 5,712,388 A | 1/1998 | Matsumoto et al. |
| 5,891,685 A | 4/1999 | Yamagishi et al. |
| 6,037,158 A | 3/2000 | Hummel et al. |
| 6,117,679 A | 9/2000 | Stemmer |
| 6,225,099 B1 | 5/2001 | Hummel et al. |
| 6,376,246 B1 | 4/2002 | Crameri et al. |
| 6,399,339 B1 | 6/2002 | Wolberg et al. |
| 6,413,750 B1 | 7/2002 | Hummel et al. |
| 6,586,182 B1 | 7/2003 | Patten et al. |
| 6,645,746 B1 | 11/2003 | Kizaki et al. |
| 6,800,477 B2 | 10/2004 | Patel et al. |

(Continued)

FOREIGN PATENT DOCUMENTS

| | | |
|---|---|---|
| EP | 369691 B1 | 7/1994 |
| EP | 1176203 A1 | 1/2002 |

(Continued)

OTHER PUBLICATIONS

Siloto et al. (Site saturation mutagenesis: Methods and applications in protein engineering, Biocatalysis and Agricultural Biotechnology 1 (2012) 181-189) (Year: 2012).*

(Continued)

*Primary Examiner* — Manjunath N Rao
*Assistant Examiner* — Jae W Lee
(74) *Attorney, Agent, or Firm* — FisherBroyles, LLP; Adam K. Whiting

(57) ABSTRACT

The present disclosure provides engineered ketoreductase enzymes having improved properties as compared to a naturally occurring wild-type ketoreductase enzyme. Also provided are polynucleotides encoding the engineered ketoreductase enzymes, host cells capable of expressing the engineered ketoreductase enzymes, and methods of using the engineered ketoreductase enzymes to synthesize a variety of chiral compounds.

14 Claims, 1 Drawing Sheet
Specification includes a Sequence Listing.

(56) References Cited

U.S. PATENT DOCUMENTS

| | | |
|---|---|---|
| 7,083,962 B2 | 8/2006 | Kimoto et al. |
| 7,820,421 B2 | 10/2010 | Ching et al. |
| 7,883,879 B2 | 2/2011 | Campopiano et al. |
| 7,977,078 B2 | 7/2011 | Liang et al. |
| 8,088,610 B2 | 1/2012 | Liang et al. |
| 8,257,952 B2 | 9/2012 | Campopiano et al. |
| 8,470,572 B2 | 6/2013 | Campopiano et al. |
| 8,748,143 B2 | 6/2014 | Liang et al. |
| 8,980,606 B2 | 3/2015 | Campopiano et al. |
| 9,133,442 B2 | 9/2015 | Campopiano et al. |
| 9,382,519 B2 | 7/2016 | Campopiano et al. |
| 9,476,034 B2 | 10/2016 | Campopiano et al. |
| 9,580,694 B2 | 2/2017 | Campopiano et al. |
| 9,719,071 B2 | 8/2017 | Campopiano et al. |
| 10,329,540 B2 | 6/2019 | Campopiano et al. |
| 10,597,641 B2 | 3/2020 | Campopiano et al. |
| 11,078,466 B2 | 8/2021 | Campopiano et al. |
| 2002/0061564 A1 | 5/2002 | Rozzell |
| 2003/0054520 A1 | 3/2003 | Bommanus et al. |
| 2003/0068811 A1 | 4/2003 | Patel et al. |
| 2004/0265978 A1 | 12/2004 | Gupta et al. |
| 2006/0195947 A1 | 8/2006 | Davis et al. |
| 2006/0286646 A1 | 12/2006 | Patel et al. |
| 2008/0220990 A1 | 9/2008 | Fox |
| 2008/0248539 A1 | 10/2008 | Giver et al. |
| 2008/0318295 A1 | 12/2008 | Ching et al. |
| 2009/0093031 A1 | 4/2009 | Liang et al. |
| 2009/0312196 A1 | 12/2009 | Colbeck et al. |
| 2010/0062499 A1 | 3/2010 | Mundorff et al. |
| 2010/0151534 A1 | 6/2010 | Savile et al. |

FOREIGN PATENT DOCUMENTS

| | | |
|---|---|---|
| EP | 1908845 A1 | 4/2008 |
| WO | 2001/040450 A1 | 6/2001 |
| WO | 2002/086126 A2 | 10/2002 |
| WO | 2005/017135 A1 | 2/2005 |
| WO | 2005/033094 A2 | 4/2005 |
| WO | 005/054491 A1 | 6/2005 |
| WO | 2007/010944 A1 | 1/2007 |
| WO | 2007/012428 A1 | 2/2007 |
| WO | 2008/042876 A2 | 4/2008 |
| WO | 2008/103248 A1 | 8/2008 |

OTHER PUBLICATIONS

Whistock et al., "Prediction of protein function from protein sequence," Q. Rev. Biophysics., 2003, vol. 36 (3):307-340.
Witowski et al., "Conversion of b-ketoacyl synthase to a Malonyl Decarboxylase by replacement of the active cysteine with glutamine," Biochemistry, 1999, vol. 38: 11643-11650.
GenBank Accession No. Q6WVP7 dated Apr. 22, 2003.
Amidjojo et al., 2005, "Asymmetric Synthesis of Tert-butyl (3R, 5S)6-chloro-dihydroxyhexanoate with Lactobacillus kefir," Appl Microbiol Biotechnol., 69:9-15.
Baerga-Ortiz et al., 2006, "Directed Mutagenesis Alters the Stereochemistry of Catalysis by Isolated Ketoreductase Domains from the Erythromycin Polyketide Synthase," Chem Biol., 13(3):277-85.
Bisel et al., 2007, "Stereochemical clarification of the enzyme-catalysed reduction of 2-acetylchromen-4-one," Tetrahedron Asymmetry, 18(9):1142-1144.
Bradshaw et al., 1992, "Lactobacillus kefir Alcohol Dehydrogenase: A Useful Catalyst for Synthesis," J. Org. Chem. 57(5):1532-1536.
Breyer-Pfaff et al., 1999, "High-affinity Stereoselective Reduction of the Enantiomers of Ketotifen and of Ketonic Nortriptyline Metabolites by Aldo-Keto Reductases from Human Liver," Biochem. Pharmacol., 59:249-260.
Cha et al., 2002, "Stereochemical control in diastereoselective reduction of α-substituted-β-ketoesters using a reductase purified from Kluyveromyces marxianus," Biotechnol. Lett , 24:1695-1698.
Database Epo Proteins, Apr. 2007, "Sequence 4 from Patent WO2007012428," XP002488479, retrieved from EBI Accession No. EPOP:CS539287, Database Accession No. CS539287.
Daussmann et al., 2006, "Oxidoreductases and Hydroxynitrilase Lyases: Complementary Enzymatic Technologies for Chiral Alcohols," Eng Life Sci., 6(2):125-129.
Fuganti et al., 1993, "Microbial Generation of (2R,3S)- and (2S,3S)-Ethyl 2-Benzamidomethyl-3-hydroxybutyrate, a Key Intermediate in the Synthesis of (3S, 1'R)-3-(1'-Hydroxyethyl)azetidin-2-one," J Chem. Soc. Perkin Trans. 1:2247-2249.
Genbank Accession No. 1NXQ_A Feb. 11, 2003.
Genbank Accession No. AJ544275 Feb. 5, 2010.
Genbank Accession No. AAP94029 Apr. 1, 2004.
Genbank Accession No. AF160799 Dec. 9, 1999.
Genbank Accession No. BAA24528.1 Jan. 28, 1998.
Genbank Accession No. CAD66648 Feb. 17, 2003.
Genbank Accession No. JC7338 Jun. 3, 2002.
Genbank Accession No. NP010159.1 Jun. 16, 2008.
Genbank Accession No. P41747 May 5, 2009.
Genbank Accession No. Q07551 Nov. 28, 2006.
Goldberg et al., 2007, "Biocatalytic ketone reduction—a powerful tool for the production of chiral alcohols—part I: processes with isolated enzymes," Appl Microbiol Biotechnol, 76(2):237-248.
Gröger et al., 2004, "Preparative asymmetric reduction of ketones in a biphasic medium with an (S)-alcohol dehydrogenase under in situ-cofactor-recycling with a formate dehydrogenase," Tetrahedron 60:633-640.
Hönig et al., 1994, "Enzymatic Resolutions of Heterocyclic Alcohols," Biocatalysis 9:61-69.
Hummel et al., 1989, "Dehydrogenases for the synthesis of chiral compounds," Eur. J. Biochem. 184:1-13.
Hummel, 1990, "Reduction of acetophenone to R(+)-phenylethanol by a new alcohol dehydrogenase from Lactobacillus kefir," Appl Microbiol Biotechnol, 34(1): 15-19.
Hummel, 1999, "Large-scale applications of NAD(P)-dependent oxidoreductases: recent developments," Trends Biotechnol. 17(12):487-492.
Jones et al., 1981, "Enzymes in organic syntheses. 19. Evaluation of the stereoselectivities of horse liver alcohol dehydrogenase; catalyzed oxidoreductions of hydroxyy and ethothiolanes, thianes, and -thiepanes," Can. J. Chem, 49:1574-1579.
Jörnvall et al., 1995, "Short-chain dehydrogenase/reductases (SDR)," Biochemistry 34(18):6003-6013.
Kallberg et al., 2002, "Short-chain dehydrogenase/reductase (SDR) relationships: A large family with eight clusters common to human, animal, and plant genomes," Protein Sci. 11(3):636-641.
Kallberg et al., 2002, "Short-chain dehydrogenases/reductases (SDRs) Coenzyme-based functional assignments in completed genomes," Eur. J. Biochem. 269:4409-4417.
Kitamura et al.. , 1993, "Quantitative Expression of Dynamic Kinetic Resolution of Chrially Labile Enantiomers: Stereoselective Hydrogenation of 2-Substituted 3-Oxo Carboxylic Esters Catalyzed by NINAP-Ruthenium (II) complexes," J Am Chem. Soc. 115:144-152.
Nakamura et al. 2003, "Recent developments in asymmetric reduction of ketones with biocatalysts," Tetrahedron: Asymmetry 14: 2659-2681.
Niefind et al., 2003, "The Crystal Structure of R-specific Alcohol Dehydrogenase from Lactobacillus brevis Suggests the Structural Basis of its Metal Dependency," J Mol Bio. 327(2):317-28.
Noyori et al., 1989, "Stereoselective Hydrogenation via Dynamic Kinetic Resolution," J. Am.Chem. Soc. 111 (25):9134-9135.
PCT International Search Report from PCT/US2008/078046 dated Jan. 13, 2009.
PCT International Search Report from PCT/US2008/078513 dated Feb. 27, 2009.
Petrash et al., 2001, "Functional Genomic Studies of Aldo-keto Reductases," Chem Biol Interact., 130-132 (1-3):673-83.
Rodrigues et al., 2004, "Recent Advances in the Biocatalytic Asymmetric Reduction of Acetophenones and α,β- Unsaturated Carbonyl Compounds," Food Technol. Biotechnol. 42 (4) 295-303.

(56) References Cited

OTHER PUBLICATIONS

Santaniello et al., 1984, "Chiral Synthesis of a Component of Amanita muscaria, (-)-4-hydroxypyrrolidin-2-one, and Assessment of its Absolute Configuration," J. Chem. Res., Synop., 132-133.

Schlieben et al., 2005, "Atomic Resolution Structures of R-specific Alcohol Dehydrogenase from Lactobacillus brevis Provide the Structural Bases of its Substrate and Cosubstrate Specificity," J. Mol. Biol. 349(4):801-13.

Shimoda et al., 2006, "Diastereoselective reduction of β-keto carbonyl compounds by cultured plant cells," Tetrahedron Lett. 47(10):1541-1544.

Temino et al., 2005, "Entrapment of the alcohol dehydrogenase from Lactobacillus kefir in polyvinyl alcohol for the synthesis of chiral hydrophobic alcohols in organic solvents," Enzyme Microb. Technol., 36(1):3-9.

Weckbecker et al., 2006, "Cloning, expression, and characterization of an (R)-specific alcohol dehydrogenase from Lactobacillus kefir," Biocatal. Biotransform., 24(5):380-389.

Wolberg et al., 2000, "Highly Regio- and Enantioselective Reduction of 3,5-Dioxocarboxylates," Angew Chem. Int. Ed. Engl. 39(23):4306-4308.

Wolberg, 2001, "Enzymatic Reduction of Hydrophobic beta, delta-Diketo Esters," Synthesis 937-942.

Xie et al., 2006, "Asymmetric Reduction of o-Chloroacetophenone with Candida pseudotropicalis 104," Biotechnol. Prog. 22:1301-1304.

Zhou et al., 1983, "Stereochemical Control of Yeast Reductions. 1. Asymmetric Synthesis of L-Carnitine," J. Am. Chem., 105:5925-5926.

Zhu et al., 2005, "Evaluation of substituent effects on activity and enantioselectivity in the enzymatic reduction of aryl ketones," Tetrahedron Asymm. 16:1541-1546.

Broun et al., "Catalytic plasticity of fatty acid modification enzymes underlying chemical diversity of plant lipids," Science, 1998, vol. 282:1315-1317.

Devos et al., "Practical limits of function prediction," Proteins:Structure, Function, and Genetics. 2000, vol. 41:98-107.

Seffernick et al., "Melamine deaminase and Atrazine chlorohydrolase: 98 percent identical but functionally different," J. Bacteriol, 2001, vol. 183 (8): 2405-2410.

\* cited by examiner

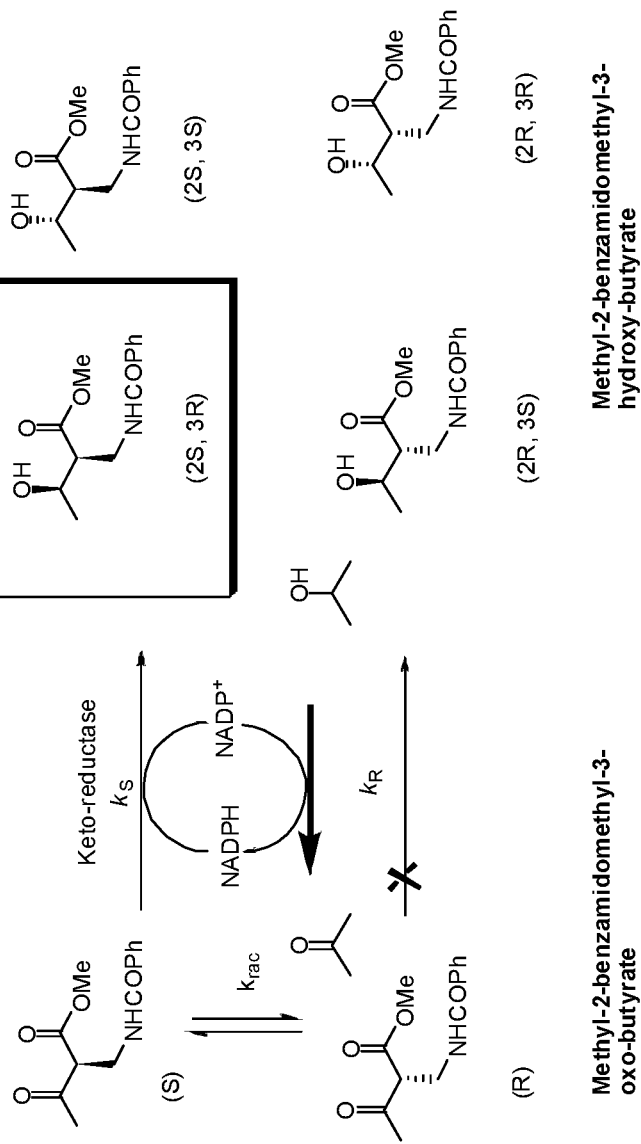

```
                               SEQUENCE LISTING

Sequence total quantity: 87
SEQ ID NO: 1            moltype = DNA   length = 762
FEATURE                 Location/Qualifiers
misc_feature            1..762
                        note = Codon Optimized L. Brevis Sequence
source                  1..762
                        mol_type = other DNA
                        organism = synthetic construct
SEQUENCE: 1
atgtctaacc gtctggatgg caaagtagcc atcattaccg gcgggactct gggtatcggt   60
ttggcaatcg ccacgaaatt tgtagaggag ggtgcgaaaa taatgattac tggtcgtcac  120
tccgatgtag gtgaaaaggc cgccaaatca gtaggcactc cggatcagat tcagtttttt  180
cagcacgatt catccgatga agatggctgg acgaaactgt tcgacgccac cgagaaagca  240
ttcggcccgg ttagcacctt agtgaacaat gcagggattg cagttaacaa aagcgttgaa  300
gaaactacca cggccgaatg gcgtaaactg ctggccgtta atctggatgg tgttttttc   360
ggcacccgtc tgggcattca gcgcatgaaa aataaaggct ggggcgctag catcatcaat  420
atgagcagta ttgaggggtt cgtaggcgat ccgagcctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctgccg  600
ggtgctgagg aagcgatgtc acagcgtacg aaaacccta tgggccacat tggcgaaccg   660
aatgacatcg catatatctg tgtgtacctg gcatctaatg aatcgaaatt tgcgacgggt  720
tccgaatttg tggtcgacgg cgggtatacc gcacagtaat ga                     762

SEQ ID NO: 2            moltype = AA  length = 252
FEATURE                 Location/Qualifiers
REGION                  1..252
                        note = Translation of Codon Optimized L. Brevis Sequence
source                  1..252
                        mol_type = protein
                        organism = synthetic construct
SEQUENCE: 2
MSNRLDGKVA IITGGTLGIG LAIATKFVEE GAKVMITGRH SDVGEKAAKS VGTPDQIQFF   60
QHDSSDEDGW TKLFDATEKA FGPVSTLVNN AGIAVNKSVE ETTTAEWRKL LAVNLDGVFF  120
GTRLGIQRMK NKGLGASIIN MSSIEGFVGD PSLGAYNASK GAVRIMSKSA ALDCALKDYD  180
VRVNTVHPGY IKTPLVDDLP GAEEAMSQRT KTPMGHIGEP NDIAYICVYL ASNESKFATG  240
SEFVVDGGYT AQ                                                      252

SEQ ID NO: 3            moltype = DNA   length = 759
FEATURE                 Location/Qualifiers
misc_feature            1..759
                        note = Codon Optimized L. Kefir Sequence
source                  1..759
                        mol_type = other DNA
                        organism = synthetic construct
SEQUENCE: 3
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatgg tgttttttc   360
ggcacccgtc tgggcattca gcgcatgaaa aataaaggct ggggcgctag catcatcaat  420
atgagcagta ttgaggggtt cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctgaa   600
ggtgctgagg aaatgatgtc acagcgtacg aaaacccta tgggccacat tggcgaaccg   660
aatgacatcg catggatctg tgtgtacctg gcatctgacg aatcgaaatt tgcgacgggt  720
gcagaatttg tggtcgacgg cgggtatacc gcacagtga                         759

SEQ ID NO: 4            moltype = AA  length = 252
FEATURE                 Location/Qualifiers
REGION                  1..252
                        note = Translation of Codon Optimized L. kefir Sequence
source                  1..252
                        mol_type = protein
                        organism = synthetic construct
SEQUENCE: 4
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWRKL LSVNLDGVFF  120
GTRLGIQRMK NKGLGASIIN MSSIEGFVGD PTLGAYNASK GAVRIMSKSA ALDCALKDYD  180
VRVNTVHPGY IKTPLVDDLE GAEEMMSQRT KTPMGHIGEP NDIAWICVYL ASDESKFATG  240
AEFVVDGGYT AQ                                                      252
```

```
SEQ ID NO: 5              moltype = DNA  length = 759
FEATURE                   Location/Qualifiers
misc_feature              1..759
                          note = variant of L. kefir
source                    1..759
                          mol_type = other DNA
                          organism = synthetic construct
SEQUENCE: 5
atgaccgatc gtctgaaggg caaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttagcaa aagcgttgaa  300
gacactacca cggaggaatg gcgtaaactg ctgtccgtta atctggatgg tgttttttc   360
ggcacccgtc tgggcattca gcgcatgaaa aataaaggct tgggcgctag catcatcaat  420
atgagcagta ttgaggggct ggtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatcatgaa  600
ggtctggagg aaatgatgtc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                         759

SEQ ID NO: 6              moltype = AA  length = 252
FEATURE                   Location/Qualifiers
REGION                    1..252
                          note = variant of L. kefir
source                    1..252
                          mol_type = protein
                          organism = synthetic construct
SEQUENCE: 6
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGLVGD PTLGAYNASK GAVRIMSKSA ALDCALKDYD   180
VRVNTVHPGY IKTPLVDDHE GLEEMMSQRT KTPMGHIGEP NDIAWICVYL ASDESKFATG   240
AEFVVDGGYT AQ                                                      252

SEQ ID NO: 7              moltype = DNA  length = 759
FEATURE                   Location/Qualifiers
misc_feature              1..759
                          note = variant of L. kefir
source                    1..759
                          mol_type = other DNA
                          organism = synthetic construct
SEQUENCE: 7
atgaccgatc gtctgaaggg caaagtagcc atcgtaaccg gcgggacact gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttagcaa aagcgttgaa  300
gacactacca cggaggaatg gcgtaaactg ctgtccgtta atctggatgg tgttttttc   360
ggcacccgtc tgggcattca gcgcatgaaa aataaaggct tgggcgctag catcatcaat  420
atgagcagta ttgaggggtt cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatcatgaa  600
ggtctggagg aaatgatgtc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                         759

SEQ ID NO: 8              moltype = AA  length = 252
FEATURE                   Location/Qualifiers
REGION                    1..252
                          note = variant of L. kefir
source                    1..252
                          mol_type = protein
                          organism = synthetic construct
SEQUENCE: 8
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDHE GLEEMMSQRT KTPMGHIGEP NDIAWICVYL ASDESKFATG   240
AEFVVDGGYT AQ                                                      252

SEQ ID NO: 9              moltype = DNA  length = 759
FEATURE                   Location/Qualifiers
misc_feature              1..759
                          note = variant of L. kefir
source                    1..759
                          mol_type = other DNA
                          organism = synthetic construct
```

```
SEQUENCE: 9
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgc   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttgaggggct ggtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatcatgaa   600
ggtctggagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 10           moltype = AA   length = 252
FEATURE                 Location/Qualifiers
REGION                  1..252
                        note = variant of L. kefir
source                  1..252
                        mol_type = protein
                        organism = synthetic construct
SEQUENCE: 10
MTDRLKGKVA IVTGGTLGIG LAIADKFVEE GAKVVITGRR ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGLVGD PTLGAYNASK GAVRIMSKSA ALDCALKDYD   180
VRVNTVHPGY IKTPLVDDHE GLEEMMSQRT KTPMGHIGEP NDIAWICVYL ASDESKFATG   240
AEFVVDGGYT AQ                                                      252

SEQ ID NO: 11           moltype = DNA   length = 759
FEATURE                 Location/Qualifiers
misc_feature            1..759
                        note = variant of L. kefir
source                  1..759
                        mol_type = other DNA
                        organism = synthetic construct
SEQUENCE: 11
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgc   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatcatgaa   600
ggtctggagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 12           moltype = AA   length = 252
FEATURE                 Location/Qualifiers
REGION                  1..252
                        note = variant of L. kefir
source                  1..252
                        mol_type = protein
                        organism = synthetic construct
SEQUENCE: 12
MTDRLKGKVA IVTGGTLGIG LAIADKFVEE GAKVVITGRR ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDHE GLEEMMSQRT KTPMGHIGEP NDIAWICVYL ASDESKFATG   240
AEFVVDGGYT AQ                                                      252

SEQ ID NO: 13           moltype = DNA   length = 759
FEATURE                 Location/Qualifiers
misc_feature            1..759
                        note = variant of L. kefir
source                  1..759
                        mol_type = other DNA
                        organism = synthetic construct
SEQUENCE: 13
atgaccgatc gtctgaaggg caaagtagcc atcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattt tgttgttaa aagcgttgaa   300
gacactacca cggaggaatg gcgtaaactg ctgtccgtta atctggatgg tgttttttc   360
```

```
ggcacccgtc tgggcattca gcgcatgaaa aataaaggct tgggcgctag catcatcaat    420
atgagcagta ttgaagggat ggtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cggtgctcga tgattgggaa    600
ggtgctgagg aaatgatgtc acagcgtacg aaaaccccta tgggccacat tggtgaaccg    660
aatgacatcg catgggtctg tgtgtacctg gcatctgatg aatcgaaatt tgcgacgggt    720
gcagaatttg tggtcgacgg cgggtggacc gcacagtga                           759

SEQ ID NO: 14             moltype = AA   length = 252
FEATURE                   Location/Qualifiers
REGION                    1..252
                          note = variant of L. kefir
source                    1..252
                          mol_type = protein
                          organism = synthetic construct
SEQUENCE: 14
MTDRLKGKVA IVTGGTLGIG LAIADKFVEE GAKVVITGRR ADVGEKAAKS IGGTDVIRFV     60
QHDASDEAGW TKLFDTTEEA FGPVTTVVNN AGIFVVKSVE DTTTEEWRKL LSVNLDGVFF    120
GTRLGIQRMK NKGLGASIIN MSSIEGMVGD PTLGAYNASK GAVRIMSKSA ALDCALKDYD    180
VRVNTVHPGY IKTPVLDDWE GAEEMMSQRT KTPMGHIGEP NDIAWVCVYL ASDESKFATG    240
AEFVVDGGWT AQ                                                       252

SEQ ID NO: 15             moltype = DNA   length = 759
FEATURE                   Location/Qualifiers
misc_feature              1..759
                          note = variant of L. kefir
source                    1..759
                          mol_type = other DNA
                          organism = synthetic construct
SEQUENCE: 15
atgaccgatc gtctgaaggg caaagtagcc atcgtaaccg gcgggactct gggtatcggt     60
ttggcaatcg ccgataaatt tgtagaggag ggtgcgaaag tagttattac tggtcgtcac    120
gcggatgtag cgaaaaggc cgccaaatca atcggcggca ctgatgttat tcgctttgtc    180
cagcacgatg catccgatga agcaggctgg acgaaactgt tcgacaccac cgaggaggca    240
ttcggcccgg ttacgaccgt cgtgaacaat gcagggatta ccgttttaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat    420
atgagcagta ttgagggttc gtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tatctggaa    600
ggtgtggagg aaatgatgtc acagcgtacg aaaaccccta tgggccacat tggtgaaccg    660
aatgacatcg catggatctg tgtgtacctg gcatctgacg aatcgaaatt tgcgacgggt    720
gcagaatttg tggtcgacgg cgggtatacc gcacagtga                           759

SEQ ID NO: 16             moltype = AA   length = 252
FEATURE                   Location/Qualifiers
REGION                    1..252
                          note = variant of L. kefir
source                    1..252
                          mol_type = protein
                          organism = synthetic construct
SEQUENCE: 16
MTDRLKGKVA IVTGGTLGIG LAIADKFVEE GAKVVITGRH ADVGEKAAKS IGGTDVIRFV     60
QHDASDEAGW TKLFDTTEEA FGPVTTVVNN AGITVFKSVE DTTTEEWRKL LSVNLDGVFF    120
GTRLGIQRMK NKGLGASIIN MSSIEGFVGD PTLGAYNASK GAVRIMSKSA ALDCALKDYD    180
VRVNTVHPGY IKTPLVDDLE GVEEMMSQRT KTPMGHIGEP NDIAWICVYL ASDESKFATG    240
AEFVVDGGYT AQ                                                       252

SEQ ID NO: 17             moltype = DNA   length = 759
FEATURE                   Location/Qualifiers
misc_feature              1..759
                          note = variant of L. kefir
source                    1..759
                          mol_type = other DNA
                          organism = synthetic construct
SEQUENCE: 17
atgaccgatc gtctgaaggg caaagtagcc atcgtaaccg gcgggactct gggtatcggt     60
ttggcaatcg ccgataaatt tgtagaggag ggtgcgaaag tagttattac tggtcgtcac    120
gcggatgtag cgaaaaggc cgccaaatca atcggcggca ctgatgttat tcgctttgtc    180
cagcacgatg catccgatga agcaggctgg acgaaactgt tcgacaccac cgaggagaca    240
ttcggcccgg ttacgaccgt cgtgaacaat gcagggattg ccgttagcaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat    420
atgagcagta ttgagggcag cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tatctggaa    600
ggtgtggagg aaatgatgtc acagcgtacg aaaaccccta tgggccacat tggtgaaccg    660
aatgacatcg catggatctg tgtgtacctg gcatctgacg aatcgaaatt tgcgacgggt    720
gcagaatttg tggtcgacgg cgggtatacc gcacagtga                           759
```

```
SEQ ID NO: 18           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 18
MTDRLKGKVA IVTGGTLGIG LAIADKFVEE GAKVVITGRH ADVGEKAAKS IGGTDVIRFV    60
QHDASDEAGW TKLFDTTEET FGPVTTVVNN AGIAVSKSVE DTTTEEWRKL LSVNLDGVFF   120
GTRLGIQRMK NKGLGASIIN MSSIEGFVGD PTAGAYNASK GAVRIMSKSA ALDCALKDYD   180
VRVNTVHPGY IKTPLVDDLE GVEEMMSQRT KTPMGHIGEP NDIAWICVYL ASDESKFATG   240
AEFVVDGGYT AQ                                                       252

SEQ ID NO: 19           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 19
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggta ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta atctggatgg tgttttttc   360
ggcacccgtc tgggcattca gcgcatgaaa aataaagcgt tgggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgataatgaa   600
ggtgtggagg aaatgatgtc acagcgtacg aaaaccccta gggcacacat tggtgaaccg   660
aatgacatcg catggatctg tgtgtacctg gcatctgacg aatcgaaatt tgcgacgggt   720
gcagaatttg tggtcgacgg cgggtatacc gcacagtga                         759

SEQ ID NO: 20           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 20
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDNE GVEEMMSQRT KTPMGHIGEP NDIAWICVYL ASDESKFATG   240
AEFVVDGGYT AQ                                                       252

SEQ ID NO: 21           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 21
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta atctggatgg tgttttttc   360
ggcacccgtc tgggcattca gcgcatgaaa aataaaggct tgggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatcatgaa   600
ggtctggagg aaatgatgtc acagcgtacg aaaaccccta gggccacat tggtgaaccg    660
aatgacatcg catggatctg tgtgtacctg gcatctgacg aatcgaaatt tgcgacgggt   720
gcagaatttg tggtcgacgg cgggtatacc gcacagtga                         759

SEQ ID NO: 22           moltype = AA  length = 252
FEATURE                 Location/Qualifiers
REGION                  1..252
                        note = variant of L. kefir
source                  1..252
                        mol_type = protein
```

```
                        organism = synthetic construct
SEQUENCE: 22
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDHE GLEEMMSQRT KTPMGHIGEP NDIAWICVYL ASDESKFATG   240
AEFVVDGGYT AQ                                                      252

SEQ ID NO: 23           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 23
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta tctggatgg tgtttttttc   360
ggcacccgtc tgggcattca gcgcatgaaa aataaaggct gggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccggggtat atcaagaccc cgctggtcga tgatcatgaa   600
ggtgtggagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                         759

SEQ ID NO: 24           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 24
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDHE GVEEMMSQRT KTPMGHIGEP NDIAWICVYL ASDESKFATG   240
AEFVVDGGYT AQ                                                      252

SEQ ID NO: 25           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 25
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta tctggatgg tgtttttttc   360
ggcacccgtc tgggcattca gcgcatgaaa aataaaggct gggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccggggtat atcaagaccc cgctggtcga tgatctggaa   600
ggtctggagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                         759

SEQ ID NO: 26           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 26
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDLE GLEEMMSQRT KTPMGHIGEP NDIAWICVYL ASDESKFATG   240
AEFVVDGGYT AQ                                                      252
```

```
SEQ ID NO: 27              moltype = DNA  length = 759
FEATURE                    Location/Qualifiers
misc_feature               1..759
                           note = variant of L. kefir
source                     1..759
                           mol_type = other DNA
                           organism = synthetic construct
SEQUENCE: 27
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttagcaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta ttgaggggtt cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tctggaa    600
ggtgtggagg aaatgatgtc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                         759

SEQ ID NO: 28              moltype = AA  length = 252
FEATURE                    Location/Qualifiers
REGION                     1..252
                           note = variant of L. kefir
source                     1..252
                           mol_type = protein
                           organism = synthetic construct
SEQUENCE: 28
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGITVSKSVE DTTTEEWRKL LSVNLDGVFF  120
GTRLGIQRMK NKGLGASIIN MSSIEGFVGD PTLGAYNASK GAVRIMSKSA ALDCALKDYD  180
VRVNTVHPGY IKTPLVDDLE GVEEMMSQRT KTPMGHIGEP NDIAWICVYL ASDESKFATG  240
AEFVVDGGYT AQ                                                      252

SEQ ID NO: 29              moltype = DNA  length = 759
FEATURE                    Location/Qualifiers
misc_feature               1..759
                           note = variant of L. kefir
source                     1..759
                           mol_type = other DNA
                           organism = synthetic construct
SEQUENCE: 29
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttagcaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta ttgaggggtt cgtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgcagaa    600
ggtctggagg aaatgatgtc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                         759

SEQ ID NO: 30              moltype = AA  length = 252
FEATURE                    Location/Qualifiers
REGION                     1..252
                           note = variant of L. kefir
source                     1..252
                           mol_type = protein
                           organism = synthetic construct
SEQUENCE: 30
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGITVSKSVE DTTTEEWRKL LSVNLDGVFF  120
GTRLGIQRMK NKGLGASIIN MSSIEGFVGD PTLGAYNASK GAVRIMSKSA ALDCALKDYD  180
VRVNTVHPGY IKTPLVDDAE GLEEMMSQRT KTPMGHIGEP NDIAWICVYL ASDESKFATG  240
AEFVVDGGYT AQ                                                      252

SEQ ID NO: 31              moltype = DNA  length = 759
FEATURE                    Location/Qualifiers
misc_feature               1..759
                           note = variant of L. kefir
source                     1..759
                           mol_type = other DNA
```

```
                                organism = synthetic construct
SEQUENCE: 31
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatgcagaa   600
ggtgtggagg aaatgatgtc acagcgtacg aaaaacccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 32              moltype = AA  length = 252
FEATURE                    Location/Qualifiers
REGION                     1..252
                           note = variant of L. kefir
source                     1..252
                           mol_type = protein
                           organism = synthetic construct
SEQUENCE: 32
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDAE GVEEMMSQRT KTPMGHIGEP NDIAWICVYL ASDESKFATG   240
AEFVVDGGYT AQ                                                       252

SEQ ID NO: 33              moltype = DNA  length = 759
FEATURE                    Location/Qualifiers
misc_feature               1..759
                           note = variant of L. kefir
source                     1..759
                           mol_type = other DNA
                           organism = synthetic construct
SEQUENCE: 33
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttgaggggtt cgtaggcgat ccgacgcag gggcatacaa cgcttccaag    480
ggggcggtac gtatcatgtc gaaaagcgca gcgctggatt gcgcactgaa ggactacgat   540
gtgcgtgtca acacagtaca tccgggctat atcaagaccc cgctggtcga tcatgaa      600
ggtctggagg aaatgatgtc acagcgtacg aaaaacccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 34              moltype = AA  length = 252
FEATURE                    Location/Qualifiers
REGION                     1..252
                           note = variant of L. kefir
source                     1..252
                           mol_type = protein
                           organism = synthetic construct
SEQUENCE: 34
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVSKSVE DTTTEEWRKL LSVNLDGVFF   120
GTRLGIQRMK NKGLGASIIN MSSIEGFVGD PTAGAYNASK GAVRIMSKSA ALDCALKDYD   180
VRVNTVHPGY IKTPLVDDHE GLEEMMSQRT KTPMGHIGEP NDIAWICVYL ASDESKFATG   240
AEFVVDGGYT AQ                                                       252

SEQ ID NO: 35              moltype = DNA  length = 759
FEATURE                    Location/Qualifiers
misc_feature               1..759
                           note = variant of L. kefir
source                     1..759
                           mol_type = other DNA
                           organism = synthetic construct
SEQUENCE: 35
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggatta ccgttagcaa aagcgttgaa   300
```

```
gacactacca cggaggaatg gcgtaaactc ctgtccgtta atctggatgg tgttttttc    360
ggcacccgtc tgggcattca gcgcatgaaa aataaaggct tgggcgctag catcatcaat  420
atgagcagta ttgaggggtt cgtaggcgat ccgacggcag gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga cgatgcagaa  600
ggtgtagagg aaatgatgtc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                         759

SEQ ID NO: 36           moltype = AA   length = 252
FEATURE                 Location/Qualifiers
REGION                  1..252
                        note = variant of L. kefir
source                  1..252
                        mol_type = protein
                        organism = synthetic construct
SEQUENCE: 36
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGITVSKSVE DTTTEEWRKL LSVNLDGVFF  120
GTRLGIQRMK NKGLGASIIN MSSIEGFVGD PTAGAYNASK GAVRIMSKSA ALDCALKDYD  180
VRVNTVHPGY IKTPLVDDAE GVEEMMSQRT KTPMGHIGEP NDIAWICVYL ASDESKFATG  240
AEFVVDGGYT AQ                                                      252

SEQ ID NO: 37           moltype = DNA   length = 759
FEATURE                 Location/Qualifiers
misc_feature            1..759
                        note = variant of L. kefir
source                  1..759
                        mol_type = other DNA
                        organism = synthetic construct
SEQUENCE: 37
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcaggggatta ccgttagcaa aagcgttgaa  300
gacactacca cgggggaatg gcgtaaactc ctgtccgtta atctggatgg tgttttttc   360
ggcacccgtc tgggcattca gcgcatgaaa aataaaggct tgggcgctag catcatcaat  420
atgagcagta ttgaggggtt cgtaggcgat ccgacggcag gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc gctggtcga tgatgcagaa  600
ggtctggagg aaatgttttc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                         759

SEQ ID NO: 38           moltype = AA   length = 252
FEATURE                 Location/Qualifiers
REGION                  1..252
                        note = variant of L. kefir
source                  1..252
                        mol_type = protein
                        organism = synthetic construct
SEQUENCE: 38
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGITVSKSVE DTTTGEWRKL LSVNLDGVFF  120
GTRLGIQRMK NKGLGASIIN MSSIEGFVGD PTAGAYNASK GAVRIMSKSA ALDCALKDYD  180
VRVNTVHPGY IKTPLVDDAE GLEEMFSQRT KTPMGHIGEP NDIAWICVYL ASDESKFATG  240
AEFVVDGGYT AQ                                                      252

SEQ ID NO: 39           moltype = DNA   length = 759
FEATURE                 Location/Qualifiers
misc_feature            1..759
                        note = variant of L. kefir
source                  1..759
                        mol_type = other DNA
                        organism = synthetic construct
SEQUENCE: 39
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggatta ccgttttaa aagcgttgaa   300
gacactacca cggaggaatg gcgtaaactc ctgtccgtta atctggatgg tgttttttc   360
ggcacccgtc tgggcattca gcgcacgaaa aataaaggct tgggcgctag catcatcaat  420
atgagcagta ttgaggggtt cgtaggcgat ccgacgctgg ggcatacaa cgcttccaag   480
ggggcggtac gtatcatgtc gaaaagcgca gcgctggatt gcgcactgaa ggactacgat  540
gtgcgtgtca acacagtaca tccgggctat atcaagaccc gctggtcga tgatctgaa   600
ggtgtggagg aaatgttttc acagcgtacg aaaaccccta tgggccacat tggtgaaccg  660
aatgacatcg catggatctg tgtgtacctg gcatctgacg aatcgaaatt tgcgacgggt  720
```

```
gcagaatttg tggtcgacgg cgggtatacc gcacagtga                         759

SEQ ID NO: 40              moltype = AA   length = 252
FEATURE                    Location/Qualifiers
REGION                     1..252
                           note = variant of L. kefir
source                     1..252
                           mol_type = protein
                           organism = synthetic construct
SEQUENCE: 40
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGITVFKSVE DTTTEEWRKL LSVNLDGVFF   120
GTRLGIQRTK NKGLGASIIN MSSIEGFVGD PTLGAYNASK GAVRIMSKSA ALDCALKDYD   180
VRVNTVHPGY IKTPLVDDLE GVEEMFSQRT KTPMGHIGEP NDIAWICVYL ASDESKFATG   240
AEFVVDGGYT AQ                                                      252

SEQ ID NO: 41              moltype = DNA   length = 759
FEATURE                    Location/Qualifiers
misc_feature               1..759
                           note = variant of L. kefir
source                     1..759
                           mol_type = other DNA
                           organism = synthetic construct
SEQUENCE: 41
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa agcgttgaa    300
gacactacca cggaggaatg gcgtaaactg ctgtccgtta atctggatgg tgttttttc    360
ggcacccgtc tgggcatcca gcgcatgaaa aataaaggct gggcgctag catcatcaat    420
atgagcagta ttgaggggtt cgtaggcgat ccgacggcag ggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgataatgaa    600
ggtctggagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                         759

SEQ ID NO: 42              moltype = AA   length = 252
FEATURE                    Location/Qualifiers
REGION                     1..252
                           note = variant of L. kefir
source                     1..252
                           mol_type = protein
                           organism = synthetic construct
SEQUENCE: 42
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTAGAYNASK GAVRIMSKSA ALDCALKDYD   180
VRVNTVHPGY IKTPLVDDNE GLEEMMSQRT KTPMGHIGEP NDIAWICVYL ASDESKFATG   240
AEFVVDGGYT AQ                                                      252

SEQ ID NO: 43              moltype = DNA   length = 759
FEATURE                    Location/Qualifiers
misc_feature               1..759
                           note = variant of L. kefir
source                     1..759
                           mol_type = other DNA
                           organism = synthetic construct
SEQUENCE: 43
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa agcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat    420
atgagcagta ttgaagggat ggtaggcgat ccgacgctgg ggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgatctggaa    600
ggtgtagagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                         759

SEQ ID NO: 44              moltype = AA   length = 252
FEATURE                    Location/Qualifiers
REGION                     1..252
                           note = variant of L. kefir
source                     1..252
```

-continued

```
                         mol_type = protein
                         organism = synthetic construct
SEQUENCE: 44
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSKS DTTTEEWRKL LSVNLDGVFF   120
GTRLGIQRMK NKGLGASIIN MSSIEGMVGD PTLGAYNASK GAVRIMSKSA ALDCALKDYD   180
VRVNTVHPGY IKTPLVDDLE GVEEMMSQRT KTPMGHIGEP NDIAWICVYL ASDESKFATG   240
AEFVVDGGYT AQ                                                      252

SEQ ID NO: 45           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 45
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttgaggggtt cgtaggcgat ccgacgagcg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtctggagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 46           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 46
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTSGAYNASK GAVRIMSKSA ALDCALKDYD   180
VRVNTVHPGY IKTPLVDDLE GLEEMMSQRT KTPMGHIGEP NDIAWICVYL ASDESKFATG   240
AEFVVDGGYT AQ                                                      252

SEQ ID NO: 47           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 47
atgaccgatc gtctgaaggg caaagtagcc atcgtaaccg gcgggactct gggtatcggt    60
ttggcaatcg ccgataaatt tgtagaggag ggtgcgaaag tagttattac tggtcgtcac   120
gcggatgtag gtgaaaaggc cgccaaatca atcggcggca ctgatgttat tcgctttgtc   180
cagcacgatg catccgatga agcaggctgg acgaaactgt tcgacaccac cgaggaggca   240
ttcggcccgg ttacgaccgt cgtgaacaat gcagggattg cagtttccaa aagcgttgaa   300
gacactacca cggaggaatg gcgtaaactg ctgtccgtta atctggatgg tgttttttc   360
ggcacccgtc tgggcattca gcgcatgaaa aataaaggct gggcgctag catcatcaat   420
atgagcagta ttgaggggtt cgtaggcgat ccgacgctgg gggcatacaa cgcttccaag   480
ggggcggtac gtatcatgtc gaaaagcgca gcgctggatt gcgcactgaa ggactacgat   540
gtgcgtgtca acacagtaca tccgggctat atcaagaccc cgctggtcga tgatctggaa   600
ggtgtagagg aaatgatgtc acagcgtacg aaaaccccta tgggccacat tggtgaaccg   660
aatgacatcg catggatctg tgtgtacctg gcatctgacg aatcgaaatt tgcgacgggt   720
gcagaatttg tggtcgacgg cgggtatacc gcacagtga                          759

SEQ ID NO: 48           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 48
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTLGAYNASK GAVRIMSKSA ALDCALKDYD   180
VRVNTVHPGY IKTPLVDDLE GVEEMMSQRT KTPMGHIGEP NDIAWICVYL ASDESKFATG   240
```

```
AEFVVDGGYT AQ                                                                    252

SEQ ID NO: 49              moltype = DNA  length = 759
FEATURE                    Location/Qualifiers
misc_feature               1..759
                           note = variant of L. kefir
source                     1..759
                           mol_type = other DNA
                           organism = synthetic construct
SEQUENCE: 49
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta ttgaggggtt cgtaggcgat ccgacggcag gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatcatgaa  600
ggtctggagg aaatgatgtc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                        759

SEQ ID NO: 50              moltype = AA  length = 252
FEATURE                    Location/Qualifiers
REGION                     1..252
                           note = variant of L. kefir
source                     1..252
                           mol_type = protein
                           organism = synthetic construct
SEQUENCE: 50
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWRKL LSVNLDGVFF  120
GTRLGIQRMK NKGLGASIIN MSSIEGFVGD PTAGAYNASK GAVRIMSKSA ALDCALKDYD  180
VRVNTVHPGY IKTPLVDDHE GLEEMMSQRT KTPMGHIGEP NDIAWICVYL ASDESKFATG  240
AEFVVDGGYT AQ                                                     252

SEQ ID NO: 51              moltype = DNA  length = 759
FEATURE                    Location/Qualifiers
misc_feature               1..759
                           note = variant of L. kefir
source                     1..759
                           mol_type = other DNA
                           organism = synthetic construct
SEQUENCE: 51
atgaccgatc gtctgaaggg caaagtagcc atcgtaaccg gcgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta ttgaggggtt cgtaggcgat ccgacggcag gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtctggagg aaatgatgtc acagcgtacg aaaaccccta tgggccacat tggtgaaccg  660
aatgacatcg catggatctg tgtgtacctg gcatctgacg aatcgaaatt tgcgacgggt  720
gcagaatttg tggtcgacgg cgggtatacc gcacagtga                        759

SEQ ID NO: 52              moltype = AA  length = 252
FEATURE                    Location/Qualifiers
REGION                     1..252
                           note = variant of L. kefir
source                     1..252
                           mol_type = protein
                           organism = synthetic construct
SEQUENCE: 52
MTDRLKGKVA IVTGGTLGIG LAIADKFVEE GAKVVITGRH ADVGEKAAKS IGGTDVIRFV   60
QHDASDEAGW TKLFDTTEEA FGPVTTVVNN AGIAVSKSVE DTTTEEWRKL LSVNLDGVFF  120
GTRLGIQRMK NKGLGASIIN MSSIEGFVGD PTAGAYNASK GAVRIMSKSA ALDCALKDYD  180
VRVNTVHPGY IKTPLVDDLE GLEEMMSQRT KTPMGHIGEP NDIAWICVYL ASDESKFATG  240
AEFVVDGGYT AQ                                                     252

SEQ ID NO: 53              moltype = DNA  length = 759
FEATURE                    Location/Qualifiers
misc_feature               1..759
                           note = variant of L. kefir
source                     1..759
```

```
                    mol_type = other DNA
                    organism = synthetic construct
SEQUENCE: 53
atgaccgatc gtctgaaggg caaagtagcc atcgtaaccg cgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatgg tgttttttc   360
ggcacccgtc tgggcattca gcgcatgaaa aataaaggct tgggcgctag catcatcaat  420
atgagcagta ttgaggggtt cgtaggcgat ccgacggcag gggcataca cgcttccaag   480
ggggcggtac gtatcatgtc gaaaagcgca gcgctggatt gcgcactgaa ggactacgat  540
gtgcgtgtca acacagtaca tccgggctat atcaagaccc cgctggtcga tgatctggaa  600
ggtgtagagg aaatgatgtc acagcgtacg aaaaacccca tggtgcacat tggtgaaccg  660
aatgacatcg catggatctg tgtgtacctg gcatctgacg aatcgaaatt tgcgacgggt  720
gcagaatttg tggtcgacgg cgggtatacc gcacagtga                        759

SEQ ID NO: 54        moltype = AA    length = 252
FEATURE              Location/Qualifiers
REGION               1..252
                     note = variant of L. kefir
source               1..252
                     mol_type = protein
                     organism = synthetic construct
SEQUENCE: 54
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTAGAYNASK GAVRIMSKSA ALDCALKDYD   180
VRVNTVHPGY IKTPLVDDLE GVEEMMSQRT KTPMGHIGEP NDIAWICVYL ASDESKFATG   240
AEFVVDGGYT AQ                                                       252

SEQ ID NO: 55        moltype = DNA   length = 759
FEATURE              Location/Qualifiers
misc_feature         1..759
                     note = variant of L. kefir
source               1..759
                     mol_type = other DNA
                     organism = synthetic construct
SEQUENCE: 55
atgaccgatc gtctgaaggg caaagtagcc atcgtaaccg cgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
ttcggcccgg ttacgaccgt cgtgaacaat gcagggattg cagtttccaa aagcgttgaa  300
gacactacca cggaggaatg gcgtaaactg ctgtccgtta atctggatgg tgttttttc   360
ggcacccgtc tgggcattca gcgcatgaaa aataaaggct tgggcgctag catcatcaat  420
atgagcagta ttgaggggtt cgtaggcgat ccgacggcag gggcataca cgcttccaag   480
ggggcggtac gtatcatgtc gaaaagcgca gcgctggatt gcgcactgaa ggactacgat  540
gtgcgtgtca acacagtaca tccgggctat atcaagaccc cgctggtcga tgatgcagaa  600
ggtctggagg aaatgatgtc acagcgtacg aaaaacccta tgggcacat tggtgaaccg   660
aatgacatcg catggatctg tgtgtacctg gcatctgacg aatcgaaatt tgcgacgggt  720
gcagaatttg tggtcgacgg cgggtatacc gcacagtga                        759

SEQ ID NO: 56        moltype = AA    length = 252
FEATURE              Location/Qualifiers
REGION               1..252
                     note = variant of L. kefir
source               1..252
                     mol_type = protein
                     organism = synthetic construct
SEQUENCE: 56
MTDRLKGKVA IVTGGTLGIG LAIADKFVEE GAKVVITGRH ADVGEKAAKS IGGTDVIRFV    60
QHDASDEAGW TKLFDTTEEA FGPVTTVVNN AGIAVSKSVE DTTTEEWRKL LSVNLDGVFF   120
GTRLGIQRMK NKGLGASIIN MSSIEGFVGD PTAGAYNASK GAVRIMSKSA ALDCALKDYD   180
VRVNTVHPGY IKTPLVDDAE GLEEMMSQRT KTPMGHIGEP NDIAWICVYL ASDESKFATG   240
AEFVVDGGYT AQ                                                       252

SEQ ID NO: 57        moltype = DNA   length = 759
FEATURE              Location/Qualifiers
misc_feature         1..759
                     note = variant of L. kefir
source               1..759
                     mol_type = other DNA
                     organism = synthetic construct
SEQUENCE: 57
atgaccgatc gtctgaaggg caaagtagcc atcgtaaccg cgggactct gggtatcggt   60
ttggcaatcg ccgataaatt tgtagaggag ggtgcgaaag tagttattac tggtcgtcac  120
gcggatgtag gtgaaaaggc cgccaaatca atcggcggca ctgatgttat tcgctttgtc  180
cagcacgatg catccgatga agcaggctgg acgaaactgt tcgacaccac cgaggaggca  240
```

```
ttcggcccgg ttacgatcgt cgtgaacaat gcagggattg cagttttccaa aagcgttgaa    300
gacactacca cggaggaatg gcgtaaaactg ctgtccgtta atctggatgg tgttttttc    360
ggcacccgtc tgggcattca gcgcatgaaa aataaaggct tgggcgctag catcatcaat    420
atgagcagta ttgaggggtt cgtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggctat atcaagaccc cgctggtcga tgataatgaa    600
ggtctggagg aaatgatgtc acagcgtacg aaaaccccta tgggccacat tggtgaaccg    660
aatgacatcg catggatctg tgtgtacctg gcatctgacg aatcgaaatt tgcgacgggt    720
gcagaatttg tggtcgacgg cgggtatacc gcacagtga                            759
```

| SEQ ID NO: 58 | moltype = AA length = 252 |
|---|---|
| FEATURE | Location/Qualifiers |
| REGION | 1..252 |
| | note = variant of L. kefir |
| source | 1..252 |
| | mol_type = protein |
| | organism = synthetic construct |

SEQUENCE: 58
```
MTDRLKGKVA IVTGGTLGIG LAIADKFVEE GAKVVITGRH ADVGEKAAKS IGGTDVIRFV     60
QHDASDEAGW TKLFDTTEEA FGPVTIVVNN AGIAVSKSVE DTTTEEWRKL LSVNLDGVFF    120
GTRLGIQRMK NKGLGASIIN MSSIEGFVGD PTLGAYNASK GAVRIMSKSA ALDCALKDYD    180
VRVNTVHPGY IKTPLVDDNE GLEEMMSQRT KTPMGHIGEP NDIAWICVYL ASDESKFATG    240
AEFVVDGGYT AQ                                                        252
```

| SEQ ID NO: 59 | moltype = DNA length = 759 |
|---|---|
| FEATURE | Location/Qualifiers |
| misc_feature | 1..759 |
| | note = variant of L. kefir |
| source | 1..759 |
| | mol_type = other DNA |
| | organism = synthetic construct |

SEQUENCE: 59
```
atgaccgatc gtctgaaggg caaagtagcc ttcgtaaccg gcgggacact gggtatcggt     60
ttggcaatcg ccgataaatt tgtagaggag ggtgcgcggg tagttattac tggtcgtcgt    120
gcggatgtag gtgaaaaggc cgccaaatca atcggcggca ctgatgttat tcgcttttgtc   180
cagcacgatg cgtccgatga agcaggctgg acgaaactgt tcgacaccac cgaggaggca    240
ttcggcccgg ttacgaccgt cgtgaacaat gcagggattt tgttgttaa aagcgttgaa    300
gacactacca cggaggaatg gcgtaaaactg ctgtccgtta atctggatgg tgttttttc    360
ggcacccgtc tgggcattca gcgcatgaaa aataaaggct tgggcgctag catcatcaat    420
atgagcagta ttgaagggat ggtaggcgat ccgacgctgg gggcatacaa cgcttccaag    480
ggggcggtac gtatcatgtc gaaagcgca gcgctggatt gcgcactgaa ggactacgat    540
gtgcgtgtca acacagtaca tccgggctat atcaagaccc cggtgctcga tgattgggaa    600
ggtctggagg aaatgatgtc acagcgtacg aaaaccccta tgggccacat tggtgaaccg    660
aatgacatcg catgggtctg tgtgtacctg gcatctgatg aatcgaaatt tgcgacgggt    720
gcagaatttg tggtcgacgg caagtggacc gcacagtga                           759
```

| SEQ ID NO: 60 | moltype = AA length = 252 |
|---|---|
| FEATURE | Location/Qualifiers |
| REGION | 1..252 |
| | note = variant of L. kefir |
| source | 1..252 |
| | mol_type = protein |
| | organism = synthetic construct |

SEQUENCE: 60
```
MTDRLKGKVA FVTGGTLGIG LAIADKFVEE GAKVVITGRR ADVGEKAAKS IGGTDVIRFV     60
QHDASDEAGW TKLFDTTEEA FGPVTTVVNN AGIFVVKSVE DTTTEEWRKL LSVNLDGVFF    120
GTRLGIQRMK NKGLGASIIN MSSIEGMVGD PTLGAYNASK GAVRIMSKSA ALDCALKDYD    180
VRVNTVHPGY IKTPVLDDWE GAEEMMSQRT KTPMGHIGEP NDIAWVCVYL ASDESKFATG    240
AEFVVDGKWT AQ                                                        252
```

| SEQ ID NO: 61 | moltype = DNA length = 759 |
|---|---|
| FEATURE | Location/Qualifiers |
| misc_feature | 1..759 |
| | note = variant of L. kefir |
| source | 1..759 |
| | mol_type = other DNA |
| | organism = synthetic construct |

SEQUENCE: 61
```
atggccgatt gtctgaaggg caaagtagcc atcgtaaccg gcgggacact gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgcttttgtc   180
cagcacgatg cgtccgatga agcaggctgg acgaaactgt tcgacaccac cgaggaggca    240
ttcggcccgg ttacgaccgt cgtgaacaat gcagggattg ggttgttaa aagcgttgaa    300
gacactacca cggaggaatg gcgtaaaactg ctgtccgtta atctggatgg tgttttttc    360
ggcacccgtc tgggcattca gcgcatgaaa aataaaggct tgggcgctag catcatcaat    420
atgagcagta ttgaagggat ggtaggcgat ccgacgctgg gggcatacaa cgcttccaag    480
ggggcggtac gtatcatgtc gaaagcgca gcgctggatt gcgcactgaa ggactacgat    540
gtgcgtgtca acacagtaca tccgggctat atcaagaccc cgctggtcga tgattgggaa    600
ggtgctgagg aaatgatgtc acagcgtacg aaaaccccta tgggccacat tggtgaaccg    660
```

```
aatgacatcg catgggtctg tgtgtacctg gcatctgatg aatcgaaatt tgcgacgggt    720
gcagaatttg tggtcgacgg caagtggacc gcacagtga                            759

SEQ ID NO: 62           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 62
MADCLKGKVA IVTGGTLGIG LAIADKFVEE GAKVVITGRR ADVGEKAAKS IGGTDVIRFV     60
QHDASDEAGW TKLFDTTEEA FGPVTTVVNN AGIGVVKSVE DTTTEEWRKL LSVNLDGVFF    120
GTRLGIQRMK NKGLGASIIN MSSIEGMVGD PTLGAYNASK GAVRIMSKSA ALDCALKDYD    180
VRVNTVHPGY IKTPLLDDWE GAEEMMSQRT KTPMGHIGEP NDIAWVCVYL ASDESKFATG    240
AEFVVDGKWT AQ                                                        252

SEQ ID NO: 63           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 63
atgaccgatc gtctgaaggg caaagtagcc atcataaccg gcgggacact gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg aagttgttaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat    420
atgagcagta ttgaagggat ggtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcccg atcaagaccc cgttgctcga tgattgggaa    600
ggtgctgagg aaatgatgtc acagcgtacg aaaaccccta tgggccacat tggtgaaccg    660
aatgacatcg catgggtctg tgtgtacctg gcatctgatg aatcgaaatt tgcgacgggt    720
gcagaatttg tggtcgacgg caggtggacc gcacagtga                            759

SEQ ID NO: 64           moltype = AA  length = 252
FEATURE                 Location/Qualifiers
REGION                  1..252
                        note = variant of L. kefir
source                  1..252
                        mol_type = protein
                        organism = synthetic construct
SEQUENCE: 64
MTDRLKGKVA IITGGTLGIG LAIADKFVEE GAKVVITGRR ADVGEKAAKS IGGTDVIRFV     60
QHDASDEAGW TKLFDTTEEA FGPVTTVVNN AGIEVVKSVE DTTTEEWRKL LSVNLDGVFF    120
GTRLGIQRMK NKGLGASIIN MSSIEGMVGD PTLGAYNASK GAVRIMSKSA ALDCALKDYD    180
VRVNTVHPGP IKTPVLDDWE GAEEMMSQRT KTPMGHIGEP NDIAWVCVYL ASDESKFATG    240
AEFVVDGRWT AQ                                                        252

SEQ ID NO: 65           moltype = DNA  length = 759
FEATURE                 Location/Qualifiers
misc_feature            1..759
                        note = variant of L. kefir
source                  1..759
                        mol_type = other DNA
                        organism = synthetic construct
SEQUENCE: 65
atgaccgatc gtctgaaggg caaagtagcc atcgtaaccg gcgggacact gggtatcggt     60
ttggcaatcg ccgataaatt tgtagaggag ggtgcgaaag tagttattac tggtcgtcgt    120
gcggatgtag gtgaaaaggc cgccaaatca atcggcggca ctgatgttat tcgctttgtc    180
cagcacgatg cgtccgatga agcaggctgg acgaaactgt tcgacaccac cgaggaggca    240
ttcggcccgg ttacgaccgt cgtgaacaat gcagggattg gggttgttaa aagcgttgaa    300
gacactacca cggaggaatg gcgtaaactg ctgtccgtta atctggatgg tgttttttc    360
ggcacccgtc tgggcattca gcgcatgaaa aataaaggct tgggcgctag catcatcaat    420
atgagcagta ttttcgggat ggtaggcgat ccgacgctgg gggcatacaa cgcttccaag    480
ggggcggtac gtatcatgtc gaaaagcgca gcgctggatt gcgcactgaa ggactacgat    540
gtgcgtgtca acacagtaca tccgggcccc atcaagaccc cgctgctcga tgattgggaa    600
ggtgctgagg aaatgatgtc acagcgtacg aaaaccccta tgggccacat tggtgaaccg    660
aatgacatcg catgggtctg tgtgtacctg gcatctgatg aatcgaaatt tgcgacgggt    720
gcagaatttg tggtcgacgg cgggtggacc gcacagtga                            759

SEQ ID NO: 66           moltype = AA  length = 252
FEATURE                 Location/Qualifiers
REGION                  1..252
                        note = variant of L. kefir
```

```
source                         1..252
                               mol_type = protein
                               organism = synthetic construct
SEQUENCE: 66
MTDRLKGKVA IVTGGTLGIG LAIADKFVEE GAKVVITGRR ADVGEKAAKS IGGTDVIRFV      60
QHDASDEAGW TKLFDTTEEA FGPVTTVVNN AGIGVVKSVE DTTTEEWRKL LSVNLDGVFF     120
GTRLGIQRMK NKGLGASIIN MSSIFGMVGD PTLGAYNASK GAVRIMSKSA ALDCALKDYD     180
VRVNTVHPGP IKTPLLDDWE GAEEMMSQRT KTPMGHIGEP NDIAWVCVYL ASDESKFATG     240
AEFVVDGGWT AQ                                                         252

SEQ ID NO: 67                  moltype = DNA  length = 759
FEATURE                        Location/Qualifiers
misc_feature                   1..759
                               note = variant of L. kefir
source                         1..759
                               mol_type = other DNA
                               organism = synthetic construct
SEQUENCE: 67
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgaggaggca     240
ttcggcccgg ttacgaccgt cgtgaacaat gcagggattt tgttgttaa aagcgttgaa      300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagta ttttcgggat ggtagcgat ccgacgctgg ggcatacaa cgcttccaag      480
ggggcggtac gtatcatgtc gaaaagcgca gcgctggatt gcgcactgaa ggactacgat     540
gtgcgtgtca acacagtaca tccggggccg atcaagaccc cggtgctcga tgattgggaa     600
ggtgctgagg aaatgatgtc acagcgtacg aaaaccccta tgggccacat tggtgaaccg     660
aatgacatcg catgggtctg tgtgtacctg gcatctgatg aatcgaaatt tgcgacgggt     720
gcagaatttg tggtcgacgg caggtggacc gcacagtga                            759

SEQ ID NO: 68                  moltype = AA  length = 252
FEATURE                        Location/Qualifiers
REGION                         1..252
                               note = variant of L. kefir
source                         1..252
                               mol_type = protein
                               organism = synthetic construct
SEQUENCE: 68
MTDRLKGKVA IVTGGTLGIG LAIADKFVEE GAKVVITGRR ADVGEKAAKS IGGTDVIRFV      60
QHDASDEAGW TKLFDTTEEA FGPVTTVVNN AGIFVVKSVE DTTTEEWRKL LSVNLDGVFF     120
GTRLGIQRMK NKGLGASIIN MSSIFGMVGD PTLGAYNASK GAVRIMSKSA ALDCALKDYD     180
VRVNTVHPGP IKTPVLDDWE GAEEMMSQRT KTPMGHIGEP NDIAWVCVYL ASDESKFATG     240
AEFVVDGRWT AQ                                                         252

SEQ ID NO: 69                  moltype = DNA  length = 759
FEATURE                        Location/Qualifiers
misc_feature                   1..759
                               note = variant of L. kefir
source                         1..759
                               mol_type = other DNA
                               organism = synthetic construct
SEQUENCE: 69
atgaccgatc gtctgaaggg caaagtagcc atcgtaaccg gcgggacact gggtatcggt      60
ttggcaatcg ccgataaatt tgtagaggag ggtgcgaaag tagttattac tggtcgtcgt     120
gcggatgtag gtgaaaaggc cgccaaatca atcggcggca ctgatgttat tcgctttgtc     180
cagcacgatg cgtccgatga agcaggctgg acgaaactgt tcgacaccac cgatgaggca     240
ttcggcccgg ttacgaccgt cgtgaacaat gcagggtttg aagttgttaa aagcgttgaa     300
gacactacca cggaggaatg gcgtaaactg ctgtccgtta atctggatgg tgttttttc      360
ggcacccgtc tgggcattca gcgcatgaaa aataaaggct gggcgctag catcatcaat     420
atgagcagta ttgaagggat ggtaggcgat ccgacgctgg ggcatacaa cgcttccaag     480
ggggcggtac gtatcatgtc gaaaagcgca gcgctggatt gcgcactgaa ggactacgat     540
gtgcgtgtca acacagtaca tccggggccat atcaagaccc cggtgctcga tgattgggaa    600
ggtgctgagg aaatgatgtc acagcgtacg aaaaccccta tgggccacat tggtgaaccg     660
aatgacatcg catgggtctg tgtgtacctg gcatctgatg aatcgaaatt tgcgacgggt     720
gcagaatttg tggtcgacgg cgggcattac gcacagtga                            759

SEQ ID NO: 70                  moltype = AA  length = 252
FEATURE                        Location/Qualifiers
REGION                         1..252
                               note = variant of L. kefir
source                         1..252
                               mol_type = protein
                               organism = synthetic construct
SEQUENCE: 70
MTDRLKGKVA IVTGGTLGIG LAIADKFVEE GAKVVITGRR ADVGEKAAKS IGGTDVIRFV      60
QHDASDEAGW TKLFDTTEEA FGPVTTVVNN AGIEVVKSVE DTTTEEWRKL LSVNLDGVFF     120
GTRLGIQRMK NKGLGASIIN MSSIEGMVGD PTLGAYNASK GAVRIMSKSA ALDCALKDYD     180
```

```
VRVNTVHPGH IKTPVLDDLE GAEEMMSQRT KTPMGHIGEP NDIAWVCVYL ASDESKFATG  240
AEFVVDGGHY AQ                                                      252

SEQ ID NO: 71            moltype = DNA  length = 759
FEATURE                  Location/Qualifiers
misc_feature             1..759
                         note = variant of L. kefir
source                   1..759
                         mol_type = other DNA
                         organism = synthetic construct
SEQUENCE: 71
atgaccgatc gtctgaaggg caaagtagcc atcgtaaccg gcgggacact gggtatcggt  60
ttggcaatcg ccgataaatt tgtagaggag ggtgcgaaag tagttattac tggtcgtcgt  120
gcggatgtag gtgaaaaggc cgccaaatca atcggcgggc ctgatgttat tcgctttgtc  180
cagcacgatg cgtccgatga agcaggctgg acgaaactgt tcgacaccac cgaggaggca  240
ttcggcccgg ttacgaccgt cgtgaacaat gcagggattt tgttgttaa aagcgttgaa  300
gacactacca cgaaggaatg gcgtaaactg ctgtccgtta atctggatgg tgttttttc  360
ggcacccgtc tgggcattca gcgcatgaaa aataaaggct tgggcgctag catcatcaat  420
atgagcagta ttgatgggat ggtaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggctat atcaagaccc cgctgctcga tgattgggaa  600
ggtgctgagg aaatgatgtc acagcgtacg aaaaccccat tggccacat tggtgaaccg  660
aatgacatcg catgggtctg tgtgtacctg gcatctgatg aatcgaaatt tgcgacgggt  720
gcagaatttg tggtcgacgg cgggtggacc gcacagtga                         759

SEQ ID NO: 72            moltype = AA  length = 252
FEATURE                  Location/Qualifiers
REGION                   1..252
                         note = variant of L. kefir
source                   1..252
                         mol_type = protein
                         organism = synthetic construct
SEQUENCE: 72
MTDRLKGKVA IVTGGTLGIG LAIADKFVEE GAKVVITGRR ADVGEKAAKS IGGADVIRFV  60
QHDASDEAGW TKLFDTTEEA FGPVTTVVNN AGIFVVKSVE DTTTKEWRKL LSVNLDGVFF  120
GTRLGIQRMK NKGLGASIIN MSSIDGMVGD PTLGAYNASK GAVRIMSKSA ALDCALKDYD  180
VRVNTVHPGY IKTPLLDDWE GAEEMMSQRT KTPMGHIGEP NDIAWVCVYL ASDESKFATG  240
AEFVVDGGWT AQ                                                      252

SEQ ID NO: 73            moltype = DNA  length = 759
FEATURE                  Location/Qualifiers
misc_feature             1..759
                         note = variant of L. kefir
source                   1..759
                         mol_type = other DNA
                         organism = synthetic construct
SEQUENCE: 73
atgaccgatc gtctgaaggg caaagtagcc ttcgtaaccg gcgggacact gggtatcggt  60
ttggcaatcg ccgataaatt tgtagaggag ggtgcgaaag tagttattac tggtcgtcgt  120
gcggatgtag gtgaaaaggc cgccaaatca atcggcggca ctgatgttat tcgctttgtc  180
cagcacgatg cgtccgatga agcaggctgg acgaaactgt tcgacaccac cgaggaggca  240
ttcggcccgg ttacgaccgt cgtgaacaat gcagggattg aagttgttaa aagcgttgaa  300
gacactacca cggaggaatg gcgtaaactg ctgtccgtta atctggatgg tgttttttc  360
ggcacccgtc tgggcattca gcgcatgaaa aataaaggct gggcgctag catcatcaat  420
atgagcagta ttttcgggat ggtcaaggcgat ccgacgctgg gggcatacaa cgcttccaag  480
ggggcggtac gtatcatgtc gaaaagcgca gcgctggatt gcgcactgaa ggactacgat  540
gtgcgtgtca acacagtaca tccgggcccg atcaagaccc cggtgctcga tgattgggaa  600
ggtgctgagg aaatgatgtc acagcgtacg aaaaccccta tggccacat tggtgaaccg  660
aatgacatcg catgggtctg tgtgtacctg gcatctgatg aatcgaaatt tgcgacgggt  720
gcagaatttg tggtcgacgg cgggcatacc gcacagtga                         759

SEQ ID NO: 74            moltype = AA  length = 252
FEATURE                  Location/Qualifiers
REGION                   1..252
                         note = variant of L. kefir
source                   1..252
                         mol_type = protein
                         organism = synthetic construct
SEQUENCE: 74
MTDRLKGKVA FVTGGTLGIG LAIADKFVEE GAKVVITGRR ADVGEKAAKS IGGTDVIRFV  60
QHDASDEAGW TKLFDTTEEA FGPVTTVVNN AGIEVVKSVE DTTTEEWRKL LSVNLDGVFF  120
GTRLGIQRMK NKGLGASIIN MSSIFGMVGD PTLGAYNASK GAVRIMSKSA ALDCALKDYD  180
VRVNTVHPGP IKTPVLDDWE GAEEMMSQRT KTPMGHIGEP NDIAWVCVYL ASDESKFATG  240
AEFVVDGGHT AQ                                                      252

SEQ ID NO: 75            moltype = DNA  length = 759
FEATURE                  Location/Qualifiers
misc_feature             1..759
                         note = variant of L. kefir
```

```
source                  1..759
                        mol_type = other DNA
                        organism = synthetic construct
SEQUENCE: 75
atgaccgatc gtctgaaggg caaagtagcc ttcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggttg gggttgttaa aagcgttgaa    300
gacactacca cggaggaatg gcgtaaactg ctgtccgtta atctggatgg tgttttttc    360
ggcacccgtc tgggcattca gcgcatgaaa aataaaggct gggcgctag catcatcaat   420
atgagcagta ttttcgggat ggtaggcgat ccgacgctgg ggcatacaa cgcttccaag    480
ggggcggtac gtatcatgtc gaaaagcgca gcgctggatt gcgcactgaa ggactacgat   540
gtgcgtgtca acacagtaca tccgggccat atcaagaccc cggtgctcga tgattgggaa   600
ggtgttgagg aaatgatgtc acagcgtacg aaaaccccta tgggccacat tggtgaaccg   660
aatgacatcg catgggtctg tgtgtacctg gcatctgatg aatcgaaatt tgcgacgggt   720
gcagaatttg tggtcgacgg cgggcatacc acacagtga                         759

SEQ ID NO: 76          moltype = AA   length = 252
FEATURE                Location/Qualifiers
REGION                 1..252
                       note = variant of L. kefir
source                 1..252
                       mol_type = protein
                       organism = synthetic construct
SEQUENCE: 76
MTDRLKGKVA FVTGGTLGIG LAIADKFVEE GAKVVITGRR ADVGEKAAKS IGGTDVIRFV    60
QHDASDEAGW TKLFDTTEEA FGPVTTVVNN AGIGVVKSVE DTTTEEWRKL LSVNLDGVFF   120
GTRLGIQRMK NKGLGASIIN MSSIFGMVGD PTLGAYNASK GAVRIMSKSA ALDCALKDYD   180
VRVNTVHPGH IKTPVLDDWE GVEEMMSQRT KTPMGHIGEP NDIAWVCVYL ASDESKFATG   240
AEFVVDGGHT TQ                                                      252

SEQ ID NO: 77          moltype = DNA  length = 759
FEATURE                Location/Qualifiers
misc_feature           1..759
                       note = variant of L. kefir
source                 1..759
                       mol_type = other DNA
                       organism = synthetic construct
SEQUENCE: 77
atgaccgatc gtctgaaggg caaagtagcc ttggtaacgg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
cagcacgatg cgtccgatga agcaggctgg acgaaactgt tcgacaccac cgaggaggca   240
ttcggcccgg ttacgaccgt cgtgaacaat gcagggattg aagttgttaa aagcgttgaa   300
gacactacca cggaggaatg gcgtaaactg ctgtccgtta atctggatgg tgttttttc    360
ggcacccgtc tgggcattca gcgcatgaaa aataaaggct gggcgctag catcatcaat   420
atgagcagta ttgaagggat ggtaggcgat ccgacgctgg ggcatacaa cgcttccaag    480
ggggcggtac gtatcatgtc gaaaagcgca gcgctggatt gcgcactgaa ggactacgat   540
gtgcgtgtca acacagtaca tccgggccat atcaagaccc cgctgctcga tctctggaa   600
ggtgctgagg aaatgatgtc acagcgaacg aaaaccccta tgggccacat tggtgaaccg   660
aatgacatcg catgggtctg tgtgtacctg gcatctgatg aatcgaaatt tgcgacgggt   720
gcagaatttg tggtcgacgg aaagcatacc gcacagtga                         759

SEQ ID NO: 78          moltype = AA   length = 252
FEATURE                Location/Qualifiers
REGION                 1..252
                       note = variant of L. kefir
source                 1..252
                       mol_type = protein
                       organism = synthetic construct
SEQUENCE: 78
MTDRLKGKVA LVTGGTLGIG LAIADKFVEE GAKVVITGRR ADVGEKAAKS IGGTDVIRFV    60
QHDASDEAGW TKLFDTTEEA FGPVTTVVNN AGIEVVKSVE DTTTEEWRKL LSVNLDGVFF   120
GTRLGIQRMK NKGLGASIIN MSSIEGMVGD PTLGAYNASK GAVRIMSKSA ALDCALKDYD   180
VRVNTVHPGH IKTPLLDDLE GAEEMMSQRT KTPMGHIGEP NDIAWVCVYL ASDESKFATG   240
AEFVVDGKHT AQ                                                      252

SEQ ID NO: 79          moltype = DNA  length = 759
FEATURE                Location/Qualifiers
misc_feature           1..759
                       note = variant of L. kefir
source                 1..759
                       mol_type = other DNA
                       organism = synthetic construct
SEQUENCE: 79
atgaccgatc gtctgaaggg caatggagcc ttcgtaaccg gcgggacact gggtatcggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgctttgtc   180
```

```
cagcacgatg cgtccgatga agcaggctgg acgaaactgt tcgacaccac cgaggaggca    240
ttcggcccgg ttacgaccgt cgtgaacaat gcagggattg gggttgttaa aagcgttgaa    300
gacactacca cggaggaatg gcgtaaactg ctgtccgtta atctggatgg tgttttttc     360
ggcacccgtc tgggcattca gcgcatgaaa aataaaggct tgggcgctag catcatcaat    420
atgagcagta ttttcgggat ggtaggcgat ccgacgctgg ggcatacaa cgcttccaag     480
ggggcggtac gtatcatgtc gaaaagcgca gcgctggatt gcgcactgaa ggactacgat    540
gtgcgtgtca acacagtaca tccgggcccg atcaagaccc cgctgctcga tgatctggaa    600
ggtgctgagg aaatgatgtc acagcgtacg aaaaccccta tgggccacat tggtgaaccg    660
aatgacatcg catgggtctg tgtgtacctg gcatctgatg aatcgaaatt tgcgacgggt    720
gcagaatttg tggtcgacgg aaagaggacc gcacagtga                          759
```

| | | |
|---|---|---|
| SEQ ID NO: 80 | moltype = AA   length = 252 | |
| FEATURE | Location/Qualifiers | |
| REGION | 1..252 | |
| | note = variant of L. kefir | |
| source | 1..252 | |
| | mol_type = protein | |
| | organism = synthetic construct | |

SEQUENCE: 80
```
MTDRLKGNGA FVTGGTLGIG LAIADKFVEE GAKVVITGRR ADVGEKAAKS IGGTDVIRFV    60
QHDSDSDEAGW TKLFDTTEEA FGPVTTVVNN AGIGVVKSVE DTTTEEWRKL LSVNLDGVFF  120
GTRLGIQRMK NKGLGASIIN MSSIFGMVGD PTLGAYNASK GAVRIMSKSA ALDCALKDYD   180
VRVNTVHPGP IKTPLLDDLE GAEEMMSQRT KTPMGHIGEP NDIAWVCVYL ASDESKFATG   240
AEFVVDGKRT AQ                                                       252
```

| | | |
|---|---|---|
| SEQ ID NO: 81 | moltype = DNA   length = 759 | |
| FEATURE | Location/Qualifiers | |
| misc_feature | 1..759 | |
| | note = variant of L. kefir | |
| source | 1..759 | |
| | mol_type = other DNA | |
| | organism = synthetic construct | |

SEQUENCE: 81
```
atgaccgttc gtttgaaggg caaagtaacc atcgtaacgg gcgggacact gggtattggt    60
ttggcaatcg ccgataaatt tgtagaggag ggtgcgaaag tagttattac tggtcgtcgt   120
gcggatgtag gtgaaaaggc cgccaaatca atcggcggca ctgatgttat tcgcttttgtc  180
cagcacgatg cgtccgatga agcaggctgg acgaaactgt tcgacaccac cgaggaggca   240
ttcggcccgg ttacgaccgt cgtgaacaat gcagggattg gggttgttaa aagcgttgaa   300
gacactacca cggaggaatg gcgtaaactg ctgtccgtta atctggatgg tgttttttc    360
ggcacccgtc tgggcattca gcgcatgaaa aataaaggct tgggcgctag catcatcaat   420
atgagcagta ttgaagggat ggtaggcgat ccgacgctgg ggcatacaa cgcttccaag    480
ggggcggtac gtatcatgtc gaaaagcgca gcgctggatt gcgcactgaa ggactacgat   540
gtgcgtgtca acacagtaca tccgggcccg atcaagaccc cgctgctcga tgattgggaa   600
ggtgctgagg aaatgatgtc acagcgtacg aaaaccccta tgggccacat tggtgaaccg   660
aatgacatcg cgtgggtctg tgtgtacctg gcatctgatg aatcgaaatt tgcgacgggt   720
gcagaatttg tggtcgacgg caagcatacc gcacagtga                          759
```

| | | |
|---|---|---|
| SEQ ID NO: 82 | moltype = AA   length = 252 | |
| FEATURE | Location/Qualifiers | |
| REGION | 1..252 | |
| | note = variant of L. kefir | |
| source | 1..252 | |
| | mol_type = protein | |
| | organism = synthetic construct | |

SEQUENCE: 82
```
MTVRLKGKVT IVTGGTLGIG LAIADKFVEE GAKVVITGRR ADVGEKAAKS IGGTDVIRFV    60
QHDSDSDEAGW TKLFDTTEEA FGPVTTVVNN AGIGVVKSVE DTTTEEWRKL LSVNLDGVFF  120
GTRLGIQRMK NKGLGASIIN MSSIEGMVGD PTLGAYNASK GAVRIMSKSA ALDCALKDYD   180
VRVNTVHPGP IKTPLLDDWE GAEEMMSQRT KTPMGHIGEP NDIAWVCVYL ASDESKFATG   240
AEFVVDGKHT AQ                                                       252
```

| | | |
|---|---|---|
| SEQ ID NO: 83 | moltype = AA   length = 252 | |
| FEATURE | Location/Qualifiers | |
| REGION | 1..252 | |
| | note = Engineered Ketoreductase Sequence Formula with L. brevis backbone, Synthetic Construct | |
| VAR_SEQ | 2 | |
| | note = MISC_FEATURE - Xaa is a polar, non-polar, or aliphatic residue | |
| VAR_SEQ | 4 | |
| | note = MISC_FEATURE - Xaa is a basic or cysteine residue | |
| VAR_SEQ | 11 | |
| | note = MISC_FEATURE - Xaa is an aliphatic, non-polar, or aromatic residue | |
| VAR_SEQ | 40 | |
| | note = MISC_FEATURE - Xaa is a constrained or basic residue | |
| VAR_SEQ | 80 | |
| | note = MISC_FEATURE - Xaa is an aliphatic, non-polar, or polar residue | |

| | | |
|---|---|---|
| VAR_SEQ | 86 | |
| | note = MISC_FEATURE - Xaa is a polar, aliphatic, or non-polar residue | |
| VAR_SEQ | 94 | |
| | note = MISC_FEATURE - Xaa is an aliphatic or polar residue | |
| VAR_SEQ | 96 | |
| | note = MISC_FEATURE - Xaa is a polar, aromatic, aliphatic, or non-polar residue | |
| VAR_SEQ | 105 | |
| | note = MISC_FEATURE - Xaa is an aliphatic, non-polar, basic or acidic residue | |
| VAR_SEQ | 129 | |
| | note = MISC_FEATURE - Xaa is a non-polar or polar residue | |
| VAR_SEQ | 147 | |
| | note = MISC_FEATURE - Xaa is an aromatic, non-polar, or aliphatic residue | |
| VAR_SEQ | 153 | |
| | note = MISC_FEATURE - Xaa is an aliphatic, non-polar, or polar residue | |
| VAR_SEQ | 190 | |
| | note = MISC_FEATURE - Xaa is an aromatic or constrained residue | |
| VAR_SEQ | 195 | |
| | note = MISC_FEATURE - Xaa is a non-polar or aliphatic residue | |
| VAR_SEQ | 196 | |
| | note = MISC_FEATURE - Xaa is a non-polar or aliphatic residue | |
| VAR_SEQ | 199 | |
| | note = MISC_FEATURE - Xaa is an aliphatic, polar or constrained residue | |
| VAR_SEQ | 202 | |
| | note = MISC_FEATURE - Xaa is valine or leucine | |
| VAR_SEQ | 206 | |
| | note = MISC_FEATURE - Xaa is a non-polar or aromatic residue | |
| VAR_SEQ | 226 | |
| | note = MISC_FEATURE - Xaa is a non-polar or aliphatic residue | |
| VAR_SEQ | 248 | |
| | note = MISC_FEATURE - Xaa is a non-polar or basic residue | |
| VAR_SEQ | 249 | |
| | note = MISC_FEATURE - Xaa is an aromatic residue | |
| source | 1..252 | |
| | mol_type = protein | |
| | organism = synthetic construct | |

SEQUENCE: 83
```
MXNXLDGKVA XITGGTLGIG LAIATKFVEE GAKVMITGRX SDVGEKAAKS VGTPDQIQFF   60
QHDSSDEDGW TKLFDATEKX FGPVSXLVNN AGIXVXKSVE ETTTXEWRKL LAVNLDGVFF  120
GTRLGIQRXK NKGLGASIIN MSSIEGXVGD PSXGAYNASK GAVRIMSKSA ALDCALKDYD  180
VRVNTVHPGX IKTPXXDDXP GXEEAXSQRT KTPMGHIGEP NDIAYXCVYL ASNESKFATG  240
SEFVVDGXXT AQ                                                     252
```

| | | |
|---|---|---|
| SEQ ID NO: 84 | moltype = AA  length = 252 | |
| FEATURE | Location/Qualifiers | |
| REGION | 1..252 | |
| | note = Engineered Ketoreductase Sequence Formula with L. kefir backbone, Synthetic Construct | |
| VAR_SEQ | 2 | |
| | note = MISC_FEATURE - Xaa is a polar, non-polar, or aliphatic residue | |
| VAR_SEQ | 4 | |
| | note = MISC_FEATURE - Xaa is a basic or cysteine residue | |
| VAR_SEQ | 11 | |
| | note = MISC_FEATURE - Xaa is an aliphatic, non-polar, or aromatic residue | |
| VAR_SEQ | 40 | |
| | note = MISC_FEATURE - Xaa is a constrained or basic residue | |
| VAR_SEQ | 80 | |
| | note = MISC_FEATURE - Xaa is an aliphatic, non-polar, or polar residue | |
| VAR_SEQ | 86 | |
| | note = MISC_FEATURE - Xaa is a polar, aliphatic, or non-polar residue | |
| VAR_SEQ | 94 | |
| | note = MISC_FEATURE - Xaa is an aliphatic or polar residue | |
| VAR_SEQ | 96 | |
| | note = MISC_FEATURE - Xaa is a polar, aromatic, aliphatic, or non-polar residue | |
| VAR_SEQ | 105 | |

```
                        note = MISC_FEATURE - Xaa is an aliphatic, non-polar, basic
                         or acidic residue
VAR_SEQ                 129
                        note = MISC_FEATURE - Xaa is a non-polar or polar residue
VAR_SEQ                 147
                        note = MISC_FEATURE - Xaa is an aromatic, non-polar, or
                         aliphatic residue
VAR_SEQ                 153
                        note = MISC_FEATURE - Xaa is an aliphatic, non-polar, or
                         polar residue
VAR_SEQ                 190
                        note = MISC_FEATURE - Xaa is an aromatic or constrained
                         residue
VAR_SEQ                 195
                        note = MISC_FEATURE - Xaa is a non-polar or aliphatic
                         residue
VAR_SEQ                 196
                        note = MISC_FEATURE - Xaa is a non-polar or aliphatic
                         residue
VAR_SEQ                 199
                        note = MISC_FEATURE - Xaa is an aliphatic, polar or
                         constrained residue
VAR_SEQ                 202
                        note = MISC_FEATURE - Xaa is valine or leucine
VAR_SEQ                 206
                        note = MISC_FEATURE - Xaa is a non-polar or aromatic residue
VAR_SEQ                 226
                        note = MISC_FEATURE - Xaa is a non-polar or aliphatic
                         residue
VAR_SEQ                 248
                        note = MISC_FEATURE - Xaa is a non-polar or basic residue
VAR_SEQ                 249
                        note = MISC_FEATURE - Xaa is an aromatic residue
source                  1..252
                        mol_type = protein
                        organism = synthetic construct
SEQUENCE: 84
MXDXLKGKVA XVTGGTLGIG LAIADKFVEE GAKVVITGRX ADVGEKAAKS IGGTDVIRFV    60
QHDASDEAGW TKLFDTTEEX FGPVTXVVNN AGIXVXKSVE DTTTXEWRKL LSVNLDGVFF   120
GTRLGIQRXK NKGLGASIIN MSSIEGXVGD PTXGAYNASK GAVRIMSKSA ALDCALKDYD   180
VRVNTVHPGX IKTPXXDDXE GXEEMXSQRT KTPMGHIGEP NDIAWXCVYL ASDESKFATG   240
AEFVVDGXXT AQ                                                      252

SEQ ID NO: 85           moltype = DNA   length = 759
FEATURE                 Location/Qualifiers
source                  1..759
                        mol_type = genomic DNA
                        organism = Lactobacillus minor
SEQUENCE: 85
atgaccgatc ggttgaaggg gaaagtagca attgtaactg gcggtacctt gggaattggc    60
ttggcaatcg ctgataagtt tgttgaagaa ggcgcaaagg ttgttattac cggccgtcac   120
gctgatgtag gtgaaaaagc tgccagatca atcggcggca cagacgttat ccgttttgtc   180
caacacgatg cttctgatga aaccggctgg actaagttgt ttgatacgac tgaagaagca   240
tttggcccag ttaccacggt tgtcaacaat gccggaattg cggtcagcaa gagtgttgaa   300
gataccacaa ctgaagaatg gcgcaagctg ctctcagtta acttggatgg tgtcttcttc   360
ggtacccgtc ttggaatcca acgtatgaag aataaaggac tcggagcatc aatcatcaat   420
atgtcatcta tcgaaggttt tgttggtgat ccagctctgg gtgcataca cgcttcaaaa   480
ggtgctgtca gaattatgtc taaatcagct gccttggatt gcgctttgaa ggactacgat   540
gttcgggtta acactgttca tccaggttat atcaagacac cattggttga cgatcttgaa   600
ggggcagaag aaatgatgtc acagcggacc aagacaccaa tgggtcatat cggtgaacct   660
aacgatatcg cttggatctg tgtttacctg gcatctgacg aatctaaatt tgccactggt   720
gcagaattcg ttgtcgacgg agggtacacc gcccaatag                          759

SEQ ID NO: 86           moltype = AA   length = 252
FEATURE                 Location/Qualifiers
source                  1..252
                        mol_type = protein
                        organism = Lactobacillus minor
SEQUENCE: 86
MTDRLKGKVA IVTGGTLGIG LAIADKFVEE GAKVVITGRH ADVGEKAARS IGGTDVIRFV    60
QHDASDETGW TKLFDTTEEA FGPVTTVVNN AGIAVSKSVE DTTTEEWRKL LSVNLDGVFF   120
GTRLGIQRMK NKGLGASIIN MSSIEGFVGD PALGAYNASK GAVRIMSKSA ALDCALKDYD   180
VRVNTVHPGY IKTPLVDDLE GAEEMMSQRT KTPMGHIGEP NDIAWICVYL ASDESKFATG   240
AEFVVDGGYT AQ                                                      252

SEQ ID NO: 87           moltype = AA   length = 252
FEATURE                 Location/Qualifiers
REGION                  1..252
                        note = Engineered Ketoreductase Sequence Formula with L.
```

```
                        minor backbone, Synthetic Construct
VAR_SEQ                 2
                        note = MISC_FEATURE - Xaa is a polar, non-polar, or
                         aliphatic residue
VAR_SEQ                 4
                        note = MISC_FEATURE - Xaa is a basic or cysteine residue
VAR_SEQ                 11
                        note = MISC_FEATURE - Xaa is an aliphatic, non-polar, or
                         aromatic residue
VAR_SEQ                 40
                        note = MISC_FEATURE - Xaa is a constrained or basic residue
VAR_SEQ                 80
                        note = MISC_FEATURE - Xaa is an aliphatic, non-polar, or
                         polar residue
VAR_SEQ                 86
                        note = MISC_FEATURE - Xaa is a polar, aliphatic, or
                         non-polar residue
VAR_SEQ                 94
                        note = MISC_FEATURE - Xaa is an aliphatic or polar residue
VAR_SEQ                 96
                        note = MISC_FEATURE - Xaa is a polar, aromatic, aliphatic,
                         or non-polar residue
VAR_SEQ                 105
                        note = MISC_FEATURE - Xaa is an aliphatic, non-polar, basic
                         or acidic residue
VAR_SEQ                 129
                        note = MISC_FEATURE - Xaa is a non-polar or polar residue
VAR_SEQ                 147
                        note = MISC_FEATURE - Xaa is an aromatic, non-polar, or
                         aliphatic residue
VAR_SEQ                 153
                        note = MISC_FEATURE - Xaa is an aliphatic, non-polar, or
                         polar residue
VAR_SEQ                 190
                        note = MISC_FEATURE - Xaa is an aromatic or constrained
                         residue
VAR_SEQ                 195
                        note = MISC_FEATURE - Xaa is a non-polar or aliphatic
                         residue
VAR_SEQ                 196
                        note = MISC_FEATURE - Xaa is a non-polar or aliphatic
                         residue
VAR_SEQ                 199
                        note = MISC_FEATURE - Xaa is an aliphatic, polar or
                         constrained residue
VAR_SEQ                 202
                        note = MISC_FEATURE - Xaa is valine or leucine
VAR_SEQ                 206
                        note = MISC_FEATURE - Xaa is a non-polar or aromatic residue
VAR_SEQ                 226
                        note = MISC_FEATURE - Xaa is a non-polar or aliphatic
                         residue
VAR_SEQ                 248
                        note = MISC_FEATURE - Xaa is a non-polar or basic residue
VAR_SEQ                 249
                        note = MISC_FEATURE - Xaa is an aromatic residue
source                  1..252
                        mol_type = protein
                        organism = synthetic construct
SEQUENCE: 87
MXDXLKGKVA XVTGGTLGIG LAIADKFVEE GAKVVITGRX ADVGEKAARS IGGTDVIRFV    60
QHDASDETGW TKLFDTTEEX FGPVTXVVNN AGIXVXKSVE DTTTXEWRKL LSVNLDGVFF   120
GTRLGIQRXK NKGLGASIIN MSSIEGXVGD PAXGAYNASK GAVRIMSKSA ALDCALKDYD   180
VRVNTVHPGX IKTPXXDDXE GXEEMXSQRT KTPMGHIGEP NDIAWXCVYL ASDESKFATG   240
AEFVVDGXXT AQ                                                      252
```

KETOREDUCTASE POLYPEPTIDES FOR THE PRODUCTION OF AZETIDINONE

CROSS REFERENCES TO RELATED APPLICATIONS

This application is a Continuation of U.S. application Ser. No. 17/357,673, filed Jun. 24, 2021, which is a Continuation of U.S. application Ser. No. 16/790,474, filed Feb. 13, 2020, now U.S. Pat. No. 11,078,466, which is a Divisional of U.S. application Ser. No. 16/404,988, filed May 7, 2019, now U.S. Pat. No. 10,597,641, which is a Divisional of U.S. application Ser. No. 15/631,359, filed Jun. 23, 2017, now U.S. Pat. No. 10,329,540, which is a Continuation of U.S. application Ser. No. 15/408,673, filed Jan. 18, 2017, now U.S. Pat. No. 9,719,071, which is a Continuation of U.S. application Ser. No. 15/272,664, filed Sep. 22, 2016, now U.S. Pat. No. 9,580,694, which is a Divisional of U.S. application Ser. No. 15/175,317, filed Jun. 7, 2016, now U.S. Pat. No. 9,476,034, which claims benefit under 35 U.S.C. § 120 of U.S. application Ser. No. 14/822,624, filed Aug. 10, 2015, now U.S. Pat. No. 9,382,519, which claims benefit under 35 U.S.C. § 120 of U.S. application Ser. No. 14/658,407, filed Mar. 16, 2015, now U.S. Pat. No. 9,133,442, which claims benefit under 35 U.S.C. § 120 of U.S. application Ser. No. 13/925,096, filed Jun. 24, 2013, now U.S. Pat. No. 8,980,606, which claims benefit under 35 U.S.C. § 120 of U.S. application Ser. No. 13/569,900, filed Aug. 8, 2012, now U.S. Pat. No. 8,470,572, which is a Divisional of U.S. application Ser. No. 12/977,825, filed Dec. 23, 2010, now U.S. Pat. No. 8,257,952, which is a Continuation of U.S. application Ser. No. 12/243,968, filed Oct. 1, 2008, now U.S. Pat. No. 7,883,879, and under 35 U.S.C. § 119(e) of application Ser. No. 60/976,555, filed Oct. 1, 2007, the contents of each of which are incorporated herein by reference.

REFERENCE TO SEQUENCE LISTING, TABLE OR COMPUTER PROGRAM

The ST26 formatted version of the Sequence Listing concurrently submitted herewith under 37 C.F.R. 1.821 in a computer readable form (CRF) via EFS-Web has file name 376247-022.xml was created from the original ST25 formatted version of the Sequence Listing on Sep. 19, 2023, has a file size of 11,678,190 bytes, and is herein incorporated by reference in its entirety. The original electronic copy of the ST25 formatted version of this Sequence Listing was created on Oct. 1, 2008, with a file size of 150 Kbytes.

BACKGROUND

Enzymes belonging to the ketoreductase (KRED) or carbonyl reductase class (EC1.1.1.184) are useful for the synthesis of optically active alcohols from the corresponding prostereoisomeric ketone substrate or corresponding racemic aldehyde substrates. KREDs typically convert ketones and aldehyde substrate to the corresponding alcohol product, but may also catalyze the reverse reaction, oxidation of an alcohol substrate to the corresponding ketone/aldehyde product. The reduction of ketones and aldehydes and the oxidation of alcohols by enzymes such as KRED requires a co-factor, most commonly reduced nicotinamide adenine dinucleotide (NADH) or reduced nicotinamide adenine dinucleotide phosphate (NADPH), and nicotinamide adenine dinucleotide (NAD) or nicotinamide adenine dinucleotide phosphate (NADP) for the oxidation reaction. NADH and NADPH serve as electron donors, while NAD and NADP serve as electron acceptors. It is frequently observed that ketoreductases and alcohol dehydrogenases accept either the phosphorylated or the non-phosphorylated co-factor (in its oxidized and reduced state).

KRED enzymes can be found in a wide range of bacteria and yeasts (for reviews: Kraus and Waldman, *Enzyme catalysis in organic synthesis Vols.* 1&2. VCH Weinheim 1995; Faber, K., *Biotransformations in organic chemistry*, 4th Ed. Springer, Berlin Heidelberg New York. 2000; Hummel and Kula, 1989, *Eur. J. Biochem.* 184:1-13). Several KRED gene and enzyme sequences have been reported, e.g., *Candida magnoliae* (Genbank Acc. No. JC7338; GI:11360538) *Candida parapsilosis* (Genbank Acc. No. BAA24528.1; GI:2815409), *Sporobolomyces salmonicolor* (Genbank Acc. No. AF160799; GI:6539734).

In order to circumvent many chemical synthetic procedures for the production of key compounds, ketoreductases are being increasingly employed for the enzymatic conversion of different keto and aldehyde substrates to chiral alcohol products. These applications can employ whole cells expressing the ketoreductase for biocatalytic ketone reductions, or purified enzymes in those instances where presence of multiple ketoreductases in whole cells would adversely affect the stereopurity and yield of the desired product. For in vitro applications, a co-factor (NADH or NADPH) regenerating enzyme such as glucose dehydrogenase (GDH), formate dehydrogenase etc. is used in conjunction with the ketoreductase. Examples using ketoreductases to generate useful chemical compounds include asymmetric reduction of 4-chloroacetoacetate esters (Zhou, *J. Am. Chem. Soc.* 1983 105:5925-5926; Santaniello, *J. Chem. Res.* (S) 1984: 132-133; U.S. Pat. Nos. 5,559,030; 5,700,670 and 5,891,685), reduction of dioxocarboxylic acids (e.g., U.S. Pat. No. 6,399,339), reduction of tert-butyl (S) chloro-5-hydroxy-3-oxohexanoate (e.g., U.S. Pat. No. 6,645,746 and WO 01/40450), reduction pyrrolotriazine-based compounds (e.g., US application No. 2006/0286646); reduction of substituted acetophenones (e.g., U.S. Pat. No. 6,800,477); and reduction of ketothiolanes (WO 2005/054491).

It is desirable to identify other ketoreductase enzymes that can be used to carryout conversion of various keto substrates to its corresponding chiral alcohol products.

SUMMARY

The present disclosure provides ketoreductase polypeptides having the ability to reduce a racemic mixture of methyl-2-benzamidomethyl-3-oxobutyrate ("the substrate") to 2S,3R-methyl-2-benzamidomethyl-3-hydroxybutyrate ("the product"), polynucleotides encoding such polypeptides, and methods for using the polypeptides. The compound 2S,3R-methyl-2-benzamidomethyl-3-hydroxybutyrate is an intermediate in the synthesis of (2R,3R)-3-((R)-1-(tert-butyldimethylsilyloxy) ethyl)-4-oxoazetidin-2-yl acetate ("azetidinone; acetyoxyazetidinone"; CAS registry 76855-69-1), which is an intermediate (penultimate intermediate) used in the manufacture of various carbapenem antibiotics. Carbapenem antibiotics that can be synthesized from 2S,3R-methyl-2-benzamidomethyl-3-hydroxybutyrate include, but are not limited to, imipenem, meropenem, doripenem, ertapenem, biopenem, panipenem, and other compounds similar to thienamycin. The engineered ketoreductase polypeptides of the present disclosure have an improved property in reducing or converting the specified substrate to the corresponding chiral alcohol product as compared to the naturally-occurring wild-type ketoreductase enzymes obtained from *Lactobacillus kefir* ("*L. kefir*"; SEQ ID NO:4), *Lactobacillus brevis* ("*L. brevis*"; SEQ ID NO:2), or *Lactobacillus minor* ("*L. minor*"; SEQ ID NO:86). In some embodiments, the engineered ketoreductase polypeptides have an improved property as compared to another engineered ketoreductase polypeptide, such as SEQ ID NO: 48.

In some embodiments, the ketoreductase polypeptides have, with respect to the wild-type *L. kefir, L. brevis,* or *L. minor* KRED sequences of SEQ ID NO:4, 2, and 86, at least the following feature: residue 202 is valine or leucine. In some embodiments, the ketoreductases of the disclosure have, with respect to the sequences of SEQ ID NO:4, 2, or 86, at least two of the following features: (1) residue corresponding to position 94 (i.e., X94) is an aliphatic or polar residue, (2) residue corresponding to position 199 (i.e., X199) is an aliphatic, polar or constrained residue, and (3) residue corresponding to position 202 (i.e., X202) is valine or leucine. In some embodiments, the polypeptides have, with respect to the sequences of SEQ ID NO:4, 2, and 86, at least the following features: (1) residue corresponding to position X94 is a polar residue, (2) residue corresponding to X199 is an aliphatic, constrained, or polar residue, and (1) residue corresponding to X202 is valine or leucine.

In addition to the features described above, the ketoreductases can have one or more residue differences at other residue positions as compared to the sequences of SEQ ID NO:2, 4, or 86. In some embodiments, the ketoreductase polypeptides herein comprise an amino acid sequence that is at least about 85%, 86%, 87%, 88%, 89%, 90%, 91%, 92%, 93%, 94%, 95%, 96%, 97%, 98%, 99% or more identical to a reference sequence based on SEQ ID NO: 2, 4 or 86 having the following features: residue corresponding to X94 is an aliphatic or polar residue, particularly alanine or threonine; residue corresponding to X199 is an aliphatic, constrained or polar residue, particularly alanine, histidine, or asparagine; and residue corresponding to X202 is valine or leucine; with the proviso with the proviso that the ketoreductase amino acid sequence has at least the preceding features, i.e., residue corresponding to X94 is an aliphatic or polar residue; residue corresponding to X199 is an aliphatic, constrained or polar residue; and residue corresponding to X202 is valine or leucine.

In some embodiments, such as where the improved property is from a single residue difference or a specific combination of residue differences, the engineered ketoreductases may optionally include one or more residue differences at other positions in the polypeptide as compared to the reference sequence. In some embodiments, the residue difference comprise conservative mutations. In some embodiments, the additional residue differences at other residue positions can be incorporated to produce further improvements in enzyme properties. These improvements can be further increases in enzymatic activity for the defined substrate, but can also include increases in stereoselectivity, thermostability, solvent stability, and/or reduced product inhibition. Various residue differences that can result in one or more improved enzyme properties are provided in the detailed description. In some embodiments, an improved ketoreductase polypeptide comprises an amino acid sequence that corresponds to the sequence formulas as laid out in SEQ ID NO:83, SEQ ID NO:84, or SEQ ID NO:87 (or a region thereof, such as residues 90-211). SEQ ID NO:84 is based on the wild-type amino acid sequence of the *Lactobacillus kefir* ketoreductase (SEQ ID NO:4), SEQ ID NO:83 is based on the wild-type amino acid sequence of the *Lactobacillus brevis* ketoreductase (SEQ ID NO:2); and SEQ ID NO:87 is based on the wild-type amino acid sequence of the *Lactobacillus minor* ketoreductase (SEQ ID NO:86). The sequence formulas of SEQ ID NOs:83, 84, and 87 specify that residue corresponding to X94 is an aliphatic or polar residue; residue corresponding to X199 is an aliphatic, constrained or polar residue; and residue corresponding to X202 is valine or leucine. The sequence formulas further specify features at other residue positions, as provided in the detailed description.

In some embodiments, the engineered ketoreductase polypeptide can have increased enzymatic activity as compared to the wild-type ketoreductase enzyme for reducing the substrate to the product. Improvements in enzymatic activity can be measured by comparing the specific activity of the ketoreductase polypeptide with that of the wild-type ketoreductase enzyme using standard enzyme assays. The amount of the improvement can range from 1.5 times (or fold) the enzymatic activity of the corresponding wild-type or reference ketoreductase enzyme, to as much as 2 times, 5 times, 10 times, 20 times, 25 times, 50 times, 75 times, 100 times, or more. In specific embodiments, the engineered ketoreductase enzyme exhibits improved enzymatic activity that is at least 1.5-fold, 2-fold, 3-fold, 4-fold, 5-fold, 10-fold, 25-fold, 50-fold, 100-fold, 500-fold, or 1000-fold greater than that of the wild-type or reference ketoreductase enzyme. Improvements in enzyme activity also include increases in stereoselectivity, sterospecificity, thermostability, solvent stability, or reduced product inhibition.

In some embodiments, the ketoreductase polypeptides of the invention are improved as compared to SEQ ID NO:4, SEQ ID NO: 48, and/or SEQ ID NO:66 with respect to their rate of enzymatic activity, i.e., their rate of converting the substrate to the product. In some embodiments, the ketoreductase polypeptides are capable of converting the substrate to the product at a rate that is at least 5-fold, 10-fold, 25-fold, 50-fold, 75-fold, 100-fold, 150-fold, 200-fold, 250-fold, 300-fold, 500-fold, or 1000-fold over the rate of SEQ ID NO:4 or SEQ ID NO:90.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 85% or with a percent stereomeric excess that is greater than the wild-type *L. kefir* KRED (SEQ ID NO:4). Exemplary polypeptides with this property include, but are not limited to, polypeptides comprising amino acid sequences corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, and 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 60-89% and at a rate that is at least about 1-15 fold greater than the rate capable by the polypeptide having the amino acid sequence of SEQ ID NO:48. Exemplary polypeptides with this property include, but are not limited to, polypeptides comprising amino acid sequences corresponding to SEQ ID NO: 6, 8, 10, 12, 14, 16, 18, 20, 22, 24, 26, 28, 30, 32, 34, 36, 38, 40, 42, 46, 50, 52, 54, 56, 58, 60, and 62. Because the reference polypeptide having the amino acid sequence of SEQ ID NO:48 is capable of converting the substrate to the product at a rate (for example, 100% conversion in 20 hours of 1 g/L substrate with about 10 g/L of the KRED, in 50% IPA at pH 8) and with a stereoselectivity that is improved over wild-type (SEQ ID NO:4), the polypeptides herein that are improved over SEQ ID NO:48 are also improved over wild-type.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 90-94%. Exemplary polypeptides with this property include, but are not limited to, polypeptides comprising amino acid sequences corresponding to SEQ ID NO: 6, 8, 10, 12, 14, 16, 18, 20, 22, 24, 26, 28, 30, 32, 34, 36, 40, 42, 50, 52, 56, 58, 60, and 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 95-99%. Exemplary polypeptides with this property include, but are not limited to, polypeptides comprising amino acid sequences corresponding to SEQ ID NO: 6, 8, 10, 12, 14, 16, 18, 20, 22, 24, 26, 28, 30, 32, 34, 42, 50, 52, 56, 58, 60, and 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 99%. Exemplary polypeptides with this property include, but are not limited to, polypeptides comprising amino acid sequences corresponding to SEQ ID NO:6, 8, 10, 12, 14, 20, 22, 24, 30, 32, 34, 60, and 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 15-30 fold greater than the rate capable by the polypeptide having the amino acid sequence of SEQ ID NO:48. Exemplary polypeptides with this property include, but are not limited to, polypeptides comprising amino acid sequences corresponding to SEQ ID NO: 6, 8, 10, 12, 14, 20, 22, 24, 26, 28, 30, 32, 34, 50, 60, and 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 30-40 fold greater than the rate capable by the polypeptide having the amino acid sequence of SEQ ID NO:48. Exemplary polypeptides with this property include, but are not limited to, polypeptides comprising amino acid sequences corresponding to SEQ ID NO: 6, 8, 10, 12, 14, 20, 22, 24, 26, 30, 34, 60, and 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 40-50 fold greater than the rate capable by the polypeptide having the amino acid sequence of SEQ ID NO:48. Exemplary polypeptides with this property include, but are not limited to, polypeptides comprising amino acid sequences corresponding to SEQ ID NO: 6, 8, 10, 12, 14, 22, and 60.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 50 fold greater than the rate capable by the polypeptide having the amino acid sequence of SEQ ID NO:48. Exemplary polypeptides with this property include, but are not limited to, polypeptides comprising amino acid sequences corresponding to SEQ ID NO: 6, 8, 10, and 12.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 50 fold greater than the rate capable by the polypeptide having the amino acid sequence of SEQ ID NO:48 and with a stereomeric excess of at least 99%. Exemplary polypeptides with this property include, but are not limited to, polypeptides comprising amino acid sequences corresponding to SEQ ID NO: 6, 8, 10, and 12.

In some embodiments, the invention provides a ketoreductase polypeptide that is capable of retaining its ability to convert the substrate, methyl-2-benzamidomethyl-3-oxobutyrate, to the product, 2S,3R-methyl-2-benzamidomethyl-3-hydroxybutyrate, after heat treatment at 40° C. for 21 hours. Exemplary polypeptides with this property include, but are not limited to, polypeptides comprising amino acid sequences corresponding to SEQ ID NO: 6, 10, and 44.

In another aspect, the present disclosure further provides ketoreductase polypeptides capable of converting the substrate, methyl-2-benzamidomethyl-3-oxobutyrate, to the product, 2R,3R-methyl-2-benzamidomethyl-3-hydroxybutyrate. In some embodiments, these ketoreductases are capable of converting the substrate, methyl-2-benzamidomethyl-3-oxobutyrate, to the product, 2R,3R-methyl-2-benzamidomethyl-3-hydroxybutyrate with a percent stereomeric excess of at least about 85%. Exemplary polypeptides include, but are not limited to, polypeptides comprising amino acid sequences corresponding to SEQ ID NO: 68, 72, 74, 76, 78, and 82.

In some embodiments, the 2R,3R selective ketoreductase polypeptide are capable of converting the substrate, methyl-2-benzamidomethyl-3-oxobutyrate, to the product, 2R,3R-methyl-2-benzamidomethyl-3-hydroxybutyrate, at a rate that is at least about 1 fold greater than the rate capable by the polypeptide having the amino acid sequence of SEQ ID NO:66. Exemplary polypeptides with this property include, but are not limited to, polypeptides comprising amino acid sequences corresponding to SEQ ID NO: 64, 68, 70, 72, 74, 76, 78. 80 and 82. Because the polypeptide having the amino acid sequence of SEQ ID NO:66 is capable of capable of converting the substrate, methyl-2-benzamidomethyl-3-oxobutyrate, to the product, 2R, 3R-methyl-2-benzamidomethyl-3-hydroxybutyrate, with a stereomeric excess and at a rate that is greater than wild-type L. kefir KRED (SEQ ID NO:4), any polypeptide improved over SEQ ID NO:66 is also improved over wild-type L. kefir KRED.

In some embodiments, the 2R,2R selective ketoreductase polypeptide are capable of converting the substrate, methyl-2-benzamidomethyl-3-oxobutyrate, to the product, 2R,3R-methyl-2-benzamidomethyl-3-hydroxybutyrate, at a rate that is at least about 1-2 fold greater than the rate capable by the polypeptide having the amino acid sequence of SEQ ID NO:66. Exemplary polypeptides with this property include, but are not limited to, polypeptides comprising amino acid sequences corresponding to SEQ ID NO: 64, 68, 70, 72, 74, 76, 78. and 80.

In some embodiments, the 2R,2R selective ketoreductase polypeptides are capable of converting the substrate, methyl-2-benzamidomethyl-3-oxobutyrate, to the product, 2R,3R-methyl-2-benzamidomethyl-3-hydroxybutyrate, at a rate that is at least about 5 fold greater than the rate capable by the polypeptide having the amino acid sequence of SEQ ID NO:66. Exemplary polypeptides with this property include, but are not limited to, polypeptides comprising amino acid sequences corresponding to SEQ ID NO: 64, 70, 72, 76, 78. and 80.

In some embodiments, the 2R,2R selective ketoreductase polypeptides are capable of converting the substrate, methyl-2-benzamidomethyl-3-oxobutyrate, to the product, 2R, 3R-methyl-2-benzamidomethyl-3-hydroxybutyrate, at a rate that is at least about 5 fold greater than the rate capable by the polypeptide having the amino acid sequence of SEQ ID NO:66 and with a stereomeric excess that is at least 85%. Exemplary polypeptides with this property include, but are not limited to, polypeptides comprising amino acid sequences corresponding to SEQ ID NO: 72 and 78.

In another aspect, the present disclosure provides polynucleotides encoding the engineered ketoreductases described herein or polynucleotides that hybridize to such polynucleotides under highly stringent conditions. The polynucleotide can include promoters and other regulatory elements useful for expression of the encoded engineered ketoreductase, and can utilize codons optimized for specific desired expression systems. Exemplary polynucleotides include, but are not limited to, SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, and 81. Exemplary polynucleotides also include polynucleotides encoding polypeptides that correspond to the sequence formulas of SEQ ID NO:83, 84, and 87.

In another aspect, the present disclosure provides host cells comprising the polynucleotides and/or expression vectors described herein. The host cells may be *L. kefir* or *L. brevis* or *L. minor*, or they may be a different organism. The host cells can be used for the expression and isolation of the engineered ketoreductase enzymes described herein, or, alternatively, they can be used directly for the conversion of the substrate to the stereoisomeric product.

Whether carrying out the method with whole cells, cell extracts or purified ketoreductase enzymes, a single ketoreductase enzyme may be used or, alternatively, mixtures of two or more ketoreductase enzymes may be used.

As noted above, in some embodiments, the ketoreductase enzymes described herein are capable of catalyzing the reduction reaction of the keto group in the compound of structural formula (I), methyl-2-benzamidomethyl-3-oxobutyrate ("the substrate"):

(I)

to the corresponding stereoisomeric alcohol product of structural formula (II), 2S,3R-methyl-2-benzamidomethyl-3-hydroxybutyrate ("the product"):

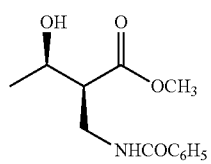

(II)

In some embodiments, the ketoreductase enzymes described herein are capable of catalyzing the reduction reaction of the keto group in the compound of structural formula (I) to the corresponding stereoisomeric alcohol product of structural formula (III), 2R,3R-methyl-2-benzamidomethyl-3-hydroxybutyrate, (which can also be referred to as a "product"):

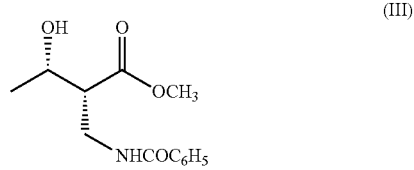

(III)

Accordingly, in some embodiments, provide herein are methods for reducing the substrate of the structural formula (I) to the alcohol product of structural formula (II) or structural formula (III), which method comprises contacting or incubating the substrate with a ketoreductase polypeptide of the disclosure under reaction conditions suitable for reducing or converting the substrate to the product of structural formula (II) or structural formula (III).

In some embodiments, the product 2S,3R-methyl-2-benzamidomethyl-3-hydroxybutyrate of structural formula (II) can be used to synthesize intermediates and carbapenem compounds, as illustrated in Scheme 3:

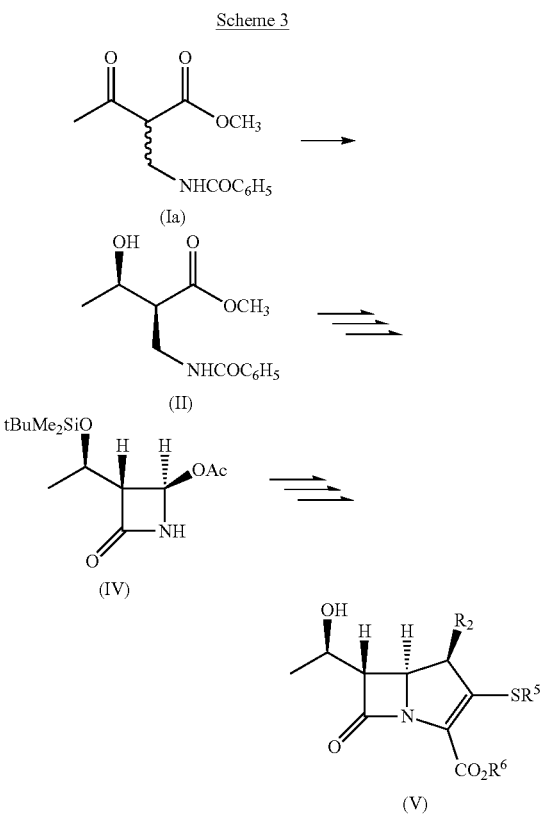

Scheme 3

Accordingly, in some embodiments, the ketoreductases of the disclosure can be used in a method for the synthesis of the intermediate of structural formula (IVa),

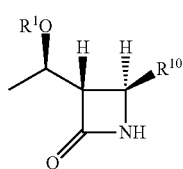

(IVa)

where $R^1$ is H or a hydroxyl protecting group, and $R^{10}$ is a halogen (e.g., Cl), or —OAc (Ac is acetate). Accordingly, in a method for the synthesis of the intermediate of structural formula (IVa), a step in the method comprises contacting or reacting the substrate of formula (I) with a ketoreductase of the disclosure under reaction conditions suitable for reducing or converting the substrate to the product of formula (II).

In some embodiments, the ketoreductases of the disclosure can be use in the synthesis of the intermediate of structural formula (VI):

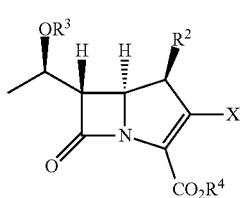

(VI)

where $R^2$ is H or a C1-C4 alkyl (e.g., —CH$_3$); $R^3$ is H, or a hydroxyl protecting group; $R^4$ is H, carboxy protecting group, ammonia group, alkali metal, or alkaline earth metal; and X is OH, or a leaving group. Exemplary leaving groups include, but are not limited to, —OP(O)(OR') or OS(O2)R", where R' and R" can be C1-C6 alkyl, C1-C6 alkaryl, aryl, perfluoro C1-C6 alkyl. Accordingly, in some embodiments, in a method for the synthesis of the intermediate of formula (VI), a step in the method comprises contacting or reacting the substrate of formula (I) with a ketoreductase of the disclosure under reaction conditions suitable for reducing or converting the substrate to the product of formula (II).

In some embodiments, the ketoreductases of the disclosure can be used in the process for synthesis of carbapenem based therapeutic compound of structural formula (V):

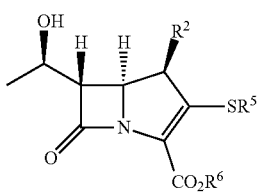

(V)

or solvates, hydrates, salts, and prodrugs thereof, where $R^2$ is H or —CH$_3$; $R^5$ can be various substituents, including, but not limited to, substituted or unsubstituted alkyl, substituted or unsubstituted aryl, substituted or unsubstituted heteroalkyl, substituted or unsubstituted heterocycloalkyl, and substituted or unsubstituted heteroarylalkyl; and $R^6$ is H, or a progroup, such as a hydrolyzable ester group. Accordingly, in the method for the synthesis of the compound of structural formula (V), a step in the method can comprise contacting or reacting the substrate of formula (I) with the ketoreductases of the disclosure under reaction conditions suitable for reducing or converting the substrate to the product of formula (II). Exemplary carbapenems of structural formula (V) include, but are not limited to, Imipenem, Meropenem, Doripenem, Ertapenem, Biopenem, and Panipenem.

In some embodiments, the disclosure further provides use of the ketoreductases in methods of synthesizing sulopenem compounds and in the intermediates used in the synthesis of sulopenems.

BRIEF DESCRIPTION OF THE FIGURES

FIG. 1 illustrates the role of ketoreductases (KRED) in the conversion of the substrate compound of formula (I) to the corresponding product of formula (II). This reduction uses a KRED of the invention and a co-factor such as NADPH. Isopropyl alcohol (IPA) is used to covert/recycle NADP$^+$ to NADPH.

DETAILED DESCRIPTION 1.1 Definitions

As used herein, the following terms are intended to have the following meanings.

"Ketoreductase" and "KRED" are used interchangeably herein to refer to a polypeptide having an enzymatic capability of reducing a carbonyl group to its corresponding alcohol. More specifically, the ketoreductase polypeptides of the invention are capable of stereoselectively reducing the compound of formula (I), supra to the corresponding product of formula (II), supra. The polypeptide typically utilizes a cofactor reduced nicotinamide adenine dinucleotide (NADH) or reduced nicotinamide adenine dinucleotide phosphate (NADPH) as the reducing agent. Ketoreductases as used herein include naturally occurring (wild type) ketoreductases as well as non-naturally occurring engineered polypeptides generated by human manipulation.

"Coding sequence" refers to that portion of a nucleic acid (e.g., a gene) that encodes an amino acid sequence of a protein.

"Naturally-occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, *Adv. Appl. Math.* 2:482, by the homology alignment algorithm of Needleman and Wunsch, 1970, *J. Mol. Biol.* 48:443, by the search for similarity method of Pearson and Lipman, 1988, *Proc. Natl. Acad. Sci. USA* 85:2444, by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, *J. Mol. Biol.* 215: 403-410 and Altschul et al., 1977, *Nucleic Acids Res.* 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, *Proc Natl Acad Sci USA* 89:10915). Exemplary determination of sequence alignment and % sequence identity can employ the BESTFIT or GAP programs in the GCG Wisconsin Software package (Accelrys, Madison WI), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

In some embodiments, a "reference sequence" can be based on a primary amino acid sequence, where the reference sequence is a sequence that can have one or more changes in the primary sequence. For instance, a "reference sequence based on SEQ ID NO:4 having at the residue corresponding to X202 a leucine or valine" refers to a reference sequence in which the corresponding residue at X202 in SEQ ID NO:4 has been changed to a leucine or valine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered ketoreductase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diasteromers, commonly alternatively reported as the diastereomeric excess (d.e.). Enantiomeric excess and diastereomeric excess are types of stereomeric excess.

"Highly stereoselective" refers to a ketoreductase polypeptide that is capable of converting or reducing the substrate to the corresponding product having the chemical formula (II) or (III) with at least about 85% stereomeric excess.

"Stereospecificity" refers to the preferential conversion in a chemical or enzymatic reaction of one stereoisomer over another. Stereospecificity can be partial, where the conversion of one stereoisomer is favored over the other, or it may be complete where only one stereoisomer is converted.

"Chemoselectivity" refers to the preferential formation in a chemical or enzymatic reaction of one product over another.

"Improved enzyme property" refers to a ketoreductase polypeptide that exhibits an improvement in any enzyme property as compared to a reference ketoreductase. For the engineered ketoreductase polypeptides described herein, the comparison is generally made to the wild-type ketoreductase enzyme, although in some embodiments, the reference ketoreductase can be another improved engineered ketoreductase. Enzyme properties for which improvement is desirable include, but are not limited to, enzymatic activity (which can be expressed in terms of percent conversion of the substrate), thermal stability, solvent stability, pH activity profile, cofactor requirements, refractoriness to inhibitors (e.g., product inhibition), stereospecificity, and stereoselectivity (including enantioselectivity).

"Increased enzymatic activity" refers to an improved property of the engineered ketoreductase polypeptides, which can be represented by an increase in specific activity (e.g., product produced/time/weight protein) or an increase in percent conversion of the substrate to the product (e.g., percent conversion of starting amount of substrate to product in a specified time period using a specified amount of KRED) as compared to the reference ketoreductase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.5 times the enzymatic activity of the corresponding wild-type ketoreductase enzyme, to as much as 2 times. 5 times, 10 times, 20 times, 25 times, 50 times, 75 times, 100 times, or more enzymatic activity than the naturally occurring ketoreductase or another engineered ketoreductase from which the ketoreductase polypeptides were derived. In specific embodiments, the engineered ketoreductase enzyme exhibits improved enzymatic activity in the range of 1.5 to 50 times, 1.5 to 100 times greater than that of the parent ketoreductase enzyme. It is understood by the skilled artisan that the activity of any enzyme is diffusion limited such that the catalytic turnover rate cannot exceed the diffusion rate of the substrate, including any required cofactors. The theoretical maximum of the diffusion limit, or $k_{cat}/K_m$, is generally about $10^8$ to $10^9$ ($M^{-1}$ $s^{-1}$). Hence, any improvements in the enzyme activity of the ketoreductase will have an upper limit related to the diffusion rate of the substrates acted on by the ketoreductase enzyme. Ketoreductase activity can be measured by any one of standard assays used for measuring ketoreductase, such as a decrease in absorbance or fluorescence of NADPH due to its oxidation with the concomitant reduction of a ketone to an alcohol, or by product produced in a coupled assay. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic reduction of the substrate to the corresponding product. "Percent conversion" refers to the percent of the substrate that is reduced to the product within a period of time under specified conditions. Thus, the "enzymatic activity" or "activity" of a ketoreductase polypeptide can be expressed as "percent conversion" of the substrate to the product.

"Thermostable" refers to a ketoreductase polypeptide that maintains similar activity (more than 60% to 80% for example) after exposure to elevated temperatures (e.g., 40-80° C.) for a period of time (e.g., 0.5-24 hrs) compared to the untreated enzyme.

"Solvent stable" refers to a ketoreductase polypeptide that maintains similar activity (more than e.g., 60% to 80%) after exposure to varying concentrations (e.g., 5-99%) of solvent (isopropylalcohol, tetrahydrofuran, 2-methyltetrahydrofuran, acetone, toluene, butylacetate, methyl tert-butylether, etc.) for a period of time (e.g., 0.5-24 hrs) compared to the untreated enzyme.

"pH stable" refers to a ketoreductase polypeptide that maintains similar activity (more than e.g., 60% to 80%) after exposure to high or low pH (e.g., 4.5-6 or 8 to 12) for a period of time (e.g., 0.5-24 hrs) compared to the untreated enzyme.

"Thermo- and solvent stable" refers to a ketoreductase polypeptide that are both thermostable and solvent stable.

"Derived from" as used herein in the context of engineered ketoreductase enzymes, identifies the originating ketoreductase enzyme, and/or the gene encoding such ketoreductase enzyme, upon which the engineering was based. For example, the engineered ketoreductase enzyme of SEQ ID NO: 60 was obtained by artificially evolving, over multiple generations the gene encoding the *Lactobacillus kefir* ketoreductase enzyme of SEQ ID NO:4. Thus, this engineered ketoreductase enzyme is "derived from" the wild-type ketoreductase of SEQ ID NO: 4.

"Hydrophilic amino acid or residue" refers to an amino acid or residue having a side chain exhibiting a hydrophobicity of less than zero according to the normalized consensus hydrophobicity scale of Eisenberg et al., 1984, *J. Mol. Biol.* 179:125-142. Genetically encoded hydrophilic amino acids include L-Thr (T), L-Ser (S), L-His (H), L-Glu (E), L-Asn (N), L-Gln (Q), L-Asp (D), L-Lys (K) and L-Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L-Glu (E) and L-Asp (D).

"Basic amino acid or residue" refers to a hydrophilic amino acid or residue having a side chain exhibiting a pK value of greater than about 6 when the amino acid is included in a peptide or polypeptide. Basic amino acids typically have positively charged side chains at physiological pH due to association with hydronium ion. Genetically encoded basic amino acids include L-Arg (R) and L-Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L-Asn (N), L-Gln (Q), L-Ser (S) and L-Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, *J. Mol. Biol.* 179:125-142. Genetically encoded hydrophobic amino acids include L-Pro (P), L-Ile (I), L-Phe (F), L-Val (V), L-Leu (L), L-Trp (W), L-Met (M), L-Ala (A) and L-Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L-Phe (F), L-Tyr (Y) and L-Trp (W). Although owing to the pKa of its heteroaromatic nitrogen atom L-His (H) it is sometimes classified as a basic residue, or as an aromatic residue as its side chain includes a heteroaromatic ring, herein histidine is classified as a hydrophilic residue or as a "constrained residue" (see below).

"Constrained amino acid or residue" refers to an amino acid or residue that has a constrained geometry. Herein, constrained residues include L-pro (P) and L-his (H). Histidine has a constrained geometry because it has a relatively small imidazole ring. Proline has a constrained geometry because it also has a five membered ring.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L-Gly (G), L-Leu (L), L-Val (V), L-Ile (I), L-Met (M) and L-Ala (A).

"Aliphatic amino acid or residue" refers to a hydrophobic amino acid or residue having an aliphatic hydrocarbon side chain. Genetically encoded aliphatic amino acids include L-Ala (A), L-Val (V), L-Leu (L) and L-Ile (I).

"Cysteine" or L-Cys (C) is unusual in that it can form disulfide bridges with other L-Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L-Cys (C) (and other amino acids with —SH containing side chains) to exist in a peptide in either the reduced free —SH or oxidized disulfide-bridged form affects whether L-Cys (C) contributes net hydrophobic or hydrophilic character to a peptide. While L-Cys (C) exhibits a hydrophobicity of 0.29 according to the normalized consensus scale of Eisenberg (Eisenberg et al., 1984, supra), it is to be understood that for purposes of the present disclosure L-Cys (C) is categorized into its own unique group.

"Small amino acid or residue" refers to an amino acid or residue having a side chain that is composed of a total three or fewer carbon and/or heteroatoms (excluding the α-carbon and hydrogens). The small amino acids or residues may be further categorized as aliphatic, non-polar, polar or acidic small amino acids or residues, in accordance with the above definitions. Genetically-encoded small amino acids include L-Ala (A), L-Val (V), L-Cys (C), L-Asn (N), L-Ser (S), L-Thr (T) and L-Asp (D).

"Hydroxyl-containing amino acid or residue" refers to an amino acid containing a hydroxyl (—OH) moiety. Genetically-encoded hydroxyl-containing amino acids include L-Ser (S) L-Thr (T) and L-Tyr (Y).

"Conservative" amino acid substitutions or mutations refer to the interchangeability of residues having similar side chains, and thus typically involves substitution of the amino acid in the polypeptide with amino acids within the same or similar defined class of amino acids. However, as used herein, in some embodiments, conservative mutations do not include substitutions from a hydrophilic to hydrophilic, hydrophobic to hydrophobic, hydroxyl-containing to hydroxyl-containing, or small to small residue, if the conservative mutation can instead be a substitution from an aliphatic to an aliphatic, non-polar to non-polar, polar to polar, acidic to acidic, basic to basic, aromatic to aromatic, or constrained to constrained residue. Further, as used herein, A, V, L, or I can be conservatively mutated to either another aliphatic residue or to another non-polar residue. The table below shows exemplary conservative substitutions.

TABLE 1

| Residue | Possible Conservative Mutations |
| --- | --- |
| A, L, V, I | Other aliphatic (A, L, V, I) |
| | Other non-polar (A, L, V, I, G, M) |
| G, M | Other non-polar (A, L, V, I, G, M) |
| D, E | Other acidic (D, E) |
| K, R | Other basic (K, R) |
| P, H | Other constrained (P, H) |
| N, Q, S, T | Other polar |
| Y, W, F | Other aromatic (Y, W, F) |
| C | None |

"Non-conservative substitution" refers to substitution or mutation of an amino acid in the polypeptide with an amino acid with significantly differing side chain properties. Non-conservative substitutions may use amino acids between, rather than within, the defined groups listed above. In one embodiment, a non-conservative mutation affects (a) the structure of the peptide backbone in the area of the substitution (e.g., proline for glycine) (b) the charge or hydrophobicity, or (c) the bulk of the side chain.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, up to 20% of the total number of amino acids, or up to 30% of the total number of amino acids making up the polypeptide while retaining enzymatic activity and/or retaining the improved properties of an engineered ketoreductase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered ketoreductase enzymes comprise insertions of one or more amino acids to the naturally occurring ketoreductase polypeptide as well as insertions of one or more amino acids to other improved ketoreductase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length ketoreductase polypeptide, for example the polypeptide of SEQ ID NO:2, 4 or 86.

"Isolated polypeptide" refers to a polypeptide which is substantially separated from other contaminants that naturally accompany it, e.g., protein, lipids, and polynucleotides. The term embraces polypeptides which have been removed or purified from their naturally-occurring environment or expression system (e.g., host cell or in vitro synthesis). The improved ketoreductase enzymes may be present within a cell, present in the cellular medium, or prepared in various forms, such as lysates or isolated preparations. As such, in some embodiments, the improved ketoreductase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure ketoreductase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved ketoreductases polypeptide is a substantially pure polypeptide composition.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., *Methods Enzymology* 168:761-777; Bolton et al., 1962, *Proc. Natl. Acad. Sci. USA* 48:1390; Bresslauer et al., 1986, *Proc. Natl. Acad. Sci USA* 83:8893-8897; Freier et al., 1986, *Proc. Natl. Acad. Sci USA* 83:9373-9377; Kierzek et al., *Biochemistry* 25:7840-7846; Rychlik et al., 1990, *Nucleic Acids Res* 18:6409-6412 (erratum, 1991, *Nucleic Acids Res* 19:698); Sambrook et al., supra); Suggs et al., 1981, In *Developmental Biology Using Purified Genes* (Brown et al., eds.), pp. 683-693, Academic Press; and Wetmur, 1991, *Crit Rev Biochem Mol Biol* 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered ketoreductase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA; with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the ketoreductases enzymes may be codon optimized for optimal production from the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, *Bioinformatics* 14:372-73; Stenico et al., 1994, *Nucleic Acids Res.* 222437-46; Wright, F., 1990, *Gene* 87:23-29). Codon usage tables are available for a growing list of organisms (see for example, Wada et al., 1992, *Nucleic Acids Res.* 20:2111-2118; Nakamura et al., 2000, *Nucl. Acids Res.* 28:292; Duret, et al., supra; Henaut and Danchin, "*Escherichia coli* and *Salmonella*," 1996, Neidhardt, et al. Eds., ASM Press, Washington D.C., p. 2047-2066. The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, *Methods Enzymol.* 266:259-281; Tiwari et al., 1997, *Comput. Appl. Biosci.* 13:263-270).

"Control sequence" is defined herein to include all components, which are necessary or advantageous for the expression of a polypeptide of the present disclosure. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" is a nucleic acid sequence that is recognized by a host cell for expression of a polynucleotide of interest, such as a coding sequence. The control sequence may comprise an appropriate promoter sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

1.2 Ketoreductase Enzymes

In one aspect, the present disclosure provides engineered ketoreductase ("KRED") enzymes that are capable of stereoselectively reducing or converting the racemic mixture of methyl-2-benzamidomethyl-3-oxobutyrate ("the substrate") to 2S,3R-methyl-2-benzamidomethyl-3-hydroxybutyrate ("the 2S,3R product"). These ketoreductase polypeptides (also described herein as "2S,3R selective ketoreductases") have an improved property for reducing or converting methyl-2-benzamidomethyl-3-oxobutyrate to 2S,3R-methyl-2-benzamidomethyl-3-hydroxybutyrate when compared with the naturally-occurring, wild-type KRED enzyme obtained from *L. kefir* (SEQ ID NO:4), *L. brevis* (SEQ ID NO:2), or *L. minor* (SEQ ID NO:86) or when compared with other engineered ketoreductase enzymes.

In some embodiments, the improved property as compared to wild-type or another engineered polypeptide, such as SEQ ID NO:64, is with respect to increase in stereoselectivity for reducing or converting the substrate methyl-2-benzamidomethyl-3-oxobutyrate to 2S,3R-methyl-2-benzamidomethyl-3-hydroxybutyrate, i.e., herein, an increase in the stereomeric excess of the product. In some embodiments, the improved property of the ketoreductase polypeptide is with respect to an increase in its ability to convert or reduce a greater percentage of the substrate to the product. In some embodiments, the improved property of the ketoreductase polypeptide is with respect to an increase in its rate of conversion of the substrate to the product, which can be manifested by the ability to use less of the improved polypeptide as compared to the wild-type or other reference sequence to reduce or convert the same amount of product. In some embodiments, the improved property of the ketoreductase polypeptide is with respect to its stability or thermostability. In some embodiments, the ketoreductase polypeptide has more than one improved property, such as increased stereoselectivity and improved enzymatic activity.

The present disclosure further provides engineered ketoreductase enzymes that are capable of stereoselectively reducing or converting a racemic mixture of methyl-2-benzamidomethyl-3-oxobutyrate ("the substrate) to 2R,3R-methyl-2-benzamidomethyl-3-hydroxybutyrate ("the 2R,3R product"). Similar to the engineered polypeptides that produce the 2S,3R product, the engineered ketoreductases capable of producing the 2R,3R product (also described herein as 2R,3R selective ketoreductases) have an improved property as compared to wild-type or another engineered polypeptide, such as SEQ ID NO:66. In some embodiments, the improved property is with respect to the stereoselectivity for reducing or converting the substrate methyl-2-benzamidomethyl-3-oxobutyrate to 2R,3R-methyl-2-benzamidomethyl-3-hydroxybutyrate. In some embodiments, the improved property is with respect to it enzymatic activity for reducing the substrate to the 2R,3R product. In some embodiments, the improved property of the ketoreductase polypeptide is with respect to its stability or thermostability. In some embodiments, the ketoreductase polypeptide has more than one improved property, such as increased stereoselectivity and improved enzymatic activity.

As described in more detail below, the ketoreductase polypeptides capable of converting the substrate to the 2S,3R product comprise an amino acid sequence in which the residue corresponding to X202 of SEQ ID NO:2, 4, or 86 is valine or leucine. In some embodiments, the ketoreductase polypeptides comprise an amino acid sequence in which the residue corresponding to X94 of SEQ ID NO:2, 4, or 86 is an aliphatic or polar residue, particularly alanine or threonine; and the residue corresponding to X202 of SEQ ID NO:2, 4, or 86 is valine or leucine. In some embodiments, the 2S,3R selective ketoreductase polypeptides comprise an amino acid sequence in which the residue corresponding to X94 of SEQ ID NO:2, 4, or 86 is an aliphatic or polar residue, particularly alanine or threonine; residue corresponding to X199 of SEQ ID NO:2. 4. or 86 is a constrained, polar, or aliphatic residue, particularly histidine, asparagine, or alanine; and residue corresponding to X202 of SEQ ID NO:2, 4, or 86 is valine or leucine.

As noted above, the ketoreductases of the disclosure can be described in reference to the amino acid sequence of a naturally occurring ketoreductase of *L. kefir, L. brevis*, or *L. minor* (also referred to as "ADH" or "alcohol dehydrogenase") or another engineered ketoreductase. As such, the amino acid residue position is determined in the ketoreductases beginning from the initiating methionine (M) residue (i.e., M represents residue position 1), although it will be understood by the skilled artisan that this initiating methionine residue may be removed by biological processing machinery, such as in a host cell or in vitro translation system, to generate a mature protein lacking the initiating methionine residue. The amino acid residue position at which a particular amino acid or amino acid change is present in an amino acid sequence is sometimes describe herein in terms "Xn", or "position n", where n refers to the residue position. Where the amino acid residues at the same residue position differ between the ketoreductases, the different residues may be denoted by an "/" with the arrangement being "*kefir* residue/*brevis* residue/minor". A substitution mutation, which is a replacement of an amino acid residue in a reference sequence, for example the wildtype ketoreductases of SEQ ID NO:2 and SEQ ID NO:4 and SEQ ID NO:86, with a different amino acid residue may be denoted by the symbol "→". Herein, in some embodiments, mutations are sometimes described as a mutation "to a" type of amino acid. For example, residue 199 of SEQ ID NO:4 can be mutated "to a" polar residue. But the use of the phrase "to a" does not exclude mutations from one amino acid of a class to another amino acid of the same class. For example, residue 199 of SEQ ID NO:4 is an aliphatic residue, leucine, but it can be mutated to a different aliphatic residue, for example, the mutation can be a "L199A" (199→A) mutation. The amino acid sequence of the naturally occurring ketoreductase (also referred to as "ADH" or "alcohol dehydrogenase") of *L. kefir, L. brevis*, or *L. minor*, can be obtained from the polynucleotide known to encode the ketoreductase activity (e.g., Genbank accession no. AAP94029 GI:33112056 or SEQ ID NO:3 for *L. kefir*; Genbank accession no. CAD66648 GI:28400789 or SEQ ID NO:1 for *L. brevis*; and SEQ ID NO:86 for *L. minor*).

In some embodiments, the ketoreductase polypeptides herein can have a number of modifications to the reference sequence (e.g., naturally occurring polypeptide or an engineered polypeptide) to result in the improved ketoreductase property. As used herein, "modifications" include amino acid substitutions, deletions, and insertions. Any one or a combination of modifications can be introduced into the naturally occurring or engineered polypeptide to generate engineered enzymes. In such embodiments, the number of modifications to the amino acid sequence can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 15% of the total number of amino acids, up to 20% of the total number of amino acids, or up to 30% of the total number of amino acids of the reference polypeptide sequence. In some embodiments, the number of modifications to the naturally occurring polypeptide or an engineered polypeptide that produces an improved ketoreductase property may comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 modifications of the reference sequence. In some embodiments, the number of modifications can be 1, 2, 3, 4, 5, 6, 7, 8, 9, 10, 11, 12, 14, 15, 16, 18, 20, 22, 24, 26, 30, 35 or about 40 amino acid residues. The modifications can comprise insertions, deletions, substitutions, or combinations thereof.

In some embodiments, the modifications comprise amino acid substitutions to the reference sequence. Substitutions that can produce an improved ketoreductase property may be at one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the reference enzyme sequence. In some embodiments, the number of substitutions to the naturally occurring polypeptide or an engineered polypeptide that produces an improved ketoreductase property can comprise from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 amino acid substitutions of the reference sequence. In some embodiments, the number of substitutions can be 1, 2, 3, 4, 5, 6, 7, 8, 9, 10, 11, 12, 14, 15, 16, 18, 20, 22, 24, 26, 30, 35 or about 40 amino acid residues.

In some embodiments, the improved ketoreductase polypeptide comprises an amino acid sequence that is at least about 85%, 86%, 87%, 88%, 89%, 90%, 91%, 92%, 93%, 94%, 95%, 96%, 97%, 98%, or 99% or more identical to a reference sequence based on SEQ ID NO:2, 4, or 86 having at the residue corresponding to X202 a leucine or valine, with the proviso that the ketoreductase polypeptide has an amino acid sequence in which the residue corresponding to X202 is leucine or valine. In some embodiments, the residue corresponding to X202 is leucine. In some embodiments, these ketoreductase polypeptides can have one or more residue differences at other residue positions as compared to the reference amino acid sequence. The differences include various modifications, such as substitutions, deletions, and insertions. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence. In some embodiments, the number of difference can be 1, 2, 3, 4, 5, 6, 7, 8, 9, 10, 11, 12, 14, 15, 16, 18, 20, 22, 24, 26, 30, 35 or about 40 residue differences at other amino acid residues as compared to the reference sequence. In some embodiments, the reference sequence is SEQ ID NO:48.

In some embodiments, the improved ketoreductase polypeptide comprises an amino acid sequence that is at least about 85%, 86%, 87%, 88%, 89%, 90%, 91%, 92%, 93%, 94%, 95%, 96%, 97%, 98%, or 99% or more identical to a reference sequence based on SEQ ID NO:2, 4 or 86 having the following features: residue corresponding to X94 is an aliphatic or polar residue, particularly alanine or threonine; and residue corresponding to X202 is valine or leucine; with the proviso that the ketoreductase polypeptide has an amino acid sequence having at least the preceding features (i.e., the residue corresponding to X94 is an aliphatic or polar residue, and the residue corresponding to X202 is valine or leucine). In some embodiments, the ketoreductase has an amino acid sequence in which the residue corresponding to X94 is a polar residue, and the residue corresponding to X202 is valine or leucine. In some embodiments, the ketoreductase has an amino acid sequence in which the residue corresponding to X94 is threonine and the residue corresponding to X202 is valine or leucine. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence. In some embodiments, the number of difference can be 1, 2, 3, 4, 5, 6, 7, 8, 9, 10, 11, 12, 14, 15, 16, 18, 20, 22, 24, 26, 30, 35 or about 40 residue differences at other amino acid residues as compared to the reference sequence. In some embodiments, the reference sequence is SEQ ID NO:26 or 28.

In some embodiments, the improved ketoreductase polypeptide comprises an amino acid sequence that is at least about 85%, 86%, 87%, 88%, 89%, 90%, 91%, 92%, 93%, 94%, 95%, 96%, 97%, 98%, or 99% or more identical to a reference sequence based on SEQ ID NO:2, 4 or 86 having the following features: residue corresponding to X94 is an aliphatic or polar residue, particularly alanine or threonine; residue corresponding to X199 is an aliphatic, constrained or polar residue, particularly alanine, asparagine, or histidine; and residue corresponding to X202 is valine or leucine; with the proviso that the ketoreductase polypeptide has an amino acid sequence having at least the preceding features (i.e., the residue corresponding to X94 is an aliphatic or polar residue; the residue corresponding to X199 is an aliphatic, constrained or polar residue; and the residue corresponding to X202 is valine or leucine). In some embodiments, the residue corresponding to X94 is a polar residue; the residue corresponding to X199 is an aliphatic, constrained or polar residue; and the residue corresponding to X202 is valine or leucine. In some embodiments, the ketoreductase has an amino acid sequence in which the residue corresponding to X94 is threonine; residue corresponding to X199 is alanine, asparagine, or histidine; and the residue corresponding to X202 is valine or leucine. In some embodiments, these ketoreductase polypeptides can have one or more residue differences at other residue positions as compared to the reference amino acid sequence. The differences include various modifications, such as substitutions, deletions, and insertions. The substitutions can be non-conservative substitutions, conservative substitutions, or a combination of non-conservative and conservative substitutions. In some embodiments, these ketoreductase polypeptides can have optionally from about 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence. In some embodiments, the number of difference can be 1, 2, 3, 4, 5, 6, 7, 8, 9, 10, 11, 12, 14, 15, 16, 18, 20, 22, 24, 26, 30, 35 or about 40 residue differences at other amino acid residues as compared to the reference sequence. In some embodiments, the reference sequence is SEQ ID NO:22, 24 or 30.

In view of the foregoing, the 2S,3R selective ketoreductases can be described with respect to features of the various combinations of residues corresponding to X94, X199, and X202. For instance, a 2S,3R selective polypeptide characterized by features at residues corresponding to X94 and X202 refer to the descriptions provided herein for the combination of the specified residue positions. Similarly, a 2S,3R selective polypeptide characterized by features at residues corresponding to X94, X199, and X202 refer to the descriptions provided herein for the combination of the specified residues. As further described below, these ketoreductases can have one or more additional features in the amino acid sequence as compared to a reference sequence.

In some embodiments, a 2S,3R selective ketoreductase polypeptide comprises an amino acid sequence based on the sequence formulas as laid out in SEQ ID NO:83, SEQ ID NO:84, or SEQ ID NO:87 (or a region thereof, such as residues 90-211). SEQ ID NO:84 is based on the wild-type amino acid sequence of the *L. kefir* ketoreductase (SEQ ID NO:4), SEQ ID NO:83 is based on the wild-type amino acid sequence of the *L. brevis* ketoreductase (SEQ ID NO:2), and SEQ ID NO:87 is based on the wild-type amino acid sequence of the *L. minor* ketoreductase (SEQ ID NO:86). SEQ ID NO:83, 84 or 87 specify that the residue corresponding to X94 is an aliphatic or polar residue; residue corresponding to X199 is an aliphatic, constrained or polar residue; and residue corresponding to X202 is valine or leucine. The sequence formula further specifies features for various other residue positions, as described below.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, can have one or more additional features selected from the following: residue corresponding to X2 is a polar, non-polar, or aliphatic residue; residue corresponding to X4 is a basic residue or cysteine; residue corresponding to X11 is a non-polar, aliphatic, or aromatic residue; residue corresponding to X40 is a constrained or basic residue; residue corresponding to X80 is a non-polar, aliphatic, or polar residue; residue corresponding to X86 is a non-polar, aliphatic, or polar residue; residue corresponding to X96 is a polar, aromatic, non-polar, or aliphatic residue; residue corresponding to X105 is a non-polar, aliphatic, basic or acidic residue; residue corresponding to X129 is a non-polar or polar residue; residue corresponding to X147 is an aromatic, non-polar or aliphatic residue; residue corresponding to X153 is a polar, non-polar or aliphatic residue; residue corresponding to X190 is an aromatic or constrained residue; residue corresponding to X195 is a non-polar or aliphatic residue; residue corresponding to X196 is a non-polar or aliphatic residue; residue corresponding to X206 is a non-polar or aromatic residue; residue corresponding to X226 is a non-polar or aliphatic residue; residue corresponding to X248 is a non-polar or basic residue; residue corresponding to X249 is an aromatic residue. In some embodiments, the amino acid sequence can have at least two, three, four, five, six or more of the features. In some embodiments, the polypeptides comprising an amino acid sequence that is based on the sequence formula of SEQ ID NO:83, 84 or 87 (or region thereof) can have additionally one or more residue differences at residue positions not specified by an X above as compared to the reference sequence of SEQ ID NO:2, 4 or 86. In some embodiments, the differences can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions not defined by X above. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations.

In some embodiments, the polypeptides comprising an amino acid sequence based on the sequence formula of SEQ ID NO:83, 84 or 87, or region thereof, such as residues 90-211, can have one or more conservative mutations as compared to the amino acid sequences of SEQ ID NO: 2, 4 or 86. Exemplary conservative mutations include amino acid replacements such as, but not limited to: replacement of residue corresponding to X21 valine (V) with another aliphatic residue, e.g., isoleucine; replacement of residue corresponding to X78 glutamic acid (E) with another acidic residue, e.g., aspartic acid; replacement of residue corresponding to X145 glutamic acid (E) with another acidic residue, e.g., aspartic acid; replacement of residue corresponding to X153 leucine (L) with another aliphatic residue, e.g., alanine; replacement of residue corresponding to X195 leucine (L) with another aliphatic residue, e.g., valine; replacement of residue corresponding to X196 with another aliphatic residue, e.g., leucine; replacement of residue corresponding to X226 isoleucine (I) with another aliphatic residue, e.g., valine.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, can have one or more additional features selected from the following: residue corresponding to X2 is a serine, threonine, glutamine, or asparagine, glycine, methionine, alanine, valine, leucine, or isoleucine, particularly serine, threonine, or alanine; residue corresponding to X4 is an arginine, or lysine, or cysteine, particularly arginine or cysteine; residue corresponding to X11 is a glycine, methionine, alanine, valine, leucine, isoleucine, tyrosine, phenylalanine, or tryptophan, particularly isoleucine, leucine, or phenylalanine; residue corresponding to X40 is proline, histidine, arginine, or lysine, particularly histidine or arginine; residue corresponding to X80 is glycine, methionine, alanine, valine, leucine, isoleucine, serine, threonine, glutamine, or asparagine, particularly alanine or threonine; residue corresponding to X86 is serine, threonine, glutamine, asparagine, glycine, methionine, alanine, valine, leucine, or isoleucine, particularly threonine or isoleucine; residue corresponding to X96 is serine, threonine, glutamine, asparagine, glycine, methionine, alanine, valine, leucine, isoleucine, tyrosine, phenylalanine, or tryptophan, particularly serine, asparagine, valine, or phenylalanine; residue corresponding to X105 is glycine, methionine, alanine, valine, leucine, isoleucine, arginine, lysine, aspartic acid, or glutamic acid, particularly glutamic acid, lysine, alanine, or glycine; residue corresponding to X129 is glycine, methionine, alanine, valine, leucine, isoleucine, serine, threonine, glutamine, or asparagine, particularly methionine or threonine; residue corresponding to X147 is tyrosine, phenylalanine, tryptophan, glycine, methionine, alanine, valine, leucine, or isoleucine, particularly phenylalanine, methionine, or leucine; residue corresponding to X153 is a serine, threonine, glutamine, asparagine, glycine, methionine, alanine, valine, leucine, or isoleucine, particularly leucine, alanine, or serine; residue corresponding to X190 is tyrosine, phenylalanine, tryptophan, histidine, or proline, particularly tyrosine, histidine or proline; residue corresponding to X195 is glycine, methionine, alanine, valine, leucine, or isoleucine, particularly leucine or valine; residue corresponding to X196 is glycine, methionine, alanine, valine, leucine, or isoleucine, particularly leucine; residue corresponding to X206 is glycine, methionine, alanine, valine, leucine, isoleucine, tyrosine, phenylalanine, or tryptophan, particularly methionine or phenylalanine; residue corresponding to X226 is glycine, methionine, alanine, valine, leucine or isoleucine, particularly isoleucine or valine; residue corresponding to X248 is glycine, methionine, alanine, valine, leucine, isoleucine, lysine, or arginine, particularly glycine, lysine, or arginine; and residue corresponding to X249 is tyrosine, phenylalanine, or tryptophan, particularly tyrosine or tryptophan. In some embodiments, the amino acid sequence can have at least two, three, four, five, six or more of the features. In some embodiments, the polypeptides comprising an amino acid sequence that is based on the sequence formula of SEQ ID NO:83, 84 or 87 (or region thereof) can have additionally one or more residue differences at residue positions not specified by an X above as compared to the reference sequence of SEQ ID NO:2, 4 or 86. In some embodiments, the differences can be 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions not defined by X above. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, can have additionally one or more or at least all of the following features: residue corresponding to X40 is a constrained or basic residue, particularly arginine; residue corresponding to X147 is an aromatic, non-polar or aliphatic residue, particularly methionine or leucine. In some embodiments, the ketoreductase polypeptide can have in addition to the foregoing features, one or more of the following features: residue corresponding to X96 is a polar, aromatic, non-polar, or aliphatic residue particularly phenylalanine or valine; residue corresponding to X195 is a non-polar or aliphatic residue, particularly valine; residue corresponding to X196 is a non-polar or aliphatic residue, particularly leucine; residue corresponding to X226 is a non-polar or aliphatic residue, particularly valine; residue corresponding to X248 is a non-polar or basic residue, particularly arginine or lysine; and residue corresponding to X249 is an aromatic residue, particularly tryptophan. In some embodiments, the ketoreductase polypeptide can have in addition to the foregoing features, one or more of the following features: residue corresponding to X2 is a polar, non-polar, or aliphatic residue, particularly alanine; residue corresponding to X4 is a basic residue or cysteine, particularly cysteine; residue corresponding to X11 is a non-polar, aliphatic, or aromatic residue, particularly phenylalanine; residue corresponding to X80 is a non-polar, aliphatic, or polar residue, particularly threonine; residue corresponding to X86 is a non-polar, aliphatic, or polar residue, particularly isoleucine; residue corresponding to X105 is a non-polar, aliphatic, basic or acidic residue, particularly glycine; residue corresponding to X129 is a non-polar or polar residue, particularly threonine; residue corresponding to X153 is a polar, non-polar or aliphatic residue, particularly alanine; residue corresponding to X190 is an aromatic or constrained residue, particularly histidine or proline; and residue corresponding to X206 is a non-polar or aromatic residue, particularly phenylalanine. As will be apparent to the skilled artisan, various combinations of the features in the foregoing can be used to form the ketoreductases of the disclosure.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, can have additionally one or more or at least all of the following features: residue corresponding to X40 is a constrained or basic residue, particularly arginine; and residue corresponding to X147 is an aromatic, non-polar or aliphatic residue, particularly methionine or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 can have additionally one or more or at least all of the following features: residue corresponding to X96 is a polar, aromatic, non-polar, or aliphatic residue, particularly valine or phenylalanine; and residue corresponding to X147 is an aromatic, non-polar or aliphatic residue, particularly methionine or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 can have additionally one or more or at least all of the following features: residue corresponding to X40 is a constrained or basic residue, particularly arginine; residue corresponding to X96 is a polar, aromatic, non-polar, or aliphatic residue, particularly valine or phenylalanine; and residue corresponding to X147 is an aromatic, non-polar or aliphatic residue, particularly methionine or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 can have additionally one or more or at least all of the following features: residue corresponding to X96 is a polar, aromatic, non-polar, or aliphatic residue, particularly valine or phenylalanine; residue corresponding to X147 is an aromatic, non-polar or aliphatic residue, particularly methionine or leucine; residue corresponding to X195 is a non-polar or aliphatic residue, particularly valine; and residue corresponding to X196 is a non-polar or aliphatic residue, particularly leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X2 is a polar, non-polar, or aliphatic residue, particularly alanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X4 is cysteine or a basic residue, particularly cysteine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X11 is a non-polar, aliphatic, or aromatic residue, particularly phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X40 is a constrained or basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X80 is a non-polar, aliphatic, or polar residue, particularly threonine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X86 is a non-polar, aliphatic, or polar residue, particularly isoleucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X96 is a polar, aromatic, non-polar, or aliphatic residue, particularly phenylalanine or valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X105 is a non-polar, aliphatic, basic or acidic residue, particularly glycine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X129 is a non-polar or polar residue, particularly threonine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X147 s an aromatic, non-polar or aliphatic residue, particularly methionine or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X153 s a polar, non-polar or aliphatic residue, particularly alanine or serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residue positions. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X190 is an aromatic or constrained residue, particularly histidine or proline. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X195 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X196 is a non-polar or aliphatic residue, particularly leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X206 is a non-polar or aromatic residue, particularly phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X226 is a non-polar or aliphatic residue, particularly valine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X248 is a non-polar or basic residue, particularly lysine or arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, further includes at least the following additional feature: residue corresponding to X249 is an aromatic residue, particularly tryptophan. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO: 2, 4 or 86 having the preceding features, with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features for the various combinations of the residues corresponding to X94, X199 and X202 as described herein, can have additionally one or more or at least all of the following features: residue corresponding to X40 is a constrained or basic residue, particularly arginine; residue and residue corresponding to X147 is an aromatic, non-polar or aliphatic residue, particularly methionine or leucine. In some embodiments, the ketoreductase polypeptide can have in addition to the foregoing features, one or more of the following features: residue corresponding to X96 is a polar, aromatic, non-polar, or aliphatic residue particularly valine; residue corresponding to X195 is a non-polar or aliphatic residue, particularly valine; residue corresponding to X196 is a non-polar or aliphatic residue, particularly leucine; residue corresponding to X226 is a non-polar or aliphatic residue, particularly valine; residue corresponding to X248 is a non-polar or basic residue, particularly arginine or lysine; and residue corresponding to X249 is an aromatic residue, particularly tryptophan. In some embodiments, the ketoreductase polypeptide can have in addition to the foregoing features, one or more of the following features: residue corresponding to X2 is a polar, non-polar, or aliphatic residue; residue corresponding to X4 is a basic residue or cysteine; residue corresponding to X11 is a non-polar, aliphatic, or aromatic residue; residue corresponding to X80 is a non-polar, aliphatic, or polar residue; residue corresponding to X86 is a non-polar, aliphatic, or polar residue; residue corresponding to X105 is a non-polar, aliphatic, basic or acidic residue; residue corresponding to X129 is a non-polar or polar residue; residue corresponding to X153 is a polar, non-polar or aliphatic residue; residue corresponding to X190 is an aromatic or constrained residue; and residue corresponding to X206 is a non-polar or aromatic residue. As will be apparent to the skilled artisan, various combinations of the features in the foregoing can be used to form the ketoreductases of the disclosure.

In some embodiments, an improved ketoreductase comprising an amino acid sequence based on the sequence formula of SEQ ID NO:83, 84 or 87, or a region thereof, such as residues 90-211, having the specified features at residue corresponding to X202 as described herein (i.e., valine or leucine), further includes at least the following additional feature: residue corresponding to X153 is a polar, non-polar or aliphatic residue, particularly alanine or serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence based on SEQ ID NO:2, 4 or 86 having the preceding features (e.g., SEQ ID NO:46, 52 or 54). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:46, 52 or 54), with the proviso that the ketoreductase has an amino acid sequence having at least the preceding features.

In some embodiments, an improved ketoreductase comprising an amino acid sequence based on the sequence formula of SEQ ID NO:83, 84 or 87, or a region thereof, such as residues 90-211, having the specified features at residue corresponding to X202 as described herein, further includes at least the following additional feature: residue corresponding to X147 is an aromatic, non-polar or aliphatic residue, particularly methionine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:44). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:44), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residue corresponding to X202 as described herein, further includes at least the following additional features: residue corresponding to X80 is a non-polar, aliphatic, or polar residue, particularly threonine; and residue corresponding to X153 is a polar, non-polar or aliphatic residue, particularly alanine or serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:18). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:18), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X94 and X202 as described herein, further includes at least the following additional features: residue corresponding to X96 is a polar, aromatic, non-polar, or aliphatic residue, particularly phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:16). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:16), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X199 and X202 as described herein, further includes at least the following additional feature: residue corresponding to X153 is a polar, non-polar or aliphatic residue, particularly alanine or serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:42, 50, 56). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:42, 50, 56), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X94, X199 and X202 as described herein, further includes at least the following additional features: residue corresponding to X40 is a constrained or basic residue, particularly arginine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:12). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:12), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X94, X199 and X202 as described herein, further includes at least the following additional features: residue corresponding to X147 is an aromatic, non-polar or aliphatic residue, particularly methionine or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:6). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:6), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X94, X199 and X202 as described herein, further includes at least the following additional features: residue corresponding to X153 is a polar, non-polar or aliphatic residue, particularly alanine or serine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO: 34 or 36). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO: 34 or 36), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X94, X199 and X202 as described herein, further includes at least the following additional features: residue corresponding to X40 is a constrained or basic residue, particularly arginine; and residue corresponding to X147 is an aromatic, non-polar or aliphatic residue, particularly methionine or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:10). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:10), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X94, X199 and X202 as described herein, further includes at least the following additional features: residue corresponding to X105 is a non-polar, aliphatic, basic or acidic residue, particularly glycine; residue corresponding to X153 is a polar, non-polar or aliphatic residue, particularly alanine; and residue corresponding to X206 is a non-polar or aromatic residue, particularly phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residue positions as compared to the reference sequence of SEQ ID NO:2, 4 or 86 having the preceding features (e.g., SEQ ID NO:38). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:38), with the proviso that the ketoreductase amino acid sequence has at least the preceding features.

In some embodiments, an improved ketoreductase comprising an amino acid sequence based on the sequence formula of SEQ ID NO:83, 84 or 87, or a region thereof, such as residues 90-211, having the specified features at residues corresponding to X94, X199 and X202 as described herein, further includes at least the following additional features: residue corresponding to X96 is a polar, aromatic, non-polar, or aliphatic residue, particularly serine, valine, or phenylalanine; residue corresponding to X129 is a non-polar or polar residue, particularly threonine; and residue corresponding to X206 is a non-polar or aromatic residue, particularly phenylalanine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35 or about 1-40 residue differences at other amino acid residues as compared to the reference sequence of SEQ ID NO:2, 4 or 86 having the preceding features (e.g., SEQ ID NO:40). In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the ketoreductase polypeptide comprises an amino acid sequence that is at least 85%, 86%, 87%, 88%, 89%, 90%, 91%, 92%, 93%, 94%, 95%, 96%, 97%, 98%, or 99% identical to a reference sequence based on SEQ ID NO:2, 4 or 86 having the preceding features (e.g., SEQ ID NO:40), with the proviso that the ketoreductase amino acid sequence has at least the preceding features.

In some embodiments, the improved ketoreductases of the disclosure comprises an amino acid sequence that has a region or domain corresponding to residues 90-211 of the sequence formula of SEQ ID NO:83, 84 or 87 in which the residue corresponding to X202 is valine or leucine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residue positions as compared to the corresponding domain of a reference sequence based on SEQ ID NO: 2, 4 or 86. In some embodiments, the number of differences can be 1, 2, 3, 4, 5, 6, 7, 8, 9, 10, 11, 12, 14, 15, 16, 18, or about 20 residue differences. In some embodiments, the differences comprise conservative mutations. In some embodiments, the ketoreductase polypeptide comprises an amino acid sequence with a domain or region that is at least 85%, 86%, 87%, 88%, 89%, 90%, 91%, 92%, 93%, 94%, 95%, 96%, 97%, 98%, or 99% identical to the domain or region corresponding to residue 90-211 of a reference sequence based on SEQ ID NO: 2, 4 or 86 having the preceding features at residue corresponding to X202, with the proviso that the ketoreductase domain or region comprises an amino acid sequence having at least the preceding feature.

In some embodiments, the improved ketoreductases of the disclosure comprises an amino acid sequence that has a region or domain corresponding to residues 90-211 of the sequence formula of SEQ ID NO:83, 84 or 87 in which the region or domain has the following features: residue corresponding to X94 is an aliphatic or polar residue, particularly alanine or threonine; and residue corresponding to X202 is a valine or leucine. In some embodiments, the ketoreductase has an amino acid sequence in which the residue corresponding to X94 is a polar residue, and the residue corresponding to X202 is valine or leucine. In some embodiments, the ketoreductase has an amino acid sequence in which the residue corresponding to X94 is threonine, and the residue corresponding to X202 is valine or leucine In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residue positions as compared to the corresponding domain of a reference sequence based on SEQ ID NO: 2, 4 or 86. In some embodiments, the number of differences can be 1, 2, 3, 4, 5, 6, 7, 8, 9, 10, 11, 12, 14, 15, 16, 18, or about 20 residue differences. In some embodiments, the differences comprise conservative mutations. In some embodiments, the ketoreductase polypeptide comprises an amino acid sequence with a domain or region that is at least 85%, 86%, 87%, 88%, 89%, 90%, 91%, 92%, 93%, 94%, 95%, 96%, 97%, 98%, or 99% identical to the domain or region corresponding to residues 90-211 of a reference sequence based on SEQ ID NO: 2, 4 or 86 having the preceding features, with the proviso that the ketoreductase domain or region comprises an amino acid sequence having at least the preceding features.

In some embodiments, the improved ketoreductases of the disclosure comprises an amino acid sequence that has a region or domain corresponding to residues 90-211 of the sequence formula of SEQ ID NO:83, 84 or 87 having the following features: residue corresponding to X94 is an aliphatic or polar residue, particularly alanine or threonine; residue corresponding to X199 is an aliphatic, constrained or polar residue, particularly alanine, asparagine, or histidine; and residue corresponding to X202 is a valine or leucine. In some embodiments, the residue corresponding to X94 is a polar residue; the residue corresponding to X199 is an aliphatic, constrained, or polar residue; and the residue corresponding to X202 is valine or leucine. In some embodiments, the ketoreductase has an amino acid sequence in which the residue corresponding to X94 is threonine; residue corresponding to X199 is alanine, asparagine, or histidine; and the residue corresponding to X202 is valine or leucine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residue positions as compared to the corresponding domain of a reference sequence based on SEQ ID NO: 2, 4 or 86. In some embodiments, the number of differences can be 1, 2, 3, 4, 5, 6, 7, 8, 9, 10, 11, 12, 14, 15, 16, 18, or about 20 residue differences. In some embodiments, the differences comprise conservative mutations. In some embodiments, the ketoreductase polypeptide comprises an amino acid sequence with a domain or region that is at least 85%, 86%, 87%, 88%, 89%, 90%, 91%, 92%, 93%, 94%, 95%, 96%, 97%, 98%, or 99% identical to the domain or region corresponding to residues 90-211 of a reference sequence based on SEQ ID NO: 2, 4 or 86 having the preceding features, with the proviso that the ketoreductase domain or region comprises an amino acid sequence having at least the preceding features.

In some embodiments, the ketoreductase polypeptide with a domain or region corresponding to residues 90-211 of the sequence formula of SEQ ID NO:83, 84 or 87 and having the specified features for the various combination of residues corresponding to residues X94, X199, and X202 as described herein, can further include in the region or domain one or more of the features selected from the following: residue corresponding to X96 is a polar, aromatic, non-polar, or aliphatic residue; residue corresponding to X105 is a non-polar, aliphatic, basic or acidic residue; residue corresponding to X129 is a non-polar or polar residue; residue corresponding to X147 is an aromatic, non-polar or aliphatic residue; residue corresponding to X153 is a polar, non-polar or aliphatic residue; residue corresponding to X190 is an aromatic or constrained residue; residue corresponding to X195 is a non-polar or aliphatic residue; residue corresponding to X196 is a non-polar or aliphatic residue; and residue corresponding to X206 is a non-polar or aromatic residue. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residues not specified by X above as compared to the corresponding domain of a reference sequence based on SEQ ID NO: 2, 4 or 86. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductases polypeptides having a domain or region with an amino acid sequence corresponding to residues 90-211 of the sequence formula of SEQ ID NO:83, 84 or 87, as described above, can have one or more conservative mutations in the domain or region as compared to the amino acid sequence of the corresponding domain of SEQ ID NO: 2, 4 or 86. Examples of such conservative mutations include amino acid replacements such as, but limited to: replacement of residue corresponding to X145 glutamic acid (E) with another acidic residue, e.g., aspartic acid; replacement of residue corresponding to X153 leucine (L) with another aliphatic residue, e.g., alanine; replacement of residue corresponding to X195 leucine (L) with another aliphatic residue, e.g., valine; and replacement of residue corresponding to X196 with another aliphatic residue, e.g., leucine.

In some embodiments, the ketoreductase polypeptide with a domain or region corresponding to residues 90-211 of the sequence formula of SEQ ID NO:83, 84 or 87 and having the specified features for the various combination of residues corresponding to residues X94, X199, and X202 as described herein, can further include in the region or domain one or more of the features selected from the following: residue corresponding to X96 is serine, threonine, glutamine, asparagine, glycine, methionine, alanine, valine, leucine, isoleucine, tyrosine, phenylalanine, or tryptophan, particularly asparagine, serine, valine, or phenylalanine; residue corresponding to X105 is glycine, methionine, alanine, valine, leucine, isoleucine, arginine, lysine, aspartic acid, or glutamic acid, particularly glutamic acid, lysine, alanine, or glycine; residue corresponding to X129 is glycine, methionine, alanine, valine, leucine, isoleucine, serine, threonine, glutamine, or asparagine, particularly methionine or threonine; residue corresponding to X147 is tyrosine, phenylalanine, tryptophan, glycine, methionine, alanine, valine, leucine, or isoleucine, particularly phenylalanine, methionine, or leucine; residue corresponding to X153 is a serine, threonine, glutamine, asparagine, glycine, methionine, alanine, valine, leucine, or isoleucine, particularly leucine, alanine, or serine; residue corresponding to X190 is tyrosine, phenylalanine, tryptophan, histidine, or proline, particularly tyrosine, histidine or proline; residue corresponding to X195 is glycine, methionine, alanine, valine, leucine, or isoleucine, particularly leucine or valine; residue corresponding to X196 is glycine, methionine, alanine, valine, leucine, or isoleucine, particularly leucine; residue corresponding to X206 is glycine, methionine, alanine, valine, leucine, isoleucine, tyrosine, phenylalanine, or tryptophan, particularly methionine or phenylalanine. In some embodiments, the region or domain corresponding to residues 90-211 can have additionally from about 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residue positions not specified by X above as compared to the corresponding domain of a reference sequence based on SEQ ID NO: 2, 4 or 86. In some embodiments, the number of differences can be 1, 2, 3, 4, 5, 6, 7, 8, 9, 10, 11, 12, 14, 15, 16, 18, or about 20 residue differences at other amino acid residues in the domain. In some embodiments, the differences comprise conservative mutations.

In some embodiments, the ketoreductase polypeptide with a domain or region corresponding to residues 90-211 of the sequence formula of SEQ ID NO:83, 84 or 87 and having the specified features for the various combination of residues corresponding to residues X94, X199, and X202 as described herein, can further include in the region or domain the following feature: residue corresponding to X147 is an aromatic, non-polar or aliphatic residue, particularly methionine or leucine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residue positions as compared to the corresponding domain of a reference sequence based on SEQ ID NO: 2, 4 or 86. In some embodiments, the number of differences can be 1, 2, 3, 4, 5, 6, 7, 8, 9, 10, 11, 12, 14, 15, 16, 18, or about 20 residue differences. In some embodiments, the differences comprise conservative mutations. In some embodiments, the ketoreductase polypeptide comprises an amino acid sequence with a domain or region that is at least 85%, 86%, 87%, 88%, 89%, 90%, 91%, 92%, 93%, 94%, 95%, 96%, 97%, 98%, or 99% identical to the domain or region corresponding to residues 90-211 of a reference sequence based on SEQ ID NO: 2, 4 or 86 having the preceding features, with the proviso that the ketoreductase domain or region comprises an amino acid sequence having at least the preceding features.

In some embodiments, the ketoreductase polypeptide with a domain or region corresponding to residues 90-211 of the sequence formula of SEQ ID NO:83, 84 or 87 and having the specified features for the various combination of residues corresponding to residues X94, X199, and X202 as described herein, can further include in the region or domain the following feature: residue corresponding to X96 is a polar, aromatic, non-polar, or aliphatic residue, particularly valine or phenylalanine; and residue corresponding to X147 is an aromatic, non-polar or aliphatic residue, particularly methionine or leucine. In some embodiments, the region or domain corresponding to residues 90-211 can have additionally 1-2, 1-3, 1-4, 1-5, 1-6, 1-7, 1-8, 1-9, 1-10, 1-11, 1-12, 1-14, 1-15, 1-16, 1-18, or 1-20 residue differences at other amino acid residue positions as compared to the corresponding domain of a reference sequence based on SEQ ID NO: 2, 4 or 86. In some embodiments, the number of differences can be 1, 2, 3, 4, 5, 6, 7, 8, 9, 10, 11, 12, 14, 15, 16, 18, or about 20 residue differences. In some embodiments, the differences comprise conservative mutations. In some embodiments, the ketoreductase polypeptide comprises an amino acid sequence with a domain or region that is at least 85%, 86%, 87%, 88%, 89%, 90%, 91%, 92%, 93%, 94%, 95%, 96%, 97%, 98%, or 99% identical to the domain or region corresponding to residues 90-211 of a reference sequence based on SEQ ID NO: 2, 4 or 86 having the preceding features, with the proviso that the ketoreductase domain or region comprises an amino acid sequence having at least the preceding features.

In some embodiments, the ketoreductase polypeptide can further comprise a domain or region corresponding to residues 1-89 of the sequence formula of SEQ ID NO:83, 84 or 87, where the domain or region can have one or more of the following features: residue corresponding to X2 is a polar, non-polar, or aliphatic residue; residue corresponding to X4 is a basic residue or cysteine; residue corresponding to X11 is a non-polar, aliphatic, or aromatic residue; residue corresponding to X40 is a constrained or basic residue; residue corresponding to X80 is a non-polar, aliphatic, or polar residue; and residue corresponding to X86 is a non-polar, aliphatic, or polar residue. In some embodiments, the polypeptides comprising a region or domain corresponding to residues 1-89 of the sequence formula of SEQ ID NO:83, 84 or 87 can have additionally one or more residue differences at residue positions not specified by X above as compared to the reference sequence of SEQ ID NO: 2, 4 or 86. In some embodiments, the differences can be 1-2, 1-3, 1-4, 1-5, 1-6, 1-7, 1-8, 1-9, 1-10, 1-11, 1-12, 1-14, 1-15, or 1-16 residue differences at other amino acid residue positions not defined by X above as compared to the reference sequence of SEQ ID NO: 2, 4 or 86. In some embodiments, the number of differences can be 1, 2, 3, 4, 5, 6, 7, 8, 9, 10, 11, 12, 14, 15, or 16 residue differences at other amino acid residue positions. In some embodiments, the differences comprise conservative mutations.

In some embodiments, the ketoreductase polypeptide can further comprise a domain or region corresponding to residues 1-89 of the sequence formula of SEQ ID NO:83, 84 or 87, where the domain or region can have one or more of the following features: residue corresponding to X2 is a serine, threonine, glutamine, or asparagine, glycine, methionine, alanine, valine, leucine, or isoleucine, particularly serine, threonine, or alanine; residue corresponding to X4 is an arginine, or lysine, or cysteine, particularly arginine or cysteine; residue corresponding to X11 is a glycine, methionine, alanine, valine, leucine, isoleucine, tyrosine, phenylalanine, or tryptophan, particularly isoleucine, leucine, or phenylalanine; residue corresponding to X40 is proline, histidine, arginine, or lysine, particularly histidine or arginine; residue corresponding to X80 is glycine, methionine, alanine, valine, leucine, isoleucine, serine, threonine, glutamine, or asparagine, particularly alanine or threonine; and residue corresponding to X86 is serine, threonine, glutamine, asparagine, glycine, methionine, alanine, valine, leucine, or isoleucine, particularly threonine or isoleucine. In some embodiments, the polypeptides comprising a region or domain corresponding to residues 1-89 of the sequence formula of SEQ ID NO:83, 84 or 87 can have additionally one or more residue differences at residue positions not specified by X above as compared to the reference sequence of SEQ ID NO: 2, 4 or 86. In some embodiments, the differences can be 1-2, 1-3, 1-4, 1-5, 1-6, 1-7, 1-8, 1-9, 1-10, 1-11, 1-12, 1-14, 1-15, or 1-16 residue differences at other amino acid residue positions not defined by X above as compared to the reference sequence of SEQ ID NO: 2, 4 or 86. In some embodiments, the number of differences can be 1, 2, 3, 4, 5, 6, 7, 8, 9, 10, 11, 12, 14, 15, or 16 residue differences at other amino acid residue positions. In some embodiments, the differences comprise conservative mutations.

In some embodiments, the ketoreductase polypeptide can further comprise a domain or region corresponding to residues 1-89 of the sequence formula of SEQ ID NO:83, 84 or 87, where the domain or region can have at least the following feature: residue corresponding to X40 is a constrained or basic residue, particularly arginine. In some embodiments, the polypeptides comprising a region or domain corresponding to residues 1-89 of the sequence formula of SEQ ID NO: 111, 112, or 139 can have additionally one or more residue differences at other residue positions as compared to the reference sequence of SEQ ID NO: 2, 4 or 114. In some embodiments, the region or domain corresponding to residues 1-89 can have additionally 1-2, 1-3, 1-4, 1-5, 1-6, 1-7, 1-8, 1-9, 1-10, 1-11, 1-12, 1-14, 1-15, or 1-16 residue differences at other amino acid residue positions as compared to the corresponding domain or region of a reference sequence based on SEQ ID NO:2, 4 or 86. In some embodiments, the number of differences can be 1, 2, 3, 4, 5, 6, 7, 8, 9, 10, 11, 12, 14, 15, or about 16 residue differences at other amino acid residues in the domain. In some embodiments, the differences comprise conservative mutations. In some embodiments, the ketoreductase region or domain comprises an amino acid sequence having at least the preceding feature, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 1-89 of a reference sequence based on SEQ ID NO:2, 4 or 86 having the preceding features.

In some embodiments, the ketoreductase polypeptide can further comprise a domain or region corresponding to residues 212-252 of the sequence formula of SEQ ID NO:83, 84 or 87, where the domain or region can have one or more of the following features: residue corresponding to X226 is a non-polar or aliphatic residue; residue corresponding to X248 is a non-polar or basic residue; and residue corresponding to X249 is an aromatic residue. In some embodiments, the polypeptides comprising a region or domain corresponding to residues 212-252 of the sequence formula of SEQ ID NO:83, 84 or 87 can have additionally one or more residue differences at residue positions not specified by X above as compared to the reference sequence of SEQ ID NO: 2, 4 or 86. In some embodiments, the differences can be 1-2, 1-3, 1-4, 1-5, 1-6, 1-7, 1-8, 1-9, or 1-10 residue differences at other amino acid residue positions not defined by X above as compared to the reference sequence of SEQ ID NO: 2, 4 or 86. In some embodiments, the number of differences can be 1, 2, 3, 4, 5, 6, 7, 8, 9, or 10 residue differences at other amino acid residue positions. In some embodiments, the differences comprise conservative mutations.

In some embodiments, the ketoreductase polypeptide can further comprise a domain or region corresponding to residues 212-252 of the sequence formula of SEQ ID NO:83, 84 or 87, where the domain or region can have one or more of the following features: residue corresponding to X226 is glycine, methionine, alanine, valine, leucine or isoleucine, particularly valine; residue corresponding to X248 is glycine, methionine, alanine, valine, leucine, isoleucine, lysine, or arginine, particularly glycine, lysine, or arginine; and residue corresponding to X249 is tyrosine, phenylalanine, or tryptophan, particularly tyrosine or tryptophan. In some embodiments, the polypeptides comprising a region or domain corresponding to residues 212-252 of the sequence formula of SEQ ID NO:83, 84 or 87 can have additionally one or more residue differences at residue positions not specified by X above as compared to the reference sequence of SEQ ID NO: 2, 4 or 86. In some embodiments, the differences can be 1-2, 1-3, 1-4, 1-5, 1-6, 1-7, 1-8, 1-9, or 1-10 residue differences at other amino acid residue positions not defined by X above as compared to the reference sequence of SEQ ID NO: 2, 4 or 86. In some embodiments, the number of differences can be 1, 2, 3, 4, 5, 6, 7, 8, 9, or 10 residue differences at other amino acid residue positions. In some embodiments, the differences comprise conservative mutations.

In some embodiments, the ketoreductase polypeptide can further comprise a domain or region corresponding to residues 212-252 of the sequence formula of SEQ ID NO:83, 84 or 87, where the domain or region has at least the following feature: residue corresponding to X226 is a non-polar or aliphatic residue, particularly valine. In some embodiments, the polypeptide comprising a region or domain corresponding to residues 212-252 of the sequence formula of SEQ ID NO:83, 84 or 87, can have additionally one or more residue differences at other residue positions as compared to the reference sequence of SEQ ID NO: 2, 4 or 86 having the preceding features. In some embodiments, the region or domain corresponding to residues 212-252 can have additionally 1-2, 1-3, 1-4, 1-5, 1-6, 1-7, 1-8, 1-9, or 1-10 residue differences at other amino acid residue positions as compared to the corresponding domain of the reference sequence based on SEQ ID NO:2, 4 or 86. In some embodiments, the number of differences can be 1, 2, 3, 4, 5, 6, 7, 8, 9, or about 10 residue differences at other amino acid residues in the domain. In some embodiments, the differences comprise conservative mutations. In some embodiments, the ketoreductase region or domain comprises an amino acid sequence having at least the preceding features, and wherein the amino acid sequence has at least 85%, 86%, 87%, 88%, 89%, 90%, 91%, 92%, 93%, 94%, 95%, 96%, 97%, 98%, or 99% identity as compared to the amino acid sequence corresponding to residues 212-252 of a reference sequence based on SEQ ID NO:2, 4 or 86 having the preceding features.

Table 2 below provides exemplary 2S,3R selective ketoreductases, SEQ ID NOs: 1-62, with their associated activities. The sequences below are derived from the wild-type *L. kefir* ketoreductase sequences (SEQ ID NO: 3 and 4) unless otherwise specified. In Table 2 below, each row lists two SEQ ID NOs, where the odd number refers to the nucleotide sequence that codes for the amino acid sequence provided by the even number. The column listing the # of mutations is with respect to the number of amino acid substitutions as compared to the *L. kefir* KRED amino acid sequence of SEQ ID NO:4, and the specific substitutions are listed in the column "mutations from *kefir*." In the activity column, one "+" corresponds to a 1-15 fold improvement as compared to the ability of the polypeptide having the amino acid sequence of SEQ ID NO:48 to convert the substrate to the product of formula (II). Two plus signs "++" indicates that the polypeptide is about 15 to 30 fold improved as compared to SEQ ID NO:48. Three plus signs "+++" indicates that the polypeptide is about 30 to 40 fold improved as compared to SEQ ID NO:48. Four plus signs "++++" indicates that the polypeptide is about 40 to 50 fold improved as compared to SEQ ID NO:48, and five plus signs "+++++" indicates that the polypeptide is greater than 50 fold improved as compared to SEQ ID NO:48. A "+" sign under the stability column indicates that the polypeptide is capable of retaining enzymatic activity for converting the substrate to the product of formula (II) after 21 hours of heat treatment at 40° C. For the selectivity column, a single plus sign "+" indicates that the polypeptide is able to convert the substrate to the product of formula (II) with about 60-89% stereomeric excess; two plus signs "++" indicates that the polypeptide is able to convert the substrate to the product of formula (II) with about 90-94% stereomeric excess; three plus signs "+++" indicates that the polypeptide is able to convert the substrate to the product of formula (II) with about 95-99% stereomeric excess; and four plus signs "+++" indicates that the polypeptide is able to convert the substrate to the product of formula (II) with greater than about 99% stereomeric excess. Accordingly, in some embodiments, the 2S,3R selective ketoreductases can comprise a sequence corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, or 62.

TABLE 2

Table 2: List of Sequences and Corresponding Activity Improvement

| SEQ ID NO | Residue Differences from SEQ ID NO: 2 | # of mutations from kefir | Activity | Stability | Selectivity |
|---|---|---|---|---|---|
| 1/2 | L. brevis | | | | |
| 3/4 | L. kefir | | | | |
| 47/48 | A202V | 1 | improved over wt | | + |
| 37/38 | A94T; E105G; L153A; L199A; A202L; M206F | 6 | + | | + |
| 15/16 | A94T; S96F; A202V | 3 | + | | +++ |
| 55/56 | L153A; L199A; A202L | 3 | + | | +++ |
| 57/58 | T86I; L199N; A202L | 3 | + | | +++ |
| 51/52 | L153A; A202L | 2 | + | | +++ |
| 53/54 | L153A; A202V | 2 | + | | + |
| 31/32 | A94T; L199A; A202V | 3 | ++ | | ++++ |
| 33/34 | A94T; L153A; L199H; A202L | 4 | +++ | | ++++ |
| 49/50 | L153A; L199H; A202L | 3 | ++ | | +++ |
| 19/20 | A94T; L199N; A202V | 3 | +++ | | ++++ |
| 45/46 | L153S; A202L | 2 | + | | + |
| 35/36 | A94T; L153A; L199A; A202V | 4 | + | | ++ |
| 25/26 | A94T; A202L | 2 | +++ | | +++ |
| 27/28 | A94T; A202V | 2 | ++ | | +++ |
| 29/30 | A94T; L199A; A202L | 3 | +++ | | ++++ |
| 21/22 | A94T; L199H; A202L | 3 | ++++ | | ++++ |
| 23/24 | A94T; L199H; A202V | 3 | +++ | | ++++ |
| 41/42 | L153A; L199N; A202L | 3 | + | | +++ |
| 39/40 | A94T; S96F; M129T; A202V; M206F | 5 | + | | ++ |
| 17/18 | A80T; L153A; A202V; | 3 | + | | +++ |
| 43/44 | F147M; A202V | 2 | + | + | |
| 9/10 | H40R; A94T; F147L; L199H; A202L | 5 | +++++ | + | ++++ |
| 11/12 | H40R; A94T; L199H; A202L | 4 | +++++ | | ++++ |
| 5/6 | A94T; F147L; L199H; A202L | 4 | +++++ | + | ++++ |
| 7/8 | A94T; L199H; A202L | 3 | +++++ | | ++++ |
| 59/60 | I11F; H40R; A94F; S96V; F147M; L195V; V196L; L199W; I226V; G248K; Y249W | 11 | ++++ | | ++++ |

TABLE 2-continued

Table 2: List of Sequences and Corresponding Activity Improvement

| SEQ ID NO | Residue Differences from SEQ ID NO: 2 | # of mutations from kefir | Activity | Stability | Selectivity |
|---|---|---|---|---|---|
| 61/62 | T2A; R4C; H40R; A94G; S96V; F147M; V196L; L199W; I226V; G248K; Y249W | 11 | +++ | | ++++ |
| 13/14 | H40R; A94F; S96V; F147M; L195V; V196L; L199W; I226V; Y249W | 9 | ++++ | | ++++ |

In some embodiments, an improved 2S,3R selective ketoreductase comprises an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, or 62, with the proviso that the ketoreductase amino acid sequence has at least the following features: residue corresponding to X94 is an aliphatic or polar residue, particularly alanine or threonine; residue corresponding to X199 is an aliphatic, constrained or polar residue, particularly alanine, histidine, or asparagine; and residue corresponding to X202 is valine or leucine. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, an improved 2S,3R selective ketoreductase comprises an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, or 62, with the proviso that the ketoreductase amino acid sequence comprises any one of the set of mutations contained in any one of the polypeptide sequences listed in Table 2 as compared to SEQ ID NO:2 or 4 or 86. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 85% or with a percent stereomeric excess that is greater than the wild-type L. kefir KRED (SEQ ID NO:4). Exemplary polypeptides that are capable include, but are not limited to, polypeptides comprising an amino acid sequence corresponding to SEQ ID NO: 6, 8, 10, 12, 14, 16, 18, 20, 22, 24, 26, 28, 30, 32, 34, 36, 38, 40, 42, 44, 46, 48, 50, 52, 54, 56, 58, 60, or 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 60-89% and at a rate that is at least about 1-15 fold greater than the rate capable by the polypeptide having the amino acid sequence of SEQ ID NO:48. Exemplary polypeptides that are capable include, but are not limited to, polypeptides comprising an amino acid sequence corresponding to SEQ ID NO: 6, 8, 10, 12, 14, 16, 18, 20, 22, 24, 26, 28, 30, 32, 34, 36, 38, 40, 42, 46, 50, 52, 54, 56, 58, 60, or 62. Because the reference polypeptide having the amino acid sequence of SEQ ID NO:48 is capable of converting the substrate to the product at a rate (for example, 100% conversion in 20 hours of 1 g/L substrate with about 10 g/L of the KRED, in 50% IPA at pH 8) and with a stereoselectivity that is improved over wild-type (SEQ ID NO:4), the polypeptides herein that are improved over SEQ ID NO:48 are also improved over wild-type.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 90-94%. Exemplary polypeptides that are capable include, but are not limited to, polypeptides comprising an amino acid sequence corresponding to SEQ ID NO: 6, 8, 10, 12, 14, 16, 18, 20, 22, 24, 26, 28, 30, 32, 34, 36, 40, 42, 50, 52, 56, 58, 60, or 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 95-99%. Exemplary polypeptides that are capable include, but are not limited to, polypeptides comprising an amino acid sequence corresponding to SEQ ID NO: 6, 8, 10, 12, 14, 16, 18, 20, 22, 24, 26, 28, 30, 32, 34, 42, 50, 52, 56, 58, 60, or 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, with a percent stereomeric excess of at least about 99%. Exemplary polypeptides that are capable include, but are not limited to, polypeptides comprising an amino acid sequence corresponding to SEQ ID NO:6, 8, 10, 12, 14, 20, 22, 24, 30, 32, 34, 60, or 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 15-30 fold greater than the rate capable by the polypeptide having the amino acid sequence of SEQ ID NO:48. Exemplary polypeptides that are capable include, but are not limited to, polypeptides comprising an amino acid sequence corresponding to SEQ ID NO: 6, 8, 10, 12, 14, 20, 22, 24, 26, 28, 30, 32, 34, 50, 60, or 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 30-40 fold greater than the rate capable by the polypeptide having the amino acid sequence of SEQ ID NO:48. Exemplary polypeptides that are capable include, but are not limited to, polypeptides comprising an amino acid sequence corresponding to SEQ ID NO: 6, 8, 10, 12, 14, 20, 22, 24, 26, 30, 34, 60, or 62.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 40-50 fold greater than the rate capable by the polypeptide having the amino acid sequence of SEQ ID NO:48. Exemplary polypeptides that are capable include, but are not limited to, polypeptides comprising an amino acid sequence corresponding to SEQ ID NO: 6, 8, 10, 12, 14, 22, or 60.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 50 fold greater than the rate capable by the polypeptide having the amino acid sequence of SEQ ID NO:48. Exemplary polypeptides that are capable include, but are not limited to, polypeptides comprising an amino acid sequence corresponding to SEQ ID NO: 6, 8, 10, or 12.

In some embodiments, the ketoreductase polypeptides are capable of converting the substrate, methyl-2-benzamidomethyl-3-oxobutyrate, to the product, 2S,3R-methyl-2-benzamidomethyl-3-hydroxybutyrate, at a rate that is at least about 50 fold greater than the rate capable by the polypeptide having the amino acid sequence of SEQ ID NO:48 and with a stereomeric excess of at least 99%. Exemplary polypeptides that are capable include, but are not limited to, polypeptides comprising an amino acid sequence corresponding to SEQ ID NO: 6, 8, 10, and 12.

In some embodiments, the ketoreductase polypeptide are capable of retaining its ability to convert the substrate, methyl-2-benzamidomethyl-3-oxobutyrate, to the product, 2S,3R-methyl-2-benzamidomethyl-3-hydroxybutyrate, after heat treatment at 40° C. for 21 hours. Exemplary polypeptides that are capable include, but are not limited to, polypeptides comprising an amino acid sequence corresponding to SEQ ID NO: 6, 10, or 44.

As noted above, in some embodiments, the ketoreductases are stereoselectively capable of reducing or converting the substrate of formula (I) to the product of formula (III). Table 3 below provides exemplary 2R,3R specific ketoreductases, SEQ ID NOs 63-82, with their associated activities. The sequences below are derived from the wild-type *L. kefir* ketoreductase sequences (SEQ ID NO: 3 and 4) unless otherwise specified. In Table 3 below, each row lists two SEQ ID NOs, where the odd number refers to the nucleotide sequence that codes for the amino acid sequence provided by the even number. The column listing the # of mutations is with respect to the number of amino acid substitutions as compared to the *L. kefir* KRED amino acid sequence of SEQ ID NO:4, and the column "sequence—coding mutations" lists the substitutions as compared to SEQ ID NO:4. In the activity column, one "+" corresponds to an about 1 fold improvement as compared to the ability of the polypeptide having the amino acid sequence of SEQ ID NO:66 to convert the substrate to the product of formula (III). Two plus signs "++" indicates that the polypeptide is greater than about 1 to 2 fold improved as compared to SEQ ID NO:66. Three plus signs "+++" indicates that the polypeptide is greater than about 5 fold improved as compared to SEQ ID NO:66. For the selectivity column, a single plus sign "+" indicates that the polypeptide is able to convert the substrate to the product of formula (III) with less than about 85% stereomeric excess; two plus signs "++" indicates that the polypeptide is able to convert the substrate to the product of formula (III) with greater than about 85% stereomeric excess. Accordingly, in some embodiments, the 2S,3R selective ketoreductases can comprise a sequence corresponding to SEQ ID NO: 64, 66, 68, 70, 72, 74, 76, 78, 80, or 82.

TABLE 3

List of Sequences and Corresponding Activity Improvement

| SEQ ID NO | Residue Differences from SEQ ID NO: 4 | # of mutations from kefir | Activity | Stability |
|---|---|---|---|---|
| 65/66 | H40R; A94G; S96V; E145F; F147M; Y190P; V196L; L199W; I226V; Y249W | 10 | + | + |
| 73/74 | I11F; H40R; A94E; S96V; E145F; F147M; Y190P; L195V; V196L; L199W; I226V; Y249H | 12 | ++ | ++ |
| 81/82 | D3V; A10T; H40R; A94G; S96V; F147M; Y190P; V196L; L199W; I226V; G248K; Y249H | 12 | + | ++ |
| 67/68 | H40R; A94F; S96V; E145F; F147M; Y190P; L195V; V196L; L199W; I226V; G248R; Y249W | 12 | ++ | ++ |
| 77/78 | I11L; H40R; A94E; S96V; F147M; Y190H; V196L; I226V; G248K; Y249H | 10 | +++ | ++ |
| 71/72 | H40R; T54A; A94F; S96V; E105K; E145D; F147M; V196L; L199W; I226V; Y249W | 11 | +++ | ++ |
| 75/76 | I11F; H40R; A94G; S96V; E145F; F147M; Y190H; L195V; V196L; L199W; A202V; I226V; Y249H; A251T | 14 | +++ | ++ |
| 69/70 | H40R; E78D; A94E; S96V; F147M; Y190H; L195V; V196L; I226V; Y249H; T250Y | 11 | +++ | + |
| 79/80 | K8N; V9G; I11F; H40R; A94G; S96V; E145F; F147M; Y190P; V196L; I226V; G248K; Y249R | 13 | +++ | + |
| 63/64 | V12I; H40R; A94E; S96V; F147M; Y190P; L195V; V196L; L199W; I226V; G248R; Y249W | 12 | +++ | + |

In some embodiments, an improved 2R,3R selective ketoreductase comprises an amino acid sequence that is at least about 85%, 86%, 87%, 88%, 89%, 90%, 91%, 92%, 93%, 94%, 95%, 96%, 97%, 98%, or 99% identical to a reference sequence based on SEQ ID NO: 64, 66, 68, 70, 72, 74, 76, 78, 80, or 82, with the proviso that the ketoreductase amino acid sequence comprises any one of the set of mutations contained in any one of the polypeptide sequences listed in Table 3 as compared to SEQ ID NO:2 or 4 or 86. In some embodiments, the ketoreductase polypeptides can have additionally 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 residue differences at other amino acid residue positions as compared to the reference sequence. In some embodiments, the number of differences can be 1, 2, 3, 4, 5, 6, 7, 8, 9, 10, 11, 12, 14, 15, 16, 18, 20, 22, 24, 26, 30, 35 or about 40 residue differences at other amino acid residues. In some embodiments, the differences comprise conservative mutations.

In some embodiments, the 2R,3R selective ketoreductase polypeptides are capable of converting the substrate, methyl-2-benzamidomethyl-3-oxobutyrate, to the product, 2R,3R-methyl-2-benzamidomethyl-3-hydroxybutyrate, with a percent stereomeric excess of at least about 85%. Exemplary polypeptides that are capable include, but are not limited to, polypeptides comprising an amino acid sequence corresponding to SEQ ID NO: 68, 72, 74, 76, 78, or 82.

In some embodiments, the 2R,3R selective ketoreductase polypeptides are capable of converting the substrate, methyl-2-benzamidomethyl-3-oxobutyrate, to the product, 2R,3R-methyl-2-benzamidomethyl-3-hydroxybutyrate, at a rate that is at least about 1 fold greater than the rate capable by the polypeptide having the amino acid sequence of SEQ ID NO:66. Exemplary polypeptides that are capable include, but are not limited to, polypeptides comprising an amino acid sequence corresponding to SEQ ID NO: 64, 68, 70, 72, 74, 76, 78. 80, or 82. Because the polypeptide having the amino acid sequence of SEQ ID NO:66 is capable of capable of converting the substrate, methyl-2-benzamidomethyl-3-oxobutyrate, to the product, 2R,3R-methyl-2-benzamidomethyl-3-hydroxybutyrate, with a stereomeric excess and at a rate that is greater than wild-type L. kefir KRED (SEQ ID NO:4), any polypeptide improved over SEQ ID NO:66 is also improved over wild-type L. kefir KRED.

In some embodiments, the 2R,3R selective ketoreductase polypeptide capable of converting the substrate, methyl-2-benzamidomethyl-3-oxobutyrate, to the product, 2R,3R-methyl-2-benzamidomethyl-3-hydroxybutyrate, at a rate that is at least about 1-2 fold greater than the rate capable by the polypeptide having the amino acid sequence of SEQ ID NO:66. Exemplary polypeptides that are capable include, but are not limited to, polypeptides comprising an amino acid sequence corresponding to SEQ ID NO: 64, 68, 70, 72, 74, 76, 78. or 80.

In some embodiments, the 2R,3R selective ketoreductase polypeptides are capable of converting the substrate, methyl-2-benzamidomethyl-3-oxobutyrate, to the product, 2R, 3R-methyl-2-benzamidomethyl-3-hydroxybutyrate, at a rate that is at least about 5 fold greater than the rate capable by the polypeptide having the amino acid sequence of SEQ ID NO:66. Exemplary polypeptides that are capable include, but are not limited to, polypeptides comprising an amino acid sequence corresponding to SEQ ID NO: 64, 70, 72, 76, 78. or 80.

In some embodiments, the 2R,3R selective ketoreductase polypeptides are capable of converting the substrate, methyl-2-benzamidomethyl-3-oxobutyrate, to the product, 2R,3R-methyl-2-benzamidomethyl-3-hydroxybutyrate, at a rate that is at least about 5 fold greater than the rate capable by the polypeptide having the amino acid sequence of SEQ ID NO:66 and with a stereomeric excess that is at least 85%. Exemplary polypeptides that are capable include, but are not limited to, polypeptides comprising an amino acid sequence corresponding to SEQ ID NO: 72 or 78.

In some embodiments, the 2S,3R selective ketoreductase polypeptides of the disclosure can comprise an amino acid sequence that is at least about 85%, 86%, 87%, 88%, 89%, 90%, 91%, 92%, 93%, 94%, 95%, 96%, 97%, 98%, or 99% identical to SEQ ID NO:2 or SEQ ID NO:4 or SEQ ID NO:86 (or a region or domain thereof, such as residues 90-211) with the proviso that the residues corresponding to residue 202 of SEQ ID NO:2 or SEQ ID NO:4 or SEQ ID NO:86 is a valine or leucine, the residue corresponding to residue 94 of SEQ ID NO:2 or 4 or 86 is threonine, and the residue corresponding to residue 199 of SEQ ID NO:2 or 4 or 86 is histidine, and additionally has one or more of the following substitutions such that the polypeptide is further improved (with respect to stereoselectivity, enzymatic activity, and/or thermostability) over the wild-type kefir ketoreductase or another engineered ketoreductase (such as SEQ ID NO:48): 2→A; 4→C; 11→F; 40→H; 80→T; 86→I;

96→F, V; 105→G; 129→T; 147→M, L; 153→A, S; 195→V; 196→L; 206→F; 226→V; 248→K; and 249→W.

In some embodiments, the 2S,3R ketoreductase polypeptides described herein can comprise an amino acid sequence that is at least about 85%, 86%, 87%, 88%, 89%, 90%, 91%, 92%, 93%, 94%, 95%, 96%, 97%, 98%, or 99% identical to SEQ ID NO:2, 4 or 86 (or a region or domain thereof, such as residues 90-211) with the proviso that the residues corresponding to residue 202 of SEQ ID NO:2, 4 or 86 is a valine or leucine, the residue corresponding to residue 94 of SEQ ID NO:2, 4 or 86 is threonine, and the residue corresponding to residue 199 of SEQ ID NO:2, 4 or 86 is histidine, and additionally has one or more of the following substitutions such that the polypeptide is further improved (with respect to stereoselectivity, enzymatic activity, and/or thermostability) over the wild-type *kefir* ketoreductase or another engineered ketoreductase (such as SEQ ID NO:48): 40→H; and 147→L, M.

As will be appreciated by those of skill in the art, some of the above-defined categories of amino acid residues, unless otherwise specified, are not mutually exclusive. Thus, amino acids having side chains exhibiting two or more physicochemical properties can be included in multiple categories. The appropriate classification of any amino acid or residue will be apparent to those of skill in the art, especially in light of the detailed disclosure provided herein.

In some embodiments, the improved engineered ketoreductase enzymes comprise deletions of the naturally occurring ketoreductase polypeptides or deletions of other engineered ketoreductase polypeptides. In some embodiments, each of the improved engineered ketoreductase enzymes described herein can comprise deletions of the polypeptides described herein. Thus, for each and every embodiment of the ketoreductase polypeptides of the disclosure, the deletions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the ketoreductase polypeptides, as long as the functional activity of the ketoreductase activity is maintained. In some embodiments, the deletions can comprise, 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-25, 1-30, 1-35 or about 1-40 amino acid residues. In some embodiments, the number of deletions can be 1, 2, 3, 4, 5, 6, 7, 8, 9, 10, 11, 12, 14, 15, 16, 18, 20, 22, 24, 26, 30, 35 or about 40 amino acids. In some embodiments, the deletions can comprise deletions of 1, 2, 3, 4, 5, 6, 7, 8, 9, 10, 11, 12, 13, 14, 15, 16, 18, or 20 amino acid residues.

As described herein, the ketoreductase polypeptides of the disclosure can be in the form of fusion polypeptides in which the ketoreductase polypeptides are fused to other polypeptides, such as, by way of example and not limitation, antibody tags (e.g., myc epitope), purifications sequences (e.g., His tags), and cell localization signals (e.g., secretion signals). Thus, the ketoreductase polypeptides can be used with or without fusions to other polypeptides.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisolencine (hIle); homoarginine (hArg); N-acetyl lysine (AcLys); 2,4-diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, *CRC Practical Handbook of Biochemistry and Molecular Biology*, CRC Press, Boca Raton, FL, at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

As described above the various modifications introduced into the naturally occurring polypeptide to generate an engineered ketoreductase enzyme can be targeted to a specific property of the enzyme.

1.3 Polynucleotides Encoding Engineered Ketoreductases

In another aspect, the present disclosure provides polynucleotides encoding the engineered ketoreductase enzymes. The polynucleotides may be operatively linked to one or more heterologous regulatory sequences that control gene expression to create a recombinant polynucleotide capable of expressing the polypeptide. Expression constructs containing a heterologous polynucleotide encoding the engineered ketoreductase can be introduced into appropriate host cells to express the corresponding ketoreductase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved ketoreductase enzymes disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein, including the amino acid sequences presented in Table 1.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. By way of example, the polynucleotide of SEQ ID NO: 1 has been codon optimized for expression in *E. coli*, but otherwise encodes the naturally occurring ketoreductase of *Lactobacillus kefir*.

In certain embodiments, all codons need not be replaced to optimize the codon usage of the ketoreductases since the natural sequence will comprise preferred codons and because use of preferred codons may not be required for all amino acid residues. Consequently, codon optimized polynucleotides encoding the ketoreductase enzymes may contain preferred codons at about 40%, 50%, 60%, 70%, 80%, or greater than 90% of codon positions of the full length coding region.

In some embodiments, the polynucleotide comprises a nucleotide sequence encoding a ketoreductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to any of the reference engineered ketoreductase polypeptides described herein. Accordingly, in some embodiments, the polynucleotide encodes an amino acid sequence that is at least about 80%, 85%, 86%, 87%, 88%, 89%, 90%, 91%, 92%, 93%, 94%, 95%, 96%, 97%, 98%, 99% or more identical to a reference sequence based on SEQ ID NO: 2, 4 or 86 having the following features: residue corresponding to position X94 is an aliphatic or polar residue, particularly alanine or threonine; residue corresponding to X199 is an aliphatic, constrained or polar residue, particularly alanine, histidine, or asparagine; and residue corresponding to X202 is valine or leucine, with the proviso that the encoded ketoreductase polypeptide has an amino sequence having the preceding features, i.e., residue corresponding to position X94 is an aliphatic or polar residue; residue corresponding to X199 is an aliphatic, constrained or polar residue; and residue corresponding to X202 is valine or leucine. In some embodiments, the polynucleotide encodes a ketoreductase that has an amino acid sequence in which the residue corresponding to X94 is threonine; residue corresponding to X199 is alanine, histidine, or asparagine; and residue corresponding to X202 is valine or leucine. In some embodiments, the polynucleotide encodes an amino acid sequence corresponding to SEQ ID NO: 6, 8, 10, 12, 16, 18, 20, 22, 24, 26, 28, 30, 32, 34, 36, 38, 40, 42, 44, 46, 48, 50, 52, 54, 56, or 58.

In some embodiments, the polynucleotide comprises a nucleotide sequence encoding a ketoreductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid corresponding to SEQ ID NO:14, 60, or 62.

In some embodiments, the polynucleotide comprises a nucleotide sequence encoding a ketoreductase polypeptide with an amino acid sequence that has at least about 80%, 85%, 86%, 87%, 88%, 89%, 90%, 91%, 92%, 93%, 94%, 95%, 96%, 97%, 98%, or 99% or more sequence identity to the polypeptide comprising an amino acid sequence corresponding to SEQ ID NO: 64, 66, 68, 70, 72, 74, 76, 78, 80 or 82.

In some embodiments, the polynucleotides encoding the ketoreductases are selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81. In some embodiments, the polynucleotides are capable of hybridizing under highly stringent conditions to a polynucleotide comprising SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81, where the highly stringently hybridizing polynucleotides encode a ketoreductase capable of stereoselectively reducing or converting the substrate of formula (I) to the product of formula (II), or stereoselectively reducing or converting the substrate of formula (I) to the product of formula (III).

In some embodiments, the polynucleotides encode the polypeptides described herein but have about 80% or more sequence identity, about 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered ketoreductase. In some embodiments, the reference polynucleotide is selected from SEQ ID NO: 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, or 81.

An isolated polynucleotide encoding an improved ketoreductase polypeptide may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, *Molecular Cloning: A Laboratory Manual*, 3$^{rd}$ Ed., Cold Spring Harbor Laboratory Press; and *Current Protocols in Molecular Biology*, Ausubel. F. ed., Greene Pub. Associates, 1998, updates to 2006.

For bacterial host cells, suitable promoters for directing transcription of the nucleic acid constructs of the present disclosure, include the promoters obtained from the *E. coli* lac operon, *E. coli* trp operon, bacteriophage D, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proc. Natl Acad. Sci. USA* 75: 3727-3731), as well as the tac promoter (DeBoer et al., 1983, *Proc. Natl Acad. Sci. USA* 80: 21-25). Further promoters are described in "Useful proteins from recombinant bacteria" in Scientific American, 1980, 242:74-94; and in Sambrook et al., supra.

For filamentous fungal host cells, suitable promoters for directing the transcription of the nucleic acid constructs of the present disclosure include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

For example, exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used. Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, *Mol Cell Bio* 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region.

Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiol Rev* 57: 109-137.

Effective signal peptide coding regions for filamentous fungal host cells can be the signal peptide coding regions obtained from the genes for *Aspergillus oryzae* TAKA amylase, *Aspergillus niger* neutral amylase, *Aspergillus*

*niger* glucoamylase, *Rhizomucor miehei* aspartic proteinase, *Humicola insolens* cellulase, and *Humicola lanuginosa* lipase.

Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

Other examples of regulatory sequences are those which allow for gene amplification. In eukaryotic systems, these include the dihydrofolate reductase gene, which is amplified in the presence of methotrexate, and the metallothionein genes, which are amplified with heavy metals. In these cases, the nucleic acid sequence encoding the KRED polypeptide of the present invention would be operably linked with the regulatory sequence.

Thus, in another embodiment, the present disclosure is also directed to a recombinant expression vector comprising a polynucleotide encoding an engineered ketoreductase polypeptide or a variant thereof, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector of the present invention preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

The expression vectors of the present invention preferably contain an element(s) that permits integration of the vector into the host cell's genome or autonomous replication of the vector in the cell independent of the genome. For integration into the host cell genome, the vector may rely on the nucleic acid sequence encoding the polypeptide or any other element of the vector for integration of the vector into the genome by homologous or nonhomologous recombination.

Alternatively, the expression vector may contain additional nucleic acid sequences for directing integration by homologous recombination into the genome of the host cell. The additional nucleic acid sequences enable the vector to be integrated into the host cell genome at a precise location (s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are P15A on (as shown in the plasmid of FIG. 5) or the origins of replication of plasmids pBR322, pUC19, pACYC177 (which plasmid has the P15A ori), or pACYC184 permitting replication in *E. coli*, and pUB110, pE194, pTA1060, or pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proc Natl Acad Sci. USA* 75:1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

Many of the expression vectors for use in the present invention are commercially available. Suitable commercial expression vectors include p3×FLAG™™ expression vectors from Sigma-Aldrich Chemicals, St. Louis MO., which includes a CMV promoter and hGH polyadenylation site for expression in mammalian host cells and a pBR322 origin of replication and ampicillin resistance markers for amplification in *E. coli*. Other suitable expression vectors are pBluescriptII SK(-) and pBK-CMV, which are commercially available from Stratagene, LaJolla CA, and plasmids which are derived from pBR322 (Gibco BRL), pUC (Gibco BRL), pREP4, pCEP4 (Invitrogen) or pPoly (Lathe et al., 1987, *Gene* 57:193-201).

1.4 Host Cells for Expression of Ketoreductase Polypeptides

In another aspect, the present disclosure provides a host cell comprising a polynucleotide encoding an improved ketoreductase polypeptide of the present disclosure, the polynucleotide being operatively linked to one or more control sequences for expression of the ketoreductase enzyme in the host cell. Host cells for use in expressing the KRED polypeptides encoded by the expression vectors of the present invention are well known in the art and include but are not limited to, bacterial cells, such as *E. coli*, *Lactobacillus kefir*, *Lactobacillus brevis*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Appropriate culture mediums and growth conditions for the above-described host cells are well known in the art.

Polynucleotides for expression of the ketoreductase may be introduced into cells by various methods known in the art. Techniques include among others, electroporation, biolistic particle bombardment, liposome mediated transfection, calcium chloride transfection, and protoplast fusion. Various methods for introducing polynucleotides into cells will be apparent to the skilled artisan.

An exemplary host cell is *Escherichia coli* W3110. The expression vector was created by operatively linking a polynucleotide encoding an improved ketoreductase into the plasmid pCK110900 operatively linked to the lac promoter under control of the lacI repressor. The expression vector also contained the P15a origin of replication and the chloramphenicol resistance gene. Cells containing the subject polynucleotide in *Escherichia coli* W3110 were isolated by subjecting the cells to chloramphenicol selection.

1.5 Methods of Generating Engineered Ketoreductase Polypeptides

In some embodiments, to make the improved KRED polynucleotides and polypeptides of the present disclosure, the naturally-occurring ketoreductase enzyme that catalyzes the reduction reaction is obtained (or derived) from *Lactobacillus kefir*, *Lactobacillus brevis*, or *Lactobacillus minor*. In some embodiments, the parent polynucleotide sequence is codon optimized to enhance expression of the ketoreductase in a specified host cell. As an illustration, the parental polynucleotide sequence encoding the wild-type KRED polypeptide of *Lactobacillus kefir* was constructed from oligonucleotides prepared based upon the known polypeptide sequence of *Lactobacillus kefir* KRED sequence available in Genbank database (Genbank accession no. AAP94029 GI:33112056). The parental polynucleotide sequence, designated as SEQ ID NO: 1, was codon optimized for expression in *E. coli* and the codon-optimized polynucleotide cloned into an expression vector, placing the expression of the ketoreductase gene under the control of the lac promoter and lacI repressor gene. Clones expressing the active ketoreductase in *E. coli* were identified and the genes sequenced to confirm their identity. The sequence designated (SEQ ID NO: 1) was the parent sequence utilized as the starting point for most experiments and library construction of engineered ketoreductases evolved from the *Lactobacillus kefir* ketoreductase.

The engineered ketoreductases can be obtained by subjecting the polynucleotide encoding the naturally occurring ketoreductase to mutagenesis and/or directed evolution methods, as discussed above. An exemplary directed evolution technique is mutagenesis and/or DNA shuffling as described in Stemmer, 1994, *Proc Natl Acad Sci USA* 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, *Nat. Biotechnol.* 16:258-261), mutagenic PCR (Caldwell et al., 1994, *PCR Methods Appl.* 3:S136-S140), and cassette mutagenesis (Black et al., 1996, *Proc Natl Acad Sci USA* 93:3525-3529).

The clones obtained following mutagenesis treatment are screened for engineered ketoreductases having a desired improved enzyme property. Measuring enzyme activity from the expression libraries can be performed using the standard biochemistry technique of monitoring the rate of decrease (via a decrease in absorbance or fluorescence) of NADH or NADPH concentration, as it is converted into $NAD^+$ or $NADP^+$. (For example, see Example 7.) In this reaction, the NADH or NADPH is consumed (oxidized) by the ketoreductase as the ketoreductase reduces a ketone substrate to the corresponding hydroxyl group. The rate of decrease of NADH or NADPH concentration, as measured by the decrease in absorbance or fluorescence, per unit time indicates the relative (enzymatic) activity of the KRED polypeptide in a fixed amount of the lysate (or a lyophilized powder made therefrom). Where the improved enzyme property desired is thermal stability, enzyme activity may be measured after subjecting the enzyme preparations to a defined temperature and measuring the amount of enzyme activity remaining after heat treatments. Clones containing a polynucleotide encoding a ketoreductase are then isolated, sequenced to identify the nucleotide sequence changes (if any), and used to express the enzyme in a host cell.

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides of the invention can be prepared by chemical synthesis using, e.g., the classical phosphoramidite method described by Beaucage et al., 1981, *Tet Lett* 22:1859-69, or the method described by Matthes et al., 1984, *EMBO J.* 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources, such as The Midland Certified Reagent Company, Midland, TX, The Great American Gene Company, Ramona, CA, ExpressGen Inc. Chicago, IL, Operon Technologies Inc., Alameda, CA, and many others.

Engineered ketoreductase enzymes expressed in a host cell can be recovered from the cells and or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available under the trade name CelLytic B™ from Sigma-Aldrich of St. Louis MO.

Chromatographic techniques for isolation of the ketoreductase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved ketoreductase enzymes. For affinity chromatography purification, any antibody which specifically binds the ketoreductase polypeptide may be used. For the production of antibodies, various host animals, including but not limited to rabbits, mice, rats, etc., may be immunized by injection with an engineered polypeptide. The polypeptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette Guerin) and *Corynebacterium parvum*.

1.6 Methods of Using the Engineered Ketoreductase Enzymes and Compounds Prepared Therewith In some embodiments, the ketoreductase enzymes described herein are capable of catalyzing the reduction reaction of the keto group in the compound of structural formula (I), methyl-2-benzamidomethyl-3-oxobutyrate ("the substrate"):

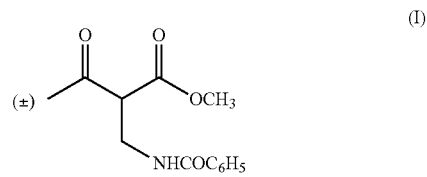

to the corresponding stereoisomeric alcohol product of structural formula (II), 2S, 3R-methyl-2-benzamidomethyl-3-hydroxybutyrate ("the product"):

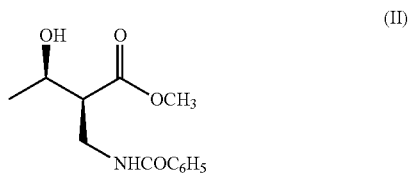

In some embodiments, the substrate of formula (I) is a racemic mixture, as shown in formula (Ia),

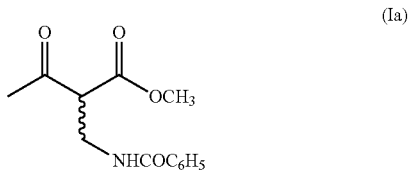

and the 2S,3R selective ketoreductases can be used to reduce or convert the racemic substrate in the reaction shown in Scheme 1 below to prepare the product of formula (II):

Scheme 1

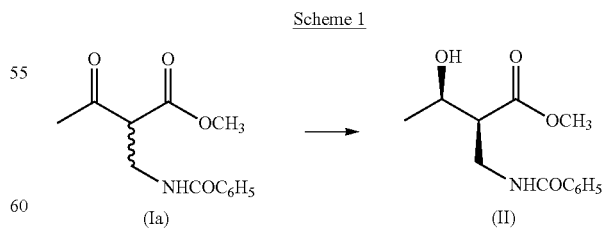

Accordingly, in some embodiments, the ketoreductases of the disclosure can be used in a method for stereoselectively reducing the substrate of structural formula (I) to the corresponding product of structural formula (II) with at least about 60% stereomeric excess, which method comprises contacting or incubating the substrate of formula (I) or formula (Ia) with a 2S,3R selective ketoreductase polypeptide of the disclosure under reaction conditions suitable for reduction or conversion of the substrate to the product of formula (II). In some embodiments of this method, the product of formula (II) is produced with at least about 85% stereomeric excess. In some embodiments of this method, the 2S,3R selective ketoreductase polypeptides have, with respect to the wild-type *L. kefir, L. brevis*, or *L. minor* KRED sequences of SEQ ID NO:4, 2, and 86, at least the following features: residue 202 is valine or leucine. In some embodiments, the 2S,3R selective ketoreductase polypeptides have, with respect to the wild-type *L. kefir, L. brevis*, or *L. minor* KRED sequences of SEQ ID NO:4, 2, and 86, at least the following features: (1) residue corresponding to X94 is an aliphatic or polar residue; (2) residue corresponding to X199 is an aliphatic, constrained, or polar residue; and (3) residue corresponding to X202 is valine or leucine. In some embodiments, the 2S,3R selective ketoreductase polypeptides have, with respect to the wild-type *L. kefir, L. brevis*, or *L. minor* KRED sequences of SEQ ID NO:4, 2, and 86, at least the following features: (1) residue corresponding to 94 is a polar residue, (2) residue corresponding to 199 is a constrained residue, and (3) residue corresponding to X202 is valine or leucine.

In some embodiments of the method for converting the substrate to the product of structural formula (II), the substrate is converted to the product with a percent stereomeric excess of at least about 60-89% and at a rate that is at least about 1-15 fold greater than the rate capable by the polypeptide having the amino acid sequence of SEQ ID NO:48. Exemplary polypeptides that may be used in this method include, but are not limited to, polypeptides comprising amino acid sequences corresponding to SEQ ID NO: 6, 8, 10, 12, 14, 16, 18, 20, 22, 24, 26, 28, 30, 32, 34, 36, 38, 40, 42, 46, 50, 52, 54, 56, 58, 60, and 62.

In some embodiments of the method for converting the substrate to the product of structural formula (II), the substrate is converted to the product with a percent stereomeric excess of at least about 90-94%. Exemplary polypeptides that may be used in this method include, but are not limited to, polypeptides comprising amino acid sequences corresponding to SEQ ID NO: 6, 8, 10, 12, 14, 16, 18, 20, 22, 24, 26, 28, 30, 32, 34, 36, 40, 42, 50, 52, 56, 58, 60, and 62.

In some embodiments of the method for converting the substrate to the product of structural formula (II), the substrate is converted to the product with a percent stereomeric excess of at least about 95-99%. Exemplary polypeptides that may be used in this method include, but are not limited to, polypeptides comprising amino acid sequences corresponding to SEQ ID NO: 6, 8, 10, 12, 14, 16, 18, 20, 22, 24, 26, 28, 30, 32, 34, 42, 50, 52, 56, 58, 60, and 62.

In some embodiments, the ketoreductase enzymes described herein are capable of catalyzing the reduction reaction of the keto group in the compound of structural formula (I) to the corresponding stereoisomeric alcohol product of structural formula (III), 2R,3R-methyl-2-benzamidomethyl-3-hydroxybutyrate, (which can also be referred to as a "product"):

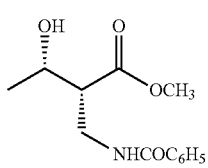
(III)

In some embodiments, the substrate of formula (I) is a racemic mixture as shown in formula (Ia), and the 2R,3R selective ketoreductases can be used to reduce or convert the racemic substrate in the reaction shown in Scheme 3 below to prepare the product of formula (III):

Scheme 2

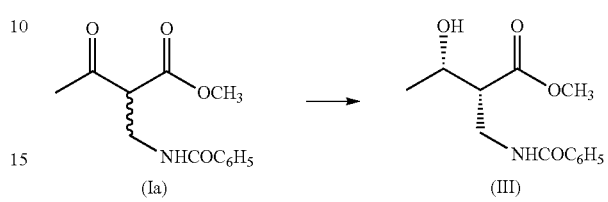

In some embodiments of the method for converting the substrate to the product of structural formula (III), the substrate is converted to the product with a percent stereomeric excess of at least about 85%. Exemplary polypeptides that may be used in this method include, but are not limited to, polypeptides comprising amino acid sequences corresponding to SEQ ID NO: 68, 72, 74, 76, 78, and 82.

In some embodiments of the method for converting the substrate to the product of structural formula (III), the substrate is converted to the product at a rate that is at least about 1 fold greater than the rate capable by the polypeptide having the amino acid sequence of SEQ ID NO:66. Exemplary polypeptides that may be used in this method include, but are not limited to, polypeptides comprising amino acid sequences corresponding to SEQ ID NO: 64, 68, 70, 72, 74, 76, 78. 80, and 82.

In some embodiments, the ketoreductases described herein can be used in a method for synthesizing a carbapenem, the method comprising the general process shown below (Scheme 3),

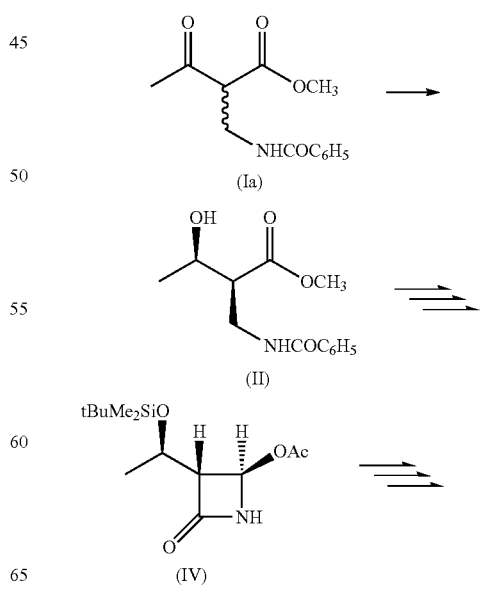

-continued

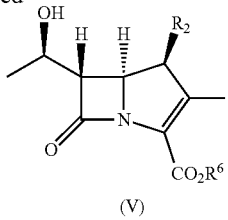

(V)

where the KRED can be any one of the ketoreductase polypeptides disclosed herein. The carbapenem of the general formula (V) are described in further detail below. For the synthesis of various carbapenem based therapeutics, an important intermediate is the compound of structural formula (IVa),

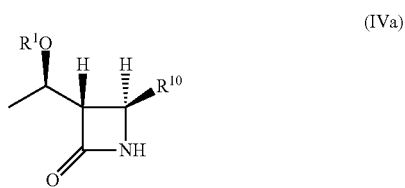

(IVa)

where $R^1$ is H or a hydroxyl protecting group, and $R^{10}$ is a halogen (e.g., Cl), or —OAc (Ac is acetate). Various hydroxyl protecting groups are known in the art, and include, by way of example and not limitation, silyl ethers (e.g., t-butyl dimethyl silyl) and substituted benzyl ethers (see, Green and Wuts, *Protective Groups in Organic Synthesis*, Wiley-Interscience, New York, 1999). Accordingly, in a method for the synthesis of the intermediate of structural formula (IVa), a step in the method comprises contacting or reacting the substrate of formula (I) with the ketoreductases of the disclosure under reaction conditions suitable for reducing or converting the substrate to the product of formula (II). The synthesis of the intermediate of formula (IVa) in which $R^{10}$ is —OAc is described in *Tetrahedron Lett.* 23:2293 (1982); *Tetrahedron Lett.* 39:2399 (1983); *Tetrahedron Lett.* 39:2505 (1983); EP0290385; and EP0369691; all references incorporated herein by reference. In some embodiments, the intermediate of formula (IVa) in which $R^{10}$ is —OAc can be synthesized as illustrated in Scheme 4:

In Scheme 4, the method comprises: (a) reducing the substrate of formula (I) to the product of formula (II) by contacting or reacting the substrate with a 2S,3R selective ketoreductase of the present disclosure under reaction conditions suitable for reducing the substrate to the product of formula (II); (b) removing the group —C(O)C$_6$H$_5$ to form compound (VI); (c) converting the compound of formula (VI) to the □-lactam of formula (VII) by reacting with triphenylphosphine and N-tert-butyl-2-benzothiazolylsulfenamide (see, e.g., *Tetrahedron Lett.* 1995, 36(21): 3703); (d) reacting with tert-butyl dimethyl chlorosilane (TBDMS-Cl) to form the compound of formula (VIII); and (e) acetoxylating the compound of formula (VIII) in presence of peracetic acid and ruthenium to form the intermediate of formula (IV) (see, e.g., Murahashi et al., 1990, *J. Am. Chem. Soc.* 112(21):7820-7822).

In some embodiments, another intermediate in the synthesis of carbapenem based therapeutics is the intermediate of structural formula (IX):

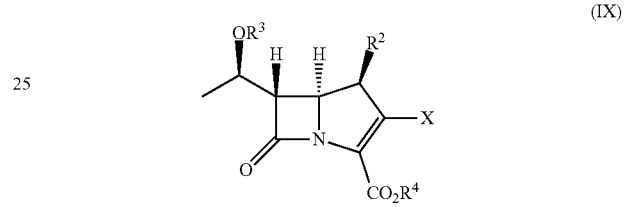

(IX)

where $R^2$ is H or a C1-C4 alkyl (e.g., —CH$_3$); $R^3$ is H, or a hydroxyl protecting group; $R^4$ is H, carboxy protecting group, ammonia group, alkali metal, or alkaline earth metal; and X is OH, or a leaving group. Exemplary leaving groups include, but are not limited to, —OP(O)(OR') or OS(O2)R", where R' and R" can be C1-C6 alkyl, C1-C6 alkaryl, aryl, perfluoro C1-C6 alkyl. Protecting groups for $R^4$ can be, but not limited to, benzyl, p-nitrobenzyl, and methoxymethyl. Descriptions of the intermediate of structural formula (IX) and its synthesis is provided in various references, e.g., U.S. Pat. Nos. 5,317,016; 4,933,333; and WO 0236594; the disclosures of which are incorporated herein by reference. Accordingly, in some embodiments, in a method for the synthesis of the intermediate of formula (IX), a step in the Scheme 4

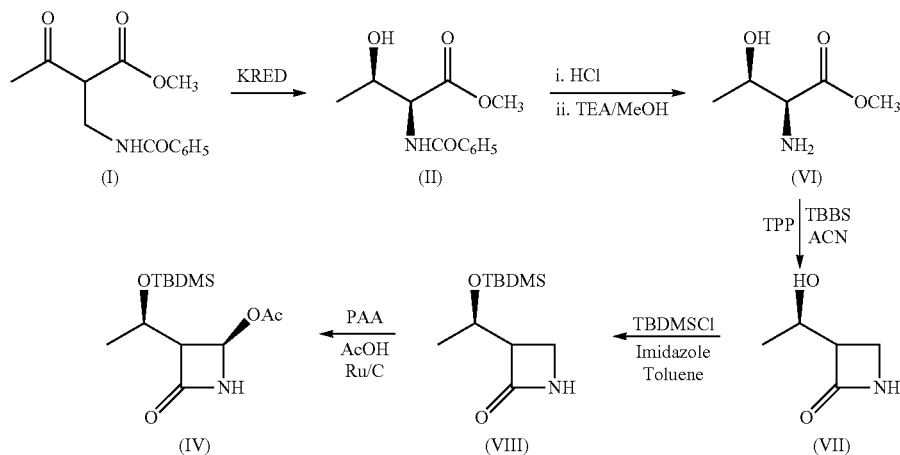

method comprises contacting or reacting the substrate of formula (I) with the ketoreductases of the disclosure under reaction conditions suitable for reducing or converting the substrate to the product of formula (II).

In some embodiments, the ketoreductases of the disclosure can be used in a process for synthesis of carbapenem based therapeutic compounds of structural formula (V):

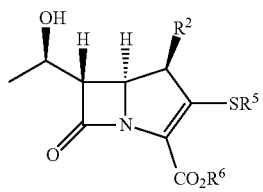

(V)

or solvates, hydrates, salts, and prodrugs thereof, where $R^2$ is H or —$CH_3$; $R^5$ can be various substituents, including, but not limited to, substituted or unsubstituted alkyl, substituted or unsubstituted aryl, substituted or unsubstituted heteroalkyl, substituted or unsubstituted heterocycloalkyl, and substituted or unsubstituted heteroarylalkyl; and $R^6$ is H, or a progroup, such as a hydrolyzable ester group. As used herein, progroup refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art. Accordingly, in the method for the synthesis of the compound of structural formula (V), a step in the method can comprise contacting or reacting the substrate of formula (I) with the ketoreductases of the disclosure under reaction conditions suitable for reducing or converting the substrate to the product of formula (II). Synthesis of various carbapenem based therapeutic compounds are described in, among others, U.S. Pat. Nos. 4,925,836; 5,317,016; WO 02/036594; WO2004/067532; and WO 2007/104221; the disclosures of which are incorporated herein by reference.

In some embodiments, the ketoreductases of the disclosure can be used for the synthesis of Imipenem of the following structure (X):

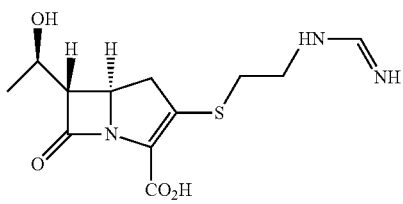

(X)

or solvates, hydrates, prodrugs, and salts thereof. Imipenem has a broad spectrum of activity against aerobic and anaerobic Gram positive and Gram negative bacteria. It is particularly effective against *Pseudomonas aeruginosa* and the *Enterococcus* species. Accordingly, in a method for the synthesis of Imipenem of structural formula (X), a step in the method comprises contacting or reacting the substrate of formula (I) with the ketoreductases of the disclosure under reaction conditions suitable for reducing or converting the substrate to the product of formula (II). Process of preparing Imipenem from the intermediate of structural formula (VI) is described in WO 0236594, incorporated herein by reference.

In some embodiments, the ketoreductases of the disclosure can be used in the synthesis of Doripenem of structural formula (XI):

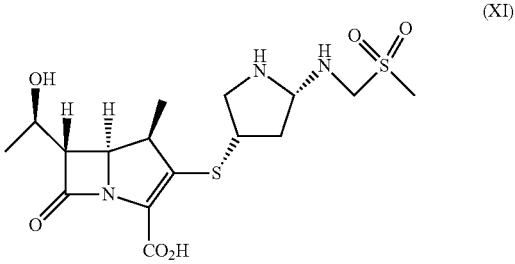

(XI)

or solvates, hydrates or salts thereof. Doripenem has a spectrum and potency against Gram-positive cocci similar to Imipenem or Ertapenem, and a Gram-negative activity similar to Meropenem. Accordingly, in a method for the synthesis of Doripenem of structural formula (XI), a step in the method comprises contacting or reacting the substrate of formula (I) with a ketoreductase of the present disclosure under reaction conditions suitable for reducing or converting the substrate to the product of formula (II). The process of preparing Doripenem from the intermediate of formula (VI) is described in U.S. Pat. No. 5,317,016, incorporated herein by reference.

In some embodiments, the ketoreductases of the disclosure can be used in the synthesis of Meropenem of structural formula (XII):

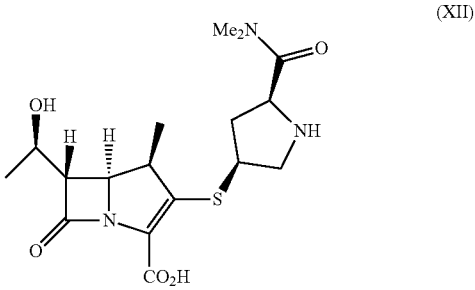 [SMILES: C[C@@H](O)[C@H]1C(=O)N2C(C(=O)O)=C(S[C@@H]3CN[C@H](C(=O)N(C)C)C3)[C@H](C)[C@H]12]

(XII)

or solvates, hydrates, prodrugs, and salts thereof. Meropenem is indicated for treatment of intra-abdominal infections, e.g., appendicitis and peritonitis; treatment of bacterial meningitis; and treatment of skin and skin structure infections caused by susceptible organisms. Accordingly, in a method for the synthesis of Meropenem of formula (XII), a step in the method comprises contacting or reacting the substrate of formula (I) with a ketoreductase of the present disclosure under reaction conditions suitable for reducing or converting the substrate to the product of formula (II). A process for preparing Meropenem is described in WO 2007/104221, incorporated herein by reference.

In some embodiments, the ketoreductases of the disclosure can be used in the synthesis of Ertapenem of structural formula (XIII):

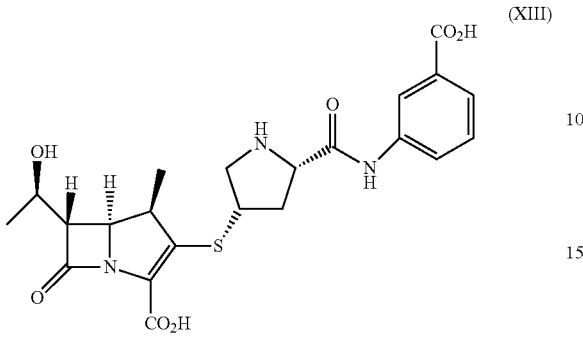

(XIII)

or solvates, hydrates, prodrugs, and salts thereof. Ertapenem is effective against Gram negative bacteria, but not active against MRSA, ampicillin-resistant enterococci, *Pseudomonas aeruginosa* or *Acinetobacter* species. Ertapenem also has clinically useful activity against anaerobic bacteria. Ertapenem is primarily used against extended spectrum beta-lactamase (ESBL)-producing and high level AmpC-producing Gram-negative bacteria. Accordingly, in a method for the synthesis of Ertapenem of formula (XIII), a step in the method comprises contacting or reacting the substrate of formula (I) with the ketoreductases of the disclosure under reaction conditions suitable for reducing or converting the substrate to the product of formula (II). Processes for preparing Ertapenem is described in U.S. Pat. Nos. 5,478,820 and 7,342,005, incorporated herein by reference.

In some embodiments, the ketoreductases of the disclosure can be used in the synthesis of Biapenem of structural formula (XIV):

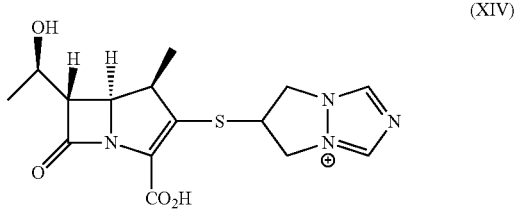 [SMILES: C[C@@H](O)[C@H]1C(=O)N2C(C(=O)O)=C(SC3Cn4cnc[n+]4C3)[C@H](C)[C@H]12]

(XIV)

or solvates, hydrates, prodrugs, or salts thereof. Biapenem is a parenteral carbapenem that possesses antibacterial activities against a wide range of Gram-positive and -negative bacteria, and is stable to human renal dehydropeptidase-I (DHP-I). It also shows in vitro activity against anaerobic bacteria. Accordingly, in a method for the synthesis of Biapenem of formula (XIV), a step in the method comprises contacting or reacting the substrate of formula (I) with the ketoreductases of the disclosure under reaction conditions suitable for reducing or converting the substrate to the product of formula (II). Process of preparing Biapenem from intermediate (IVa) is described in U.S. Pat. No. 4,925,836, incorporated herein by reference.

In some embodiments, the ketoreductases of the disclosure can be used in the synthesis of Panipenem of structural formula (XII):

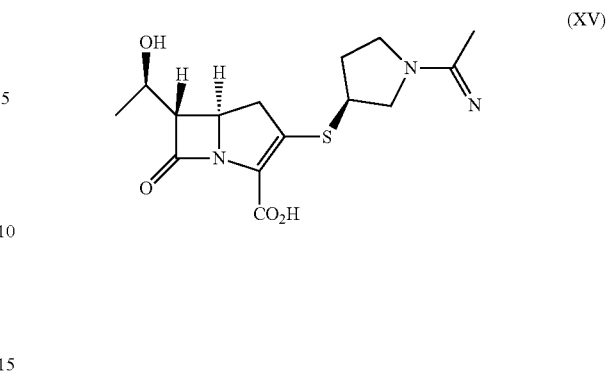

(XV)

or solvates, hydrates, and salts thereof. Accordingly, in a method for the synthesis of Panipenem of formula (XV), a step in the method comprises contacting or reacting the substrate of formula (I) with the ketoreductases of the disclosure under reaction conditions suitable for reducing or converting the substrate to the product of formula (II). Panipenem from the intermediate of formula (II) is described in Miyadera et al., 1983, *J Antibiotic* (Tokyo) 36(8):1034-1039; and Hirai et al., 1999, *J. Synth Org. Chem.* 57(5):382-386, incorporated herein by reference.

In some embodiments, the ketoreductases of the disclosure can be used in a method for the synthesis of sulopenem compounds of formula (XVI):

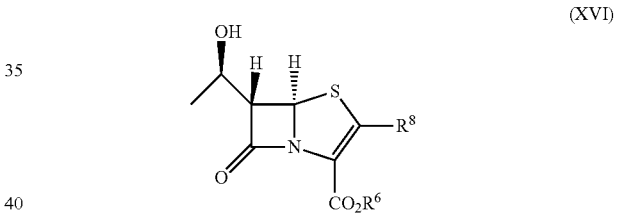

(XVI)

where $R^6$ is H or a progroup, and $R^8$ can be substituted or unsubstituted alkyl, substituted or unsubstituted aryl; substituted or unsubstituted heteroalkyl, substituted or unsubstituted heterocycloalkyl, and substituted or unsubstituted heteroarylalkyl, or —$SR^9$, where $R^9$ can be substituents as described for $R^8$. Other substituents for $R^8$ that are in bioactive sulopenem therapeutic compounds are known in the art, some of which are further described below. Descriptions of sulopenems can be found in, among others, U.S. Pat. Nos. 3,951,954; 4,234,579, 4,287,181; 4,452,796; 4,343,693; 4,348,264; 4,416,891; 4,457,924; and 5,013,729; 5,506,225; Volkmann et al., 1992, *J. Org. Chem.* 57:4352-4361; and Volkmann and O'Neill, 1991, *Strategies and Tactics in Organic Synthesis*, Vol 13, pg 485-534; the disclosures of which are incorporated herein by reference. Accordingly, in a method for the synthesis of a sulopenem of structural formula (XVI), a step in the method comprises contacting or reacting the substrate of formula (I) with the ketoreductases of the disclosure under reaction conditions suitable for reducing or converting the substrate to the product of formula (II).

In some embodiments, the ketoreductases of the disclosure can be used in a method for the synthesis of a sulopenem of formula (XVII):

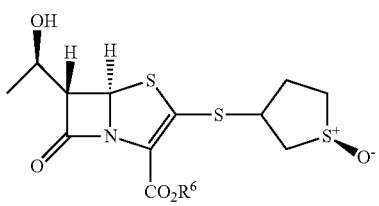

(XVII)

or solvates, hydrates, prodrugs, and salts thereof, where $R^6$ is H or a progroup. Accordingly, in a method for the synthesis of the compound of formula (XVII), a step in the method comprises contacting or reacting the substrate of formula (I) with the ketoreductases of the disclosure under reaction conditions suitable for reducing or converting the substrate to the product of formula (II). A process for the synthesis of the sulopenem of formula (XVII) is described in U.S. Pat. No. 5,013,729. Various progroups for $R^6$ are described in US application publication 2008/0009474, US application publication 2008/0125408; and Wujcik et al., 2008, Rapid Commun. Mass Spectrom. 22:3195-3206; the disclosures of which are incorporated herein by reference.

In some embodiments, the ketoreductases of the disclosure can be used in a method for the synthesis of a sulopenem of structural formula (XVIII):

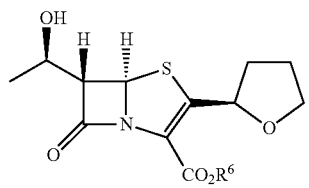

(XVIII)

or solvates, hydrates, prodrugs, and salts thereof, where $R^6$ is H or a progroup. Accordingly, in a method for the synthesis of Panipenem of formula (XVIII), a step in the method comprises contacting or reacting the substrate of formula (I) with the ketoreductases of the disclosure under reaction conditions suitable for reducing or converting the substrate to the product of formula (II). Process for synthesis of the sulopenem of formula (XVIII) is described in U.S. Pat. No. 5,506,225, and WO 2007/039885.

Another sulopenem compound that can be synthesized using the ketoreductases disclosed herein is the sulopenem of formula (XIX):

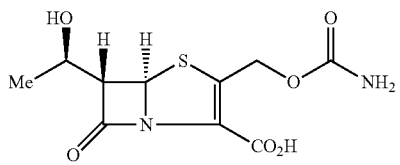

(XIX)

Accordingly, in a method for the synthesis of the compound of formula (XIX), or solvates, hydrates, prodrugs, and salts thereof, a step in the method comprises contacting or reacting the substrate of formula (I) with the ketoreductases of the disclosure under reaction conditions suitable for reducing or converting the substrate to the product of formula (II). Ritipenem of structural formula (XIX) is described in U.S. Pat. No. 4,482,565.

In some embodiments, the ketoreductases of the disclosure can be used in a method for the synthesis of a sulopenem of structural formula (XX):

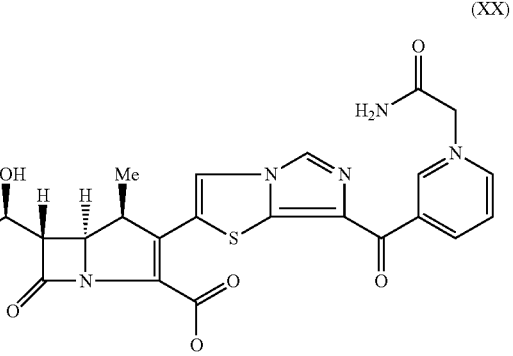

(XX)

or solvates, hydrates, prodrugs, and salts thereof. Accordingly, in a method for the synthesis of the compound of formula (XX), a step in the method comprises contacting or reacting the substrate of formula (I) with the ketoreductases of the disclosure under reaction conditions suitable for reducing or converting the substrate to the product of formula (II). The compound of structural formula (XX) is described in EP1336612; incorporated herein by reference.

In some embodiments, the ketoreductases of the disclosure can be used in a method for synthesis of the compound of structural formula (XXI):

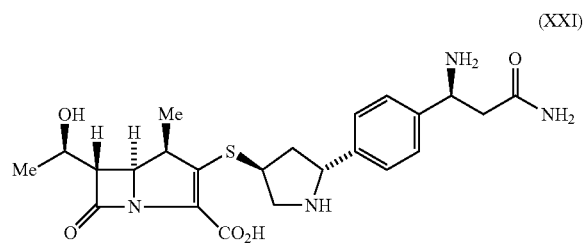

(XXI)

or solvates, hydrates, prodrugs, and salts thereof. Accordingly, in a method for the synthesis of the compound of formula (XXI), a step in the method comprises contacting or reacting the substrate of formula (I) with the ketoreductases of the disclosure under reaction conditions suitable for reducing or converting the substrate to the product of formula (II). The compound of structural formula (XXI) is described in JP2002114788; incorporated herein by reference.

In some embodiments, the ketoreductases of the disclosure can be used in a method for the synthesis of a sulopenem of structural formula (XXII):

(XXII)

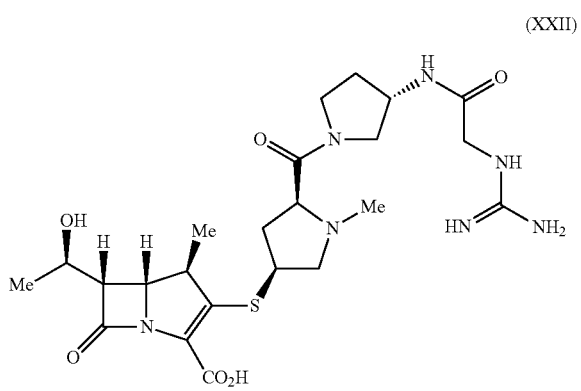 [SMILES: C[C@@H](O)[C@H]1C(=O)N2C(C(=O)O)=C(S[C@H]3C[C@@H](C(=O)N4CC[C@H](NC(=O)CNC(=N)N)C4)N(C)C3)[C@H](C)[C@@H]12]

or solvates, hydrates, prodrugs, and salts thereof. Accordingly, in a method for the synthesis of the compound of formula (XXII), a step in the method comprises contacting or reacting the substrate of formula (I) with the ketoreductases of the disclosure under reaction conditions suitable for reducing or converting the substrate to the product of formula (II). The compound of structural formula (XXII) is described in U.S. Pat. Nos. 6,924,279 and 7,034,150, the disclosures of which are incorporated herein by reference.

In some embodiments, the ketoreductases of the disclosure can be used in a method for the synthesis of a sulopenem of structural formula (XXIII):

(XXIII)

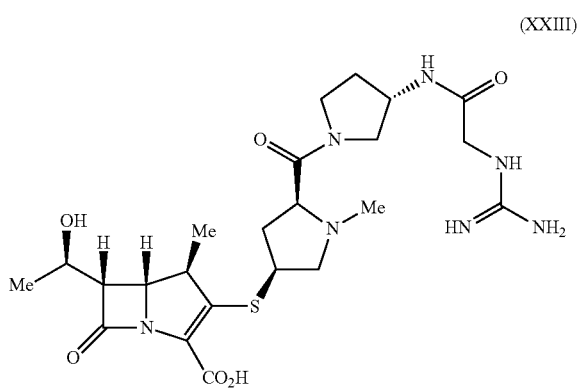 [SMILES: C[C@@H](O)[C@H]1C(=O)N2C(C(=O)O)=C(S[C@H]3C[C@@H](C(=O)N4CC[C@H](NC(=O)CNC(=N)N)C4)N(C)C3)[C@H](C)[C@@H]12]

or solvates, hydrates, prodrugs, and salts thereof. Accordingly, in a method for the synthesis of the compound of formula (XXIII), a step in the method comprises contacting or reacting the substrate of formula (I) with the ketoreductases of the disclosure under reaction conditions suitable for reducing or converting the substrate to the product of formula (II). The compound of structural formula (XXIII) is described in WO 2008/047909 and U.S. Pat. No. 5,659,043, the disclosures of which are incorporated herein by reference.

In some embodiments, the ketoreductases of the disclosure can be present as compositions, for example reaction compositions, with the substrates acted on by the ketoreductases, and/or with the products produced by the ketoreductase reaction. Accordingly, in some embodiments, a composition can comprise a 2S,3R selective ketoreductase of the present disclosure, and a substrate of structural formula (I). In some embodiments, a composition can comprise a 2S,3R selective ketoreductase of the present disclosure, and a product of structural formula (II). In some embodiments, the composition can comprise a 2S,3R ketoreductase of the disclosure, the substrate of formula (I) and the product of formula (II).

In some embodiments, a composition can comprise a 2R,3R selective ketoreductase of the present disclosure, and a substrate of structural formula (I). In some embodiments, a composition can comprise a 2R,3R selective ketoreductase of the present disclosure, and a product of structural formula (III). In some embodiments, the composition can comprise a 2R,3R ketoreductase of the disclosure, the substrate of formula (I) and the product of formula (III).

Because the ketoreductase reactions can be carried out in the presence of a co-factor (NADH or NADPH) regenerating system, the reaction conditions can further include elements of a co-factor regenerating system, which are described in further detail below. Accordingly, in some embodiments, the foregoing compositions of ketoreductases can further include a cofactor regenerating system comprising glucose dehydrogenase and glucose; formate dehydrogenase and formate; or isopropanol and a secondary alcohol dehydrogenase. In some embodiments, the secondary alcohol dehydrogenase is an engineered ketoreductase. Other enzymes and substrates that can be used for co-factor recycling will be well known to the skilled artisan.

As is known by those of skill in the art, ketoreductase-catalyzed reduction reactions typically require a cofactor. Reduction reactions catalyzed by the engineered ketoreductase enzymes described herein also typically require a cofactor, although many embodiments of the engineered ketoreductases require far less cofactor than reactions catalyzed with wild-type ketoreductase enzymes. As used herein, the term "cofactor" refers to a non-protein compound that operates in combination with a ketoreductase enzyme. Cofactors suitable for use with the engineered ketoreductase enzymes described herein include, but are not limited to, $NADP^+$ (nicotinamide adenine dinucleotide phosphate), NADPH (the reduced form of $NADP^+$), $NAD^+$ (nicotinamide adenine dinucleotide) and NADH (the reduced form of $NAD^+$). Generally, the reduced form of the cofactor is added to the reaction mixture. The reduced NAD(P)H form can be optionally regenerated from the oxidized $NAD(P)^+$ form using a cofactor regeneration system.

The term "cofactor regeneration system" refers to a set of reactants that participate in a reaction that reduces the oxidized form of the cofactor (e.g., $NADP^+$ to NADPH). Cofactors oxidized by the ketoreductase-catalyzed reduction of the keto substrate are regenerated in reduced form by the cofactor regeneration system. Cofactor regeneration systems comprise a stoichiometric reductant that is a source of reducing hydrogen equivalents and is capable of reducing the oxidized form of the cofactor. The cofactor regeneration system may further comprise a catalyst, for example an enzyme catalyst that catalyzes the reduction of the oxidized form of the cofactor by the reductant. Cofactor regeneration systems to regenerate NADH or NADPH from $NAD^+$ or $NADP^+$, respectively, are known in the art and may be used in the methods described herein.

Suitable exemplary cofactor regeneration systems that may be employed include, but are not limited to, glucose and glucose dehydrogenase, formate and formate dehydrogenase, glucose-6-phosphate and glucose-6-phosphate dehydrogenase, a secondary (e.g., isopropanol) alcohol and secondary alcohol dehydrogenase, phosphite and phosphite dehydrogenase, molecular hydrogen and hydrogenase, and the like. These systems may be used in combination with either $NADP^+$/NADPH or $NAD^+$/NADH as the cofactor. Electrochemical regeneration using hydrogenase may also be used as a cofactor regeneration system. See, e.g., U.S. Pat. Nos. 5,538,867 and 6,495,023, both of which are incorporated herein by reference. Chemical cofactor regeneration systems comprising a metal catalyst and a reducing agent (for example, molecular hydrogen or formate) are also suitable. See, e.g., PCT publication WO 2000/053731, which is incorporated herein by reference.

The terms "glucose dehydrogenase" and "GDH" are used interchangeably herein to refer to an $NAD^+$ or $NADP^+$-dependent enzyme that catalyzes the conversion of D-glucose and $NAD^+$ or $NADP^+$ to gluconic acid and NADH or NADPH, respectively. Equation (1), below, describes the glucose dehydrogenase-catalyzed reduction of $NAD^+$ or $NADP^+$ by glucose.

$$\text{glucose} + NAD(P)^+ + H_2O \xrightarrow{GDH} \text{gluconic acid} + NAD(P)H + H^+ \quad (1)$$

Glucose dehydrogenases that are suitable for use in the practice of the methods described herein include both naturally occurring glucose dehydrogenases, as well as non-naturally occurring glucose dehydrogenases. Naturally occurring glucose dehydrogenase encoding genes have been reported in the literature. For example, the *Bacillus subtilis* 61297 GDH gene was expressed in *E. coli* and was reported to exhibit the same physicochemical properties as the enzyme produced in its native host (Vasantha et al., 1983, *Proc. Natl. Acad. Sci. USA* 80:785). The gene sequence of the *B. subtilis* GDH gene, which corresponds to Genbank Acc. No. M12276, was reported by Lampel et al., 1986, *J. Bacteriol.* 166:238-243, and in corrected form by Yamane et al., 1996, *Microbiology* 142:3047-3056 as Genbank Acc. No. D50453. Naturally occurring GDH genes also include those that encode the GDH from *B. cereus* ATCC 14579 (Nature, 2003, 423:87-91; Genbank Acc. No. AE017013) and *B. megaterium* (*Eur. J. Biochem.*, 1988, 174:485-490, Genbank Acc. No. X12370; *J. Ferment. Bioeng.*, 1990, 70:363-369, Genbank Acc. No. GI216270). Glucose dehydrogenases from *Bacillus* sp. are provided in PCT publication WO 2005/018579 as SEQ ID NOS: 10 and 12 (encoded by polynucleotide sequences corresponding to SEQ ID NOS: 9 and 11, respectively, of the PCT publication), the disclosure of which is incorporated herein by reference.

Non-naturally occurring glucose dehydrogenases may be generated using known methods, such as, for example, mutagenesis, directed evolution, and the like. GDH enzymes having suitable activity, whether naturally occurring or non-naturally occurring, may be readily identified using the assay described in Example 4 of PCT publication WO 2005/018579, the disclosure of which is incorporated herein by reference. Exemplary non-naturally occurring glucose dehydrogenases are provided in PCT publication WO 2005/018579 as SEQ ID NOS: 62, 64, 66, 68, 122, 124, and 126. The polynucleotide sequences that encode them are provided in PCT publication WO 2005/018579 as SEQ ID NOS: 61, 63, 65, 67, 121, 123, and 125, respectively. All of these sequences are incorporated herein by reference. Additional non-naturally occurring glucose dehydrogenases that are suitable for use in the ketoreductase-catalyzed reduction reactions disclosed herein are provided in U.S. application publication Nos. 2005/0095619 and 2005/0153417, the disclosures of which are incorporated herein by reference.

Glucose dehydrogenases employed in the ketoreductase-catalyzed reduction reactions described herein may exhibit an activity of at least about 10 μmol/min/mg and sometimes at least about $10^2$ μmol/min/mg or about $10^3$ μmol/min/mg, up to about $10^4$ μmol/min/mg or higher in the assay described in Example 4 of PCT publication WO 2005/018579.

The ketoreductase-catalyzed reduction reactions described herein are generally carried out in a solvent. Suitable solvents include water, organic solvents (e.g., ethyl acetate, butyl acetate, 1-octanol, heptane, octane, methyl t-butyl ether (MTBE), toluene, and the like), ionic liquids (e.g., 1-ethyl 4-methylimidazolium tetrafluoroborate, 1-butyl-3-methylimidazolium tetrafluoroborate, 1-butyl-3-methylimidazolium hexafluorophosphate, and the like). In some embodiments, aqueous solvents, including water and aqueous co-solvent systems, are used.

Exemplary aqueous co-solvent systems have water and one or more organic solvent. In general, an organic solvent component of an aqueous co-solvent system is selected such that it does not completely inactivate the ketoreductase enzyme. Appropriate co-solvent systems can be readily identified by measuring the enzymatic activity of the specified engineered ketoreductase enzyme with a defined substrate of interest in the candidate solvent system, utilizing an enzyme activity assay, such as those described herein.

The organic solvent component of an aqueous co-solvent system may be miscible with the aqueous component, providing a single liquid phase, or may be partly miscible or immiscible with the aqueous component, providing two liquid phases. Generally, when an aqueous co-solvent system is employed, it is selected to be biphasic, with water dispersed in an organic solvent, or vice-versa. Generally, when an aqueous co-solvent system is utilized, it is desirable to select an organic solvent that can be readily separated from the aqueous phase. In general, the ratio of water to organic solvent in the co-solvent system is typically in the range of from about 90:10 to about 10:90 (v/v) organic solvent to water, and between 80:20 and 20:80 (v/v) organic solvent to water. The co-solvent system may be pre-formed prior to addition to the reaction mixture, or it may be formed in situ in the reaction vessel.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below, or 7.5 or below. Alternatively, the reduction may be carried out a neutral pH, i.e., about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer. Suitable buffers to maintain desired pH ranges are known in the art and include, for example, phosphate buffer, triethanolamine buffer, and the like. Combinations of buffering and acid or base addition may also be used.

When the glucose/glucose dehydrogenase cofactor regeneration system is employed, the co-production of gluconic acid (pKa=3.6), as represented in equation (3) causes the pH of the reaction mixture to drop if the resulting aqueous gluconic acid is not otherwise neutralized. The pH of the reaction mixture may be maintained at the desired level by standard buffering techniques, wherein the buffer neutralizes the gluconic acid up to the buffering capacity provided, or by the addition of a base concurrent with the course of the conversion. Combinations of buffering and base addition may also be used. Suitable buffers to maintain desired pH ranges are described above. Suitable bases for neutralization of gluconic acid are organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like. The addition of a base concurrent with the course of the conversion may be done manually while monitoring the reaction mixture pH or, more conveniently, by using an automatic titrator as a pH stat. A combination of partial buffering capacity and base addition can also be used for process control.

When base addition is employed to neutralize gluconic acid released during a ketoreductase-catalyzed reduction reaction, the progress of the conversion may be monitored by the amount of base added to maintain the pH. Typically, bases added to unbuffered or partially buffered reaction mixtures over the course of the reduction are added in aqueous solutions.

In some embodiments, the co-factor regenerating system can comprises a formate dehydrogenase. The terms "formate dehydrogenase" and "FDH" are used interchangeably herein to refer to an NAD$^+$ or NADP$^+$-dependent enzyme that catalyzes the conversion of formate and NAD$^+$ or NADP$^+$ to carbon dioxide and NADH or NADPH, respectively. Formate dehydrogenases that are suitable for use as cofactor regenerating systems in the ketoreductase-catalyzed reduction reactions described herein include both naturally occurring formate dehydrogenases, as well as non-naturally occurring formate dehydrogenases. Formate dehydrogenases include those corresponding to SEQ ID NOS: 70 (*Pseudomonas* sp.) and 72 (*Candida boidinii*) of PCT publication WO 2005/018579, which are encoded by polynucleotide sequences corresponding to SEQ ID NOS: 69 and 71, respectively, of PCT publication 2005/018579, the disclosures of which are incorporated herein by reference. Formate dehydrogenases employed in the methods described herein, whether naturally occurring or non-naturally occurring, may exhibit an activity of at least about 1 µmol/min/mg, sometimes at least about 10 µmol/min/mg, or at least about 10$^2$ µmol/min/mg, up to about 10$^3$ µmol/min/mg or higher, and can be readily screened for activity in the assay described in Example 4 of PCT publication WO 2005/018579.

As used herein, the term "formate" refers to formate anion (HCO$_2^-$), formic acid (HCO$_2$H), and mixtures thereof. Formate may be provided in the form of a salt, typically an alkali or ammonium salt (for example, HCO$_2$Na, KHCO$_2$NH$_4$, and the like), in the form of formic acid, typically aqueous formic acid, or mixtures thereof. Formic acid is a moderate acid. In aqueous solutions within several pH units of its pKa (pKa=3.7 in water) formate is present as both HCO$_2$ and HCO$_2$H in equilibrium concentrations. At pH values above about pH 4, formate is predominantly present as HCO$_2$. When formate is provided as formic acid, the reaction mixture is typically buffered or made less acidic by adding a base to provide the desired pH, typically of about pH 5 or above. Suitable bases for neutralization of formic acid include, but are not limited to, organic bases, for example amines, alkoxides and the like, and inorganic bases, for example, hydroxide salts (e.g., NaOH), carbonate salts (e.g., NaHCO$_3$), bicarbonate salts (e.g., K$_2$CO$_3$), basic phosphate salts (e.g., K$_2$HPO$_4$, Na$_3$PO$_4$), and the like.

For pH values above about pH 5, at which formate is predominantly present as HCO$_2^-$, Equation (2) below, describes the formate dehydrogenase-catalyzed reduction of NAD$^+$ or NADP$^+$ by formate.

(2)

When formate and formate dehydrogenase are employed as the cofactor regeneration system, the pH of the reaction mixture may be maintained at the desired level by standard buffering techniques, wherein the buffer releases protons up to the buffering capacity provided, or by the addition of an acid concurrent with the course of the conversion. Suitable acids to add during the course of the reaction to maintain the pH include organic acids, for example carboxylic acids, sulfonic acids, phosphonic acids, and the like, mineral acids, for example hydrohalic acids (such as hydrochloric acid), sulfuric acid, phosphoric acid, and the like, acidic salts, for example dihydrogenphosphate salts (e.g., KH$_2$PO$_4$), bisulfate salts (e.g., NaHSO$_4$) and the like. Some embodiments utilize formic acid, whereby both the formate concentration and the pH of the solution are maintained.

When acid addition is employed to maintain the pH during a reduction reaction using the formate/formate dehydrogenase cofactor regeneration system, the progress of the conversion may be monitored by the amount of acid added to maintain the pH. Typically, acids added to unbuffered or partially buffered reaction mixtures over the course of conversion are added in aqueous solutions.

The terms "secondary alcohol dehydrogenase" and "sADH" are used interchangeably herein to refer to an NAD$^+$ or NADP$^+$-dependent enzyme that catalyzes the conversion of a secondary alcohol and NAD$^+$ or NADP$^+$ to a ketone and NADH or NADPH, respectively. Equation (3), below, describes the reduction of NAD$^+$ or NADP$^+$ by a secondary alcohol, illustrated by isopropanol.

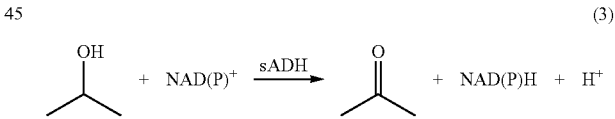

(3)

Secondary alcohol dehydrogenases that are suitable for use as cofactor regenerating systems in the ketoreductase-catalyzed reduction reactions described herein include both naturally occurring secondary alcohol dehydrogenases, as well as non-naturally occurring secondary alcohol dehydrogenases. Naturally occurring secondary alcohol dehydrogenases include known alcohol dehydrogenases from, *Thermoanerobium brockii*, *Rhodococcus etythropolis*, *Lactobacillus kefir*, and *Lactobacillus brevis*, and non-naturally occurring secondary alcohol dehydrogenases include engineered alcohol dehydrogenases derived therefrom. Secondary alcohol dehydrogenases employed in the methods described herein, whether naturally occurring or non-naturally occurring, may exhibit an activity of at least about 1 µmol/min/mg, sometimes at least about 10 µmol/min/mg, or at least about 10$^2$ µmol/min/mg, up to about 10$^3$ µmol/min/mg or higher.

Suitable secondary alcohols include lower secondary alkanols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In one embodiment the secondary alcohol is isopropanol. Suitable aryl-alkyl carbinols include unsubstituted and substituted 1-arylethanols.

When a secondary alcohol and secondary alcohol dehydrogenase are employed as the cofactor regeneration system, the resulting $NAD^+$ or $NADP^+$ is reduced by the coupled oxidation of the secondary alcohol to the ketone by the secondary alcohol dehydrogenase. Some engineered ketoreductases also have activity to dehydrogenate a secondary alcohol reductant. In some embodiments using secondary alcohol as reductant, the engineered ketoreductase and the secondary alcohol dehydrogenase are the same enzyme.

In carrying out embodiments of the ketoreductase-catalyzed reduction reactions described herein employing a cofactor regeneration system, either the oxidized or reduced form of the cofactor may be provided initially. As described above, the cofactor regeneration system converts oxidized cofactor to its reduced form, which is then utilized in the reduction of the ketoreductase substrate.

In some embodiments, cofactor regeneration systems are not used. For reduction reactions carried out without the use of a cofactor regenerating systems, the cofactor is added to the reaction mixture in reduced form.

In some embodiments, when the process is carried out using whole cells of the host organism, the whole cell may natively provide the cofactor. Alternatively or in combination, the cell may natively or recombinantly provide the glucose dehydrogenase.

In carrying out the stereoselective reduction reactions described herein, the engineered ketoreductase enzyme, and any enzymes comprising the optional cofactor regeneration system, may be added to the reaction mixture in the form of the purified enzymes, whole cells transformed with gene(s) encoding the enzymes, and/or cell extracts and/or lysates of such cells. The gene(s) encoding the engineered ketoreductase enzyme and the optional cofactor regeneration enzymes can be transformed into host cells separately or together into the same host cell. For example, in some embodiments one set of host cells can be transformed with gene(s) encoding the engineered ketoreductase enzyme and another set can be transformed with gene(s) encoding the cofactor regeneration enzymes. Both sets of transformed cells can be utilized together in the reaction mixture in the form of whole cells, or in the form of lysates or extracts derived therefrom. In other embodiments, a host cell can be transformed with gene(s) encoding both the engineered ketoreductase enzyme and the cofactor regeneration enzymes.

Whole cells transformed with gene(s) encoding the engineered ketoreductase enzyme and/or the optional cofactor regeneration enzymes, or cell extracts and/or lysates thereof, may be employed in a variety of different forms, including solid (e.g., lyophilized, spray-dried, and the like) or semi-solid (e.g., a crude paste).

The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the cell preparations may be stabilized by crosslinking using known crosslinking agents, such as, for example, glutaraldehyde or immobilization to a solid phase (e.g., Eupergit C, and the like).

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a prechilled lyophilization chamber, followed by the application of a vacuum. After the removal of water from the samples, the temperature is typically raised to 4° C. for two hours before release of the vacuum and retrieval of the lyophilized samples.

The quantities of reactants used in the reduction reaction will generally vary depending on the quantities of product desired, and concomitantly the amount of ketoreductase substrate employed. The following guidelines can be used to determine the amounts of ketoreductase, cofactor, and optional cofactor regeneration system to use. Generally, keto substrates can be employed at a concentration of about 20 to 300 grams/liter using from about 50 mg to about 5 g of ketoreductase and about 10 mg to about 150 mg of cofactor. Those having ordinary skill in the art will readily understand how to vary these quantities to tailor them to the desired level of productivity and scale of production. Appropriate quantities of optional cofactor regeneration system may be readily determined by routine experimentation based on the amount of cofactor and/or ketoreductase utilized. In general, the reductant (e.g., glucose, formate, isopropanol) is utilized at levels above the equimolar level of ketoreductase substrate to achieve essentially complete or near complete conversion of the ketoreductase substrate.

The order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor regeneration system, cofactor, ketoreductase, and ketoreductase substrate may be added first to the solvent.

For improved mixing efficiency when an aqueous co-solvent system is used, the cofactor regeneration system, ketoreductase, and cofactor may be added and mixed into the aqueous phase first. The organic phase may then be added and mixed in, followed by addition of the ketoreductase substrate. Alternatively, the ketoreductase substrate may be premixed in the organic phase, prior to addition to the aqueous phase Suitable conditions for carrying out the ketoreductase-catalyzed reduction reactions described herein include a wide variety of conditions which can be readily optimized by routine experimentation that includes, but is not limited to, contacting the engineered ketoreductase enzyme and substrate at an experimental pH and temperature and detecting product, for example, using the methods described in the Examples provided herein.

The ketoreductase catalyzed reduction is typically carried out at a temperature in the range of from about 15° C. to about 75° C. For some embodiments, the reaction is carried out at a temperature in the range of from about 20° C. to about 55° C. In still other embodiments, it is carried out at a temperature in the range of from about 20° C. to about 45° C. The reaction may also be carried out under ambient conditions.

The reduction reaction is generally allowed to proceed until essentially complete, or near complete, reduction of substrate is obtained. Reduction of substrate to product can be monitored using known methods by detecting substrate and/or product. Suitable methods include gas chromatography, HPLC, and the like. Conversion yields of the alcohol reduction product generated in the reaction mixture are generally greater than about 50%, may also be greater than about 60%, may also be greater than about 70%, may also be greater than about 80%, may also be greater than 90%, and are often greater than about 97%.

EXAMPLES

Various features and embodiments of the disclosure are illustrated in the following representative examples, which are intended to be illustrative, and not limiting.

Example 1: Production of Ketoreductase Powders; Shake Flask Procedure

A single microbial colony of E. coli containing a plasmid with the ketoreductase gene of interest was inoculated into 50 ml Tryptic broth (12 g/L bacto-tryptone, 24 g/L yeast extract, 4 ml/L glycerol, 65 mM potassium phosphate, pH 7.0) containing 30 µg/ml chloramphenicol and 1% glucose in a 250 ml Erlenmeyer flask. Cells were grown overnight (at least 16 hrs) in an incubator at 30° C. with shaking at 250 rpm. The culture was diluted into 250 ml Terrific Broth containing 1 mM $MgSO_4$, 30 µg/ml chloramphenicol in a 1 liter flask to an optical density at 600 nm (OD600) of 0.2 and allowed to grow at 30° C. Expression of the ketoreductase gene was induced with 1 mM IPTG when the OD600 of the culture is 0.6 to 0.8 and incubated overnight (at least 16 hrs). Cells were harvested by centrifugation (5000 rpm, 15 min, 4° C.) and the supernatant was discarded. The cell pellet was resuspended with an equal volume of cold (4° C.) 100 mM triethanolamine(chloride) buffer, pH 7.0 (including 1 mM $MgSO_4$ in the case of ADH-LK and ADH-LB and engineered ketoreductases derived there from), and harvested by centrifugation as above. The washed cells were resuspended in 12 ml of the cold triethanolamine(chloride) buffer and passed through a French Press twice at 12000 psi while maintained at 4° C. Cell debris was removed by centrifugation (9000 rpm, 45 min., 4° C.). The clear lysate supernatant was collected and stored at −20° C. Lyophilization of frozen clear lysate provided a dry powder of crude ketoreductase enzyme.

Example 2: Production of Ketoreductases; Fermentation Procedure

In an aerated agitated 15 L fermenter, 6.0 L of growth medium containing 0.88 g/L ammonium sulfate, 0.98 g/L of sodium citrate; 12.5 g/L of dipotassium hydrogen phosphate trihydrate, 6.25 g/L of potassium dihydrogen phosphate, 6.2 g/L of Tastone-154 yeast extract, 0.083 g/L ferric ammonium citrate, and 8.3 ml/L of a trace element solution containing 2 g/L of calcium chloride dihydrate, 2.2 g/L of zinc sulfate septahydrate, 0.5 g/L manganese sulfate monohydrate, 1 g/L cuprous sulfate heptahydrate, 0.1 g/L ammonium molybdate tetrahydrate and 0.02 g/L sodium tetraborate decahydrate was brought to a temperature of 30° C. The fermenter was inoculated with a late exponential culture of E. coli W3110, containing a plasmid with the ketoreductase gene of interest, grown in a shake flask as described in Example 3 to a starting OD600 of 0.5 to 2.0. The fermenter was agitated at 500-1500 rpm and air was supplied to the fermentation vessel at 1.0-15.0 L/min to maintain dissolved oxygen level of 30% saturation or greater. The pH of the culture was controlled at 7.0 by addition of 20% v/v ammonium hydroxide. Growth of the culture was maintained by the addition of a feed solution containing 500 g/L cerelose, 12 g/L ammonium chloride and 10.4 g/L magnesium sulfate heptahydrate. After the culture reached an OD600 of 50, the expression of ketoreductase was induced by the addition of isopropyl-β-D-thiogalactoside (IPTG) to a final concentration of 1 mM. The culture was grown for another 14 hours. The culture was then chilled to 4° C. and maintained at 4° C. until harvested. Cells were harvested by centrifugation at 5000G for 40 minutes in a Sorval RC12BP centrifuge at 4° C. Harvested cells were used directly in the following downstream recovery process or were stored at 4° C. until such use.

The cell pellet was resuspended in 2 volumes of 100 mM triethanolamine(chloride) buffer, pH 6.8, at 4° C. to each volume of wet cell paste. The intracellular ketoreductase was released from the cells by passing the suspension through a homogenizer fitted with a two-stage homogenizing valve assembly using a pressure of 12000 psig. The cell homogenate was cooled to 4° C. immediately after disruption. A solution of 10% w/v polyethyleneimine, pH 7.2, was added to the lysate to a final concentration of 0.5% w/v and stirred for 30 minutes. The resulting suspension was clarified by centrifugation at 5000G in a standard laboratory centrifuge for 30 minutes. The clear supernatant was decanted and concentrated ten fold using a cellulose ultrafiltration membrane with a molecular weight cut off of 30 Kd. The final concentrate was dispensed into shallow containers, frozen at −20° C. and lyophilized to powder. The ketoreductase powder was stored at −80° C.

Example 3: Analytical Methods for the Detection of methyl-2-benzamidomethyl-3-hydroxybutyrate Stereoisomers For routine analysis, the 2 stereoisomers of methyl-2-benzamidomethyl-3-oxobutyrate and the 4 stereoisomers of methyl-2-benzamidomethyl-3-hydroxybutyrate were separated by normal phase chiral HPLC on a Chiralpak IA column (4.6×150 mm (Chiral technologies, cat #80324); isocratic (92% heptane, 8% ethanol); 40° C.; 1.5 mL/min flow rate; sample volume: 10 µL; detection: UV absorbance at 254 nm). Retention times: 2S,3R-stereoisomer: 6.8 min., 2R,3S-diastereomer: 8.1 min, 2R,3R-stereoisomer: 9.3 min, 2S,3S-diastereomer: 10.1 min., substrate stereomers: 11.6 and 13.5 min.

Example 4: High Throughput NADPH Fluorescence Prescreen to Identify Variants Active on Isopropyl Alcohol (IPA)

Plasmid libraries obtained by directed evolution and containing evolved ketoreductase genes were transformed into E. coli and plated on Luria-Bertani (LB) broth containing 1% glucose and 30 µg/mL chloramphenicol (CAM). After incubation for at least 16 hrs at 30° C., colonies were picked using a Q-bot® robotic colony picker (Genetix USA, Inc., Beaverton, OR) into 96-well shallow well microtiter plates containing 180 µL Luria-Bertani (LB), 1% glucose, 30 µg/mL chloramphenicol (CAM), and 2 mM $MgSO_4$. Cells were grown overnight at 30° C. with shaking at 200 rpm. 20 µL of this culture was then transferred into 96-deep well plates containing 380 µL Terrific broth (TB), 2 mM $MgSO_4$ and 30 µg/mL CAM. After incubation of deep-well plates at 30° C. with shaking at 250 rpm for 2.5 to 3 hours ($OD_{600}$ 0.6-0.8), recombinant gene expression by the cell cultures was induced by isopropyl thiogalactoside (IPTG) to a final concentration of 1 mM. The plates were then incubated at 30° C. with shaking at 250 rpm for 15-23 hrs.

Cells were pelleted via centrifugation, resuspended in 400 μL lysis buffer and lysed by shaking at room temperature for at least 1 hour. The lysis buffer contained 100 mM triethanolamine(sulphate) buffer, pH 7.0-7.2, 1 mg/mL lysozyme and 200 μg/mL polymixin B sulfate and 2 mM $MgSO_4$. The plates are then spun in the centrifuge at 4000 RPM for 10 minutes at 4° C. and the clear supernatant (cleared supernatant) is used in the fluorescent assay.

In 96-well black microtiter plates 20 μl of lysate (10-fold dilution in 100 mM triethanolamine(sulfate) buffer pH7.0) was added to 180 μl of an assay mixture consisting of 100 mM triethanolamine(sulfate) buffer, pH 7.0, 1 mM $MgSO_4$, 1 g/L NADP, and 50% isopropylalcohol and the reaction progress measured by following the increase in fluorescence of NADPH at 445 nm after excitation at 330 nm in a Flexstation (Molecular Devices, USA).

Example 5: High Throughput HPLC Assay for Ketoreductase Activity on methyl-2-benzamidomethyl-3-oxobutyrate Using Isopropylalcohol for Co-Factor Recycling Lysates were prepared as described in Example 4. Ketoreductase activity was measured by transferring measured quantities of the cell lysates into the wells of Costar deep well plates (cat #3961). To 50 μL of 3 mg/ml Na-NADP in 100 mM triethanolamine(sulfate) buffer pH7.0, 150 μL of 3.3 mg/ml methyl-2-benzamidomethyl-3-oxobutyrate in IPA, 100 μL cleared lysate was added. The plates were heat sealed with aluminum/polypropylene laminate heat seal tape (Velocity 11 (Menlo Park, CA), Cat #06643-001), and incubated at room temperature for 24 hours with shaking. At the end of the reaction, 990 μL MTBE was added to each well, the plates were resealed and shaken for 20 minutes. The organic phase was separated from the aqueous phase by centrifugation (4000 rpm, 5 min., 4° C.) and 200 μL the organic layer transferred to a new shallow-well, 96-well plate for analysis using the methods described in Example 3.

Example 6: High Throughput HPLC Assay for Ketoreductase Activity on methyl-2-benzamidomethyl-3-oxobutyrate Using Isopropylalcohol for Co-Factor Recycling at Higher Substrate Concentration To wells of a 96-well microtiter plate was added 10 μL of 0.6 mg/ml Na-NADP in 100 mM triethanolamine(sulfate) buffer pH 7.0, 150 μL of 100 mg/ml ethyl-2-benzamidomethyl-3-oxobutyrate in IPA, 10 μL cleared lysate and 130 μL of 100 mM TEA. The plates were heat sealed and incubated at room temperature for 24 hours with shaking. At the end of the reaction, 990 μL MTBE was added to each well, the plates were heat sealed again and shaken for 20 minutes. The organic phase was separated from the aqueous phase by centrifugation (4000 rpm, 5 min., 4° C.) and 200 μL the organic layer transferred to a new shallow-well, 96-well plate for analysis using the methods described in Example 3.

This example describes the method that was used to identify KRED variants improved for the stereoselective reduction of methyl-2-benzamidomethyl-3-oxobutyrate.

Example 7: Evaluation of ADH-LK Variants for Reduction of Methyl-2-benzamidomethyl-3-oxobutyrate Several ADH-LK variants were evaluated for the stereoselective reduction of methyl-2-benzamidomethyl-3-oxobutyrate as described in Example 5. Samples were analyzed as described in Example 3.

Table 4 lists the SEQ ID NO. corresponding to the ketoreductase, the number of amino acid mutations from ADH-LK, the percent conversion and the percentage of the desired (2S,3R)-stereoisomer.

TABLE 4

| SEQ ID NO | Number of mutations from ADH-LK | activity[A] | stereoselectivity[B] |
|---|---|---|---|
| 90 | 1 | ++ | + |
| 92 | 4 | ++ | + |
| 96 | 1 | + | + |
| 98 | 1 | ++ | + |

[A]+: >30% conversion, ++: >60% conversion;
[B]+: >95% (2S,3R) isomer.

The ADH-LK variant with SEQ ID No. 90 was used for further evolution of an efficient KRED for production of (2S,3R)-methyl-2-benzamidomethyl-3-hydroxybutyrate. Similarly, an ADH-LK variant with SEQ ID No.94 containing 10 mutations compared to ADH-LK which gave primarily the (2R,3R) stereoisomer, was used for further evolution of an efficient KRED for production of (2R,3R)-methyl-2-benzamidomethyl-3-hydroxybutyrate.

This example shows that variants of ADH-LK can be useful for the stereoselective reduction of methyl-2-benzamidomethyl-3-oxobutyrate. New variants of SEQ ID No. 90 and 94 were generated in which an internal BglI site was removed. The corresponding new sequences are SEQ ID No. 48 and SEQ ID No. 66 respectively.

Example 8: Reduction of Methyl-2-benzamidomethyl-3-oxobutyrate to (2S,3R)-methyl-2-benzamidomethyl-3-hydroxybutyrate by Further Engineered Ketoreductases Derived from ADH-LK Improved ketoreductases derived from the ADH-LK variant with SEQ-ID No. 48 were evaluated for increased activity and (2S,3R)-stereoselectivity by the method described in Example 6.

TABLE 5

Activity of ADH-LK Variants for reduction of Methyl-2-benzamidomethyl-3-oxobutyrate to (2S,3R)-methyl-2-benzamidomethyl-3-hydroxybutyrate

| SEQ ID No. | mutations from kefir | # Mutations from ADH LK (SEQ ID: 4) | activity[a] | stability[b] | selectivity[c] |
|---|---|---|---|---|---|
| 2 | brevis | | | | |
| 4 | kefir | | | | |
| 48 | A202V; | 1 | + | | + |
| 38 | A94T; E105G; L153A; L199A; A202L; M206F; | 6 | + | | + |
| 16 | A94T; S96F; A202V; | 3 | + | | +++ |
| 56 | L153A; L199A; A202L; | 3 | + | | +++ |
| 58 | T86I; L199N; A202L; | 3 | + | | +++ |
| 52 | L153A; A202L; | 2 | + | | +++ |
| 54 | L153A; A202V; | 2 | + | | + |
| 32 | A94T; L199A; A202V; | 3 | ++ | | ++++ |
| 34 | A94T; L153A; L199H; A202L; | 4 | +++ | | ++++ |
| 50 | L153A; L199H; A202L; | 3 | ++ | | +++ |
| 20 | A94T; L199N; A202V; | 3 | +++ | | ++++ |
| 46 | L153S; A202L; | 2 | + | | + |
| 36 | A94T; L153A; L199A; A202V; | 4 | + | | ++ |
| 26 | A94T; A202L; | 2 | +++ | | +++ |

TABLE 5-continued

Activity of ADH-LK Variants for reduction of Methyl-2-benzamidomethyl-3-oxobutyrate to (2S,3R)-methyl-2-benzamidomethyl-3-hydroxybutyrate

| SEQ ID No. | mutations from kefir | # Mutations from ADH LK (SEQ ID: 4) | activity[a] | stability[b] | selectivity[c] |
|---|---|---|---|---|---|
| 28 | A94T; A202V; | 2 | ++ | | +++ |
| 30 | A94T; L199A; A202L; | 3 | +++ | | ++++ |
| 22 | A94T; L199H; A202L; | 3 | ++++ | | ++++ |
| 24 | A94T; L199H; A202V; | 3 | +++ | | ++++ |
| 42 | L153A; L199N; A202L; | 3 | + | | +++ |
| 40 | A94T; S96F; M129T; A202V; M206F; | 5 | + | | ++ |
| 18 | A80T; L153A; A202V; | 3 | + | | +++ |
| 44 | F147M; A202V; | 2 | + | + | |
| 10 | H40R; A94T; F147L; L199H; A202L; | 5 | +++++ | + | ++++ |
| 12 | H40R; A94T; L199H; A202L; | 4 | +++++ | | ++++ |
| 6 | A94T; F147L; L199H; A202L; | 4 | +++++ | + | ++++ |
| 8 | A94T; L199H; A202L; | 3 | +++++ | | ++++ |
| 60 | I11F; H40R; A94F; S96V; F147M; L195V; V196L; L199W; I226V; G248K; Y249W; | 11 | ++++ | | ++++ |
| 62 | T2A; R4C; H40R; A94G; S96V; F147M; V196L; L199W; I226V; G248K; Y249W; | 11 | +++ | | ++++ |
| 14 | H40R; A94F; S96V; F147M; L195V; V196L; L199W; I226V; Y249W; | 9 | ++++ | | ++++ |

[a]+: 1-15-fold more active than KRED with SEQ ID No. 48; ++: 15-30-fold more active than KRED with SEQ ID No. 48; +++: 30-40-fold more active than KRED with SEQ ID No. 48; ++++: 40-50-fold more active than KRED with SEQ ID No. 48; +++++: >50-fold more active than KRED with SEQ ID No. 48,
[b]+: retains activity after 21 hours preincubation at 40° C.,
[c]+: 60-89% (2S,3R)-product; ++: 90-94% (2S,3R)-product; +++: 95-99% (2S,3R)-product; ++++: >99% (2S,3R)-product.

Example 9: Reduction of Methyl-2-benzamidomethyl-3-oxobutyrate to (2R, 3R)-methyl-2-benzamidomethyl-3-hydroxybutyrate by Engineered Ketoreductases Derived from ADH-LK Improved ketoreductases derived from the ADH-LK variant with SEQ-ID) No. 66 were evaluated for increased activity and (2R,3R)-stereoselectivity by the method described in Example 6.

TABLE 6

Activity of ADH-LK Variants for reduction of Methyl-2-benzamidomethyl-3-oxobutyrate to (2R,3R)-methyl-2-benzamidomethyl-3-hydroxybutyrate

| SEQ ID NO | Sequence - coding mutations | Number of mutations from kefir | activity[a] | selectivity[b] |
|---|---|---|---|---|
| 66 | H40R; A94G; S96V; E145F; F147M; Y190P; V196L; L199W; I225V; Y249W | 10 | + | + |
| 74 | I11F; H40R; A94E; S96V; E145F; F147M; Y190P; L195V; V196L; L199W; I226V; Y249H; | 12 | ++ | ++ |
| 82 | D3V; A10T; H40R; A94G; S96V; F147M; Y190P; V196L; L199W; I226V; G248K; Y249H; | 12 | + | ++ |
| 68 | H40R; A94F; S96V; E145F; F147M; Y190P; L195V; V196L; L199W; I226V; G248R; Y249W; | 12 | ++ | ++ |
| 76 | I11L; H40R; A94E; S96V; F147M; Y190H; V196L; I226V; G248K; Y249H; | 10 | +++ | ++ |
| 72 | H40R; T54A; A94F; S96V; E105K; E145D; F147M; V196L; L199W; I226V; Y249W; | 11 | +++ | ++ |
| 78 | I11F; H40R; A94G; S96V; E145F; F147M; Y190H; L195V; V196L; L199W; A202V; I226V; Y249H; A251T; | 14 | +++ | ++ |
| 70 | H40R; E78D; A94E; S96V; F147M; Y190H; L195V; V196L; I226V; Y249H; T250Y; | 11 | +++ | + |
| 80 | K8N; V9G; I11F; H40R; A94G; S96V; E145F; F147M; Y190P; V196L; I226V; G248K; Y249R; | 13 | +++ | + |
| 64 | V12I; H40R; A94E; S96V; F147M; Y190P; L195V; V196L; L199W; I226V; G248R; Y249W; | 12 | +++ | + |

[a]+: 1-fold more active than KRED with SEQ ID NO. 66; ++: 1-2-fold more active than KRED with SEQ ID NO. 66; +++: >2-fold more active than KRED with SEQ ID NO. 66;
[b]+: <85% (2R,3R)-product; ++: >85% (2R,3R)-product.

Example 10: Preparative Scale Production of (2S, 3R)-methyl-2-benzamidomethyl-3-hydroxybutyrate A 250 ml 3-neck flask with overhead stirrer was charged with methyl 2-benzamidomethyl-3-ketobutyrate (25 g), isopropylalcohol (37.5 ml) and 0.1 M triethanolamine(chloride)/0.04 M $MgSO_4$ buffer pH7.2 (30 ml). The reaction mixture is stirred and temperature brought up to 37° C. using an oil bath. The reaction is started with the addition of 0.5 ml 19 g/L NADP-Na followed by 2.5 ml 30 g/L KRED of SEQ ID No. 10; both as solutions in 0.1 M triethanolamine (chloride)/0.04 M $MgSO_4$ buffer pH 7.2. The reaction progress was followed by taking 5 µl aliquots over the course of the reaction that were diluted with 1 ml acetonitrile, filtered through a 0.25 µm syringe filter and analyzed as described in Example 3. When the conversion exceeded 96% saturated aqueous sodium chloride (12.5 ml) was added to the reaction mixture, followed by 40 ml ethyl acetate. The reaction mixture was stirred for another 15 minutes, then filtered through a Celite pad (5 g in a fritted glass filter) under vacuum. The filter cake was washed with 20 ml ethyl acetate and the two phases of the filtrate allowed to separate. The organic layer is washed three times with 20 ml water and concentrated on a rotary evaporator to an oil of constant weight. After removal of ethyl acetate, toluene (10 ml) was added and distilled under vacuum. (2S, 3R)-methyl-2-benzamidomethyl-3-hydroxybutyrate (26.47 g) was obtained as an oil containing ~10% toluene as determined by $^1$H-NMR-$CDCl_3$.

All publications, patents, patent applications and other documents cited in this application are hereby incorporated by reference in their entireties for all purposes to the same extent as if each individual publication, patent, patent application or other document were individually indicated to be incorporated by reference for all purposes.

What is claimed is:

1. An engineered ketoreductase polypeptide having ketoreductase activity,
wherein said ketoreductase polypeptide is at least 85% identical to SEQ ID NO:4, and
wherein the ketoreductase polypeptide comprises the following fetures:
the resiude at the position corresponding to position 153 is alanine or serine,
the residue at position corresponding to position 202 is valine or leucine, and
wherein the residue at the position corresponding to position 94 is threonine.

2. The engineered ketoreductase polypeptide of claim 1, wherein said ketoreductase polypeptide further comprises at least one of the following features recited under [1] or [2]:
[1] the residue at the position corresponding to position 199 is a histidine, alanine, or asparagine; or
[2] the residue at the position corresponding to position 199 is an aliphatic, constrained or polar residue.

3. The engineered ketoreductase polypeptide of claim 1, wherein the residue at the position corresponding to position 199 is alanine, histidine, or asparagine.

4. The engineered ketoreductase polypeptide of claim 1, wherein the residue at the position corresponding to position 199 is an aliphatic, constrained or polar residue.

5. The engineered ketoreductase polypeptide of claim 1, wherein the residue at the position corresponding to position 199 is alanine, histidine, or asparagine.

6. The engineered ketoreductase polypeptide of claim 1, further comprising one or more of the following features:
the residue at the position corresponding to position 2 is a polar, non-polar, or aliphatic residue;
the residue at the position corresponding to position 4 is a basic residue or cysteine;
the residue at the position corresponding to position 11 is a non-polar, aliphatic, or aromatic residue;
the residue at the position corresponding to position 80 is a non-polar, aliphatic, or polar residue;
the residue at the position corresponding to position 86 is a non-polar, aliphatic, or polar residue;
the residue at the position corresponding to position 96 is a polar, aromatic, non-polar, or aliphatic residue;
the residue at the position corresponding to position 105 is a non-polar, aliphatic, basic or acidic residue;
the residue at the position corresponding to position 129 is a non-polar or polar residue;
the residue at the position corresponding to position 147 is an aromatic, non-polar or aliphatic residue;
the residue at the position corresponding to position 190 is an aromatic or constrained residue;
the residue at the position corresponding to position 195 is a non-polar or aliphatic residue;
the residue at the position corresponding to position 196 is a non-polar or aliphatic residue;
the residue at the position corresponding to position 206 is a non-polar or aromatic residue;
the residue at the position corresponding to position 248 is a non-polar or basic residue; and
the residue at the position corresponding to position 249 is an aromatic residue; and
wherein optionally the amino acid sequence has one or more residue differences at other amino acid residue positions as compared to SEQ ID NO:4.

7. The engineered ketoreductase polypeptide of claim 1, further comprising one or more of the following features:
the residue at the position corresponding to position 2 is alanine;
the residue at the position corresponding to position 4 is cysteine;
the residue at the position corresponding to position 11 is phenylalanine;
the residue at the position corresponding to position 80 is threonine;
the residue at the position corresponding to position 86 is isoleucine;
the residue at the position corresponding to position 96 is valine or phenylalanine;
the residue at the position corresponding to position 105 is glycine;
the residue at the position corresponding to position 129 is threonine;
the residue at the position corresponding to position 147 is methionine or leucine;
the residue at the position corresponding to position 190 is histidine or proline;
the residue at the position corresponding to position 195 is valine;
the residue at the position corresponding to position 196 is leucine;
the residue at the position corresponding to position 206 is phenylalanine;
the residue at the position corresponding to position 248 is lysine, or arginine; and
the residue at the position corresponding to position 249 is tryptophan;
wherein optionally the amino acid sequence has one or more residue differences at other amino acid residue positions as compared to SEQ ID NO:4.

8. The engineered ketoreductase polypeptide of claim 1, further comprising the feature that the residue corresponding to X147 is an aromatic, non-polar or aliphatic residue.

9. The engineered ketoreductase polypeptide of claim 1, further comprising one or more of the following features:
the residue at the position corresponding to position 96 is a polar, aromatic, non-polar, or aliphatic;
the residue at the position corresponding to position 195 is a non-polar or aliphatic residue;
the residue at the position corresponding to position 196 is a non-polar or aliphatic residue;
the residue at the position corresponding to position 248 is a non-polar or basic residue; and
the residue at the position corresponding to position 249 is an aromatic residue.

10. The engineered ketoreductase polypeptide of claim 1, further comprising one or more of the following features:
the residue at the position corresponding to position 2 is a polar, non-polar, or aliphatic residue;
the residue at the position corresponding to position 4 is a basic residue or cysteine;
the residue at the position corresponding to position 11 is a non-polar, aliphatic, or aromatic residue;
the residue at the position corresponding to position 80 is a non-polar, aliphatic, or polar residue;
the residue at the position corresponding to position 86 is a non-polar, aliphatic, or polar residue;
the residue at the position corresponding to position 105 is a non-polar, aliphatic, basic or acidic residue;
the residue at the position corresponding to position 129 is a non-polar or polar residue;
the residue at the position corresponding to position 190 is an aromatic or constrained residue; and the residue at the position corresponding to position 206 is a non-polar or aromatic residue.

11. The engineered ketoreductase polypeptide of claim 1, further comprising one or more of the following features: the residue at the position corresponding to position 147 is an aromatic, non-polar or aliphatic residue; and wherein optionally the amino acid sequence has one or more residue differences at other amino acid residue positions as compared to SEQ ID NO:4.

12. The engineered ketoreductase polypeptide of claim 1, further comprising one or more of the following features: the residue at the position corresponding to position 96 is a polar, aromatic, non-polar, or aliphatic residue; the residue at the position corresponding to position 147 is an aromatic, non-polar or aliphatic residue; and wherein optionally the amino acid sequence has one or more residue differences at other amino acid residue positions as compared to SEQ ID NO:4.

13. The engineered ketoreductase polypeptide of claim 1, further comprising one or more of the following features:
    residue at the position corresponding to position 96 is a polar, aromatic, non-polar, or aliphatic residue;
    residue at the position corresponding to position 147 is an aromatic, non-polar or aliphatic;
    residue at the position corresponding to position 195 is a non-polar or aliphatic residue;
    residue at the position corresponding to position 196 is a non-polar or aliphatic residue; and
    wherein optionally the amino acid sequence has one or more residue differences at other amino acid residue positions as compared to SEQ ID NO:4.

14. The engineered ketoreductase polypeptide of claim 1, further comprising the feature that the residue at the position corresponding to position 147 is methionine or leucine.

* * * * *